US009687153B2

(12) United States Patent
Milner

(10) Patent No.: US 9,687,153 B2
(45) Date of Patent: Jun. 27, 2017

(54) HEMOGLOBIN CONTRAST IN MAGNETO-MOTIVE OPTICAL DOPPLER TOMOGRAPHY, OPTICAL COHERENCE TOMOGRAPHY, AND ULTRASOUND IMAGING METHODS AND APPARATUS

(71) Applicant: BOARD OF REGENTS, THE UNIVERSITY OF TEXAS SYSTEM, Austin, TX (US)

(72) Inventor: Thomas E. Milner, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/954,936

(22) Filed: Nov. 30, 2015

(65) Prior Publication Data

US 2016/0150961 A1    Jun. 2, 2016

Related U.S. Application Data

(63) Continuation of application No. 13/722,553, filed on Dec. 20, 2012, now Pat. No. 9,198,596, which is a
(Continued)

(51) Int. Cl.
*A61B 5/05* (2006.01)
*A61B 5/00* (2006.01)
(Continued)

(52) U.S. Cl.
CPC .......... *A61B 5/0066* (2013.01); *A61B 5/0035* (2013.01); *A61B 5/026* (2013.01);
(Continued)

(58) Field of Classification Search
CPC . A61B 2576/00; A61B 5/0035; A61B 5/0066; A61B 5/026; A61B 5/0261; A61B 5/0275; A61B 5/05; A61B 5/0515; A61B 5/6852; A61B 5/725; A61B 8/06; A61B 8/13; A61B 8/488; A61N 2/02; G01N 21/1717; G01N 21/4795
See application file for complete search history.

(56) References Cited

U.S. PATENT DOCUMENTS

| 4,676,980 A | 6/1987 | Segal et al. ..................... 424/85 |
| 4,816,567 A | 3/1989 | Cabilly et al. ................ 530/387 |

(Continued)

FOREIGN PATENT DOCUMENTS

| WO | WO 93-06213 | 4/1993 | ............. C12N 15/00 |
| WO | WO 93-08829 | 5/1993 | ............. A61K 37/04 |

(Continued)

OTHER PUBLICATIONS

Adler, et al., "Phase-sensitive optical coherence tomography at up to 370,000 lines per second using buffered Fourier domain mode-locked lasers" *Optics Letters* 32(6): 626-628 (2007).
(Continued)

*Primary Examiner* — Mark Remaly
(74) *Attorney, Agent, or Firm* — J. Peter Paredes; David G. Rosenbaum; Rosenbaum IP, P.C.

(57) ABSTRACT

Provided herein are systems, methods, and compositions for the use of optical coherence tomography for detection of cells.

20 Claims, 19 Drawing Sheets

Related U.S. Application Data continuation of application No. 11/874,519, filed on Oct. 18, 2007, now Pat. No. 8,355,776, which is a continuation-in-part of application No. 11/550,771, filed on Oct. 18, 2006, now Pat. No. 8,036,732, which is a continuation-in-part of application No. 11/441,824, filed on May 26, 2006, now Pat. No. 7,983,737, said application No. 13/722,553 is a continuation-in-part of application No. 11/784,477, filed on Apr. 6, 2007, now Pat. No. 7,801,590.

(60) Provisional application No. 60/685,559, filed on May 27, 2005, provisional application No. 60/790,248, filed on Apr. 7, 2006.

(51) Int. Cl.

| | | |
|---|---|---|
| A61B 5/026 | (2006.01) | |
| A61B 5/0275 | (2006.01) | |
| A61B 8/06 | (2006.01) | |
| A61B 8/13 | (2006.01) | |
| G01N 21/17 | (2006.01) | |
| G01N 21/47 | (2006.01) | |
| A61B 8/08 | (2006.01) | |
| A61N 2/02 | (2006.01) | |

(52) U.S. Cl.
CPC .......... *A61B 5/0261* (2013.01); *A61B 5/0275* (2013.01); *A61B 5/05* (2013.01); *A61B 5/0515* (2013.01); *A61B 5/6852* (2013.01); *A61B 5/725* (2013.01); *A61B 8/06* (2013.01); *A61B 8/13* (2013.01); *A61B 8/488* (2013.01); *A61N 2/02* (2013.01); *G01N 21/1717* (2013.01); *G01N 21/4795* (2013.01); *A61B 2576/00* (2013.01)

(56) References Cited

U.S. PATENT DOCUMENTS

| | | | |
|---|---|---|---|
| 5,109,276 A | 4/1992 | Nudelman et al. | 358/88 |
| 5,262,176 A | 11/1993 | Palmacci et al. | 424/9 |
| 5,565,332 A | 10/1996 | Hoogenboom et al. | 435/69.1 |
| 5,596,079 A | 1/1997 | Smith et al. | 530/328 |
| 5,795,205 A | 8/1998 | Hellmuth et al. | 600/407 |
| 5,824,520 A | 10/1998 | Mulligan-Kehoe | 435/91.41 |
| 5,921,244 A | 7/1999 | Chen et al. | 128/897 |
| 5,991,697 A | 11/1999 | Nelson et al. | 702/49 |
| 6,031,071 A | 2/2000 | Mandeville et al. | 530/300 |
| 6,191,862 B1 | 2/2001 | Swanson et al. | 356/450 |
| 6,520,911 B1 | 2/2003 | Wen | 600/437 |
| 6,530,944 B2 | 3/2003 | West et al. | 607/88 |
| 6,608,684 B1 | 8/2003 | Gelikonov et al. | 356/479 |
| 6,687,010 B1 | 2/2004 | Horii et al. | 356/479 |
| 6,795,195 B1 | 9/2004 | Barbour et al. | 356/446 |
| 8,355,776 B2 * | 1/2013 | Milner | A61B 5/0066 600/476 |
| 2001/0036002 A1 | 11/2001 | Tearney et al. | 359/287 |
| 2002/0049375 A1 | 4/2002 | Strommer et al. | 600/407 |
| 2002/0077546 A1 | 6/2002 | Aldefeld et al. | 600/424 |
| 2002/0190212 A1 | 12/2002 | Boas et al. | 250/341.1 |
| 2002/0193785 A1 | 12/2002 | Naghavi et al. | 606/28 |
| 2002/0198457 A1 | 12/2002 | Tearney et al. | 600/476 |
| 2003/0023153 A1 | 1/2003 | Izatt et al. | 600/407 |
| 2003/0055307 A1 | 3/2003 | Elmaleh et al. | 600/1 |
| 2003/0064965 A1 | 4/2003 | Richter | 514/102 |
| 2003/0137699 A1 | 7/2003 | Narazaki et al. | 356/479 |
| 2003/0233033 A1 | 12/2003 | Korotko et al. | 600/301 |
| 2003/0236458 A1 | 12/2003 | Hochman | 600/431 |
| 2004/0023415 A1 | 2/2004 | Sokolov et al. | 436/518 |
| 2004/0059220 A1 | 3/2004 | Mourad et al. | 600/442 |
| 2004/0098070 A1 | 5/2004 | Mohr et al. | 607/89 |
| 2004/0239942 A1 | 12/2004 | Sun | 356/479 |
| 2004/0254419 A1 | 12/2004 | Wang et al. | 600/8 |
| 2004/0258759 A1 | 12/2004 | Suslick et al. | 424/490 |
| 2005/0018201 A1 | 1/2005 | de Boer et al. | 356/479 |
| 2005/0113678 A1 | 5/2005 | Villard et al. | 600/425 |
| 2005/0165298 A1 | 7/2005 | Larson et al. | 600/410 |
| 2005/0168735 A1 | 8/2005 | Boppart et al. | 356/301 |
| 2005/0171433 A1 | 8/2005 | Boppart et al. | 600/473 |
| 2005/0190372 A1 | 9/2005 | Dogariu | 356/479 |
| 2005/0203424 A1 | 9/2005 | Boese et al. | 600/478 |
| 2005/0256207 A1 | 11/2005 | McGrath | 514/673 |
| 2006/0058642 A1 | 3/2006 | Franconi et al. | 600/420 |
| 2006/0100528 A1 | 5/2006 | Chan et al. | 600/476 |
| 2006/0132790 A1 | 6/2006 | Gutin | 356/479 |
| 2006/0142746 A1 | 6/2006 | Friedman et al. | 606/11 |
| 2006/0256343 A1 | 11/2006 | Choma et al. | 356/450 |
| 2007/0168001 A1 | 7/2007 | Xiang et al. | 607/101 |
| 2008/0095714 A1 | 4/2008 | Castella et al. | 424/9.3 |

FOREIGN PATENT DOCUMENTS

| | | | | |
|---|---|---|---|---|
| WO | WO 96-23524 | 8/1996 | ............ | A61K 49/00 |
| WO | WO 99-13916 | 3/1999 | ............ | A61K 49/00 |
| WO | WO 2004-096049 | 11/2004 | | |

OTHER PUBLICATIONS

Anderson, et al., "Selective photothermolysis: Precise microsurgery by selective absorption of pulsed radiation" *Science* 220: 524-527 (1983).

Aslan, et al., "Tunable plasmonic glucose sensing based on the dissociation of Con-A aggregated dextran-coated gold colloids" *Analytica Chimica Acta* 517: 139-144 (2004).

Brezinski, et al., "Optical coherence tomography for optical biopsy. Properties and demonstration of vascular pathology" *Circulation* 93(6): 1206-1213 (1996).

Caplan, et al., "Near-infrared spectroscopy for the detection of vulnerable coronary artery plaques" *JACC* 47(8C): 92-96 (2006).

Chen, et al., "Optical Doppler tomographic imaging of fluid flow velocity in highly scattering media" *Optics Letters* 22(1): 64-66 (1997).

Cilingiroglu, et al., "Detection of vulnerable plaque in a murine model of atherosclerosis with optical coherence tomography" *Catheterization and Cardiovascular Interventions* 67: 915-923 (2006).

Clackson, et al., "Making antibody fragments using phage display libraries" *Nature* 352: 624-628 (1991).

Daniel, et al., "Gold nanoparticles: Assembly, superamolecular chemistry, quantum-size-related properties, and applications toward biology, catalysis, and nanotechnology" *Chem Rev* 104: 293-346 (2004).

Dave, et al., "Optical low-coherence reflectometer for differential phase measurement" *Optical Letters* 25(4): 227-229 (2000).

Dave, et al., "Polarization-maintaining fiber-based optical low-coherence reflectometer for characterization and ranging of birefringence" *Optics Letters* 28(19): 1775-1777 (2003).

David, et al., "Protein iodination with solid state lactoperoxidase" *Biochemistry* 13(5): 1014-1021 (1974).

deBoer, et al., "Polarization-sensitive optical coherence tomography" *Handbook Of Optical Coherence Tomography*: pp. 237-274 (2002).

Elghanian, et al., "Selective colorimetric detection of polynucleotides based on the distance-dependent optical properties of gold nanoparticles" *Science* 277(5329): 1078-1081 (1997).

Fujimoto, et al., "High resolution in vivo intra-arterial imaging with optical coherence tomography" *Heart* 82: 128-133 (1999).

Goding, "Monoclonal Antibodies: Principles and Practice" pp. 59-103 (1986).

Griffiths, et al., "Human anti-self antibodies with highly specificity from phage display libaries" *The EMBO Journal* 12(2): 725-734 (1993).

Griffiths, et al., "Isolation of high affinity human antibodies directly from large synthetic repertoires" *The EMBO Journal* 13(14): 3245-3260 (1994).

Harlow et al., "Antibodies: A Laboratory Manual" *Cold Spring Harbor Laboratory* (1988).

(56) References Cited

OTHER PUBLICATIONS

Huber, et al., "Buffered Fourier domain mode locking: unidirectional swept laser sources for optical coherence tomography imaging at 370,000 lines/s" *Optics Letters* 31: 2975-2977 (2006).
Huber, et al., "Fourier Domain Rilode Locking (FDML): A new laser operating regime and applications for optical coherence tomography" *Optics Express* 14: 3225-3237 (2006).
Hunter, et al., "Preparation of iodine-131 labeled human growth hormone of high specific activity" *Nature* 194(4827): 495-496 (1962).
Jakobovits, et al., "Germ-line transmission and expression of a human-derived yeast artificial chromosome" *Nature* 362: 255-258 (1993).
Jang, et al., "Visualization of coronary atherosclerotic plaques in patients using optical coherence tomography: comparision with intravascular ultrasound" *JACC* 39: 604-609 (2002).
Johnson, et al., "Plaque rupture after short periods of fat feeding in the apolipoprotein E-knockout mouse: model characterization and effects of Pravastatin treatment" *Circulation* 111: 1422-1430 (2005).
Johnson, et al., "Human Antibody Engineering" *Current Opinion in Structural Biology* 3: 564-571 (1993).
Jones, et al., "Replacing the complementarity-determining regions in a human antibody with those from a mouse" *Nature* 321: 522-525 (1986).
Josephson, et al., "High-efficiency intracellular magnetic labeling with novel superparamagnetic-tat peptide conjugates" *Bioconjugate Chemistry* 10: 186-191 (1999).
Kane, "Introduction to Physics in Modern Medicine" *Taylor & Francis/CRC Press*, Baco Raton, FL. (2003).
Kelly, et al., "Detection of vascular adhesion molecule-1 expression using a novel multimodal nanoparticle" *Circulation Research* 96: 327-336 (2005).
Kemp, et al., "High-sensitivity determination of birefringence in turbid media with enhanced polarization-senstive optical coherence tomography" *Journal of the Optical Society of America A.* 22(3): 552-560 (2005).
Kim, et al., "Hemoglobin contrast in magnetomotive optical doppler tomography" *Optics Letters* 31(6): 778-780 (2006).
Kohler, et al., "Continuous cultures of fused cells secreting antibody of predefined specificity" *Nature* 256: 495-497 (1975).
Kozbor, et al., "A human hybrid myeloma for production of human monoclonal antibodies" *The Journal of Immunology* 133(6): 3001-3005 (1984).
Kuo, "Polarization sensitive OCT for imaging human atherosclerosis" *Applied Optics* 46(13): 2520-2527 (2007).
Landini, et al., "New technological developments in the clinical imaging of atherosclerotic plaque" *Current Pharmaceutical Design* 9: 2403-2415 (2003).
Lee, et al., "Engineered microsphere contrast agents for optical coherence tomography" *Optics Letters* 28(17): 1546-1548 (2003).
Leitgeb, et al., "Performance of fourier domain vs time domain Optical Coherence Tomography" *Optics Express* 11: 889-894 (2003).
Loo, et al., "Nanoshell-enabled photonics-based imaging and therapy of cancer" *Technology in Cancer Research & Treatment* 3(1): 33-40 (2004).
MacNeill, et al., "Intravascular modalities for detection of vulnerable plaque" *Arterioscler Thromb Vasc Biol* 23: 1333-1342 (2003).
Mandel et al., "Magnetite nanoparticles with tunable gold or silver shell" *Journal Colloid Interface Science* 286: 187-194 (2005).
Marks, et al, "By-passing immunization: building high affinity human antibodies by chain shuffling" *Nature Biotechnology* 10: 779-783 (1992).
Marks, et al., "By-passing immunization human antibodies from v-gene libraries displayed on phage" *Journal of Molecular Biology* 222: 581-597 (1991).
McCafferty, et al., "Phage antibodies: filamentous phage displaying antibody variable domains" *Nature* 348: 552-554 (1990).

Milstein, et al., "Hybrid hybridomas and their use in immunohistochemistry" *Nature* 305: 537-540 (1983).
Mindlin, "Force at a point in the interior of a semi-infinite solid" *Physics* 7:195-202 (1936).
Monk, "Finite element methods for Maxwell's Equations" *Oxford University Press* (2003).
Moreno, et al., "Detection of high risk atherosclerotic coronary plaques by intravascular spectroscopy" *J Interven Cardiol* 16: 243-252 (2003).
Mornet, et al., "Magnetic nanoparticle design for medical diagnosis and therapy" *J Mater Chem* 14: 2161-2175 (2004).
Morrison, et al., "Chimeric human antibody molecules: mouse antigen-binding domains with human constant region domains" *Proceedings of the National Academy of Sciences of the United States of America* 81(21): 6851-6855 (1984).
Motta, et al., "High magnetic field effects on human deoxygenated hemoglobin light absorption" *Bioelectrochemistry and Bioenergetics* 47: 297-300 (1998).
Munson, et al., "LIGAND: A versatile computerized approach for characterization of ligand-binding systems" *Analytical Biochemistry* 107: 220-239 (1980).
Nakamura, et al., "Identification and treatment of vulnerable plaque" *Rev. in Cardiovascular Med.* 5(Suppl. 2): S22-233 (2004).
Nogueira, et al., "Raman spectroscopy study of atherosclerosis in human carotid artery" *J Biomed Opt* 10(3): 031117 (2005).
Nygren, "Conjugation of horseradish peroxidase to fab fragments with different homobifunctional and heterobifunctional cross-linking reagents" *The Journal of Histochemistry and Cytochemistry* 30(5): 407-412 (1982).
Oh, et al., "Detection of magnetic nanoparticles in tissue using magneto-motive ultrasound" *Nanotechnology* 17: 4183-4190 (2006).
Oh, et al., "Magneto-motive detection of tissue-based macrophages by differential phase optical coherence tomography" *Lasers in Surgery and Medicine, Wiley-Liss, Inc.* pp. 1-5 (2007)
Oldenburg, et al., "Infrared extinction properties of gold nanoshells" *Applied Physics Letters* 75: 2897-2899 (1999).
Oldenburg, et al., "Magnetic contrast agents for optical coherence tomography" *Proc. SPIE* 5316: 26-28 (2004).
Oldenburg, et al., "Imaging magnetically labeled cells with magnetomotive optical coherence tomography" *Optics Letters* 30(7): 747-749 (2005).
Oldenburg, et al., "Nanoengineering of optical resonances" *Chemical Physics Letters* 288: 243-247 (1998).
Otis, et al., "Quantifying labial blood flow using optical Doppler tomography" *Oral Surg Oral Med Oral Pathol Oral Radiol Endod* 98: 189-194 (2004).
Pain, et al., "Preparation of protein a-peroxidase monoconjugate using a heterobifunctional reagent, and its use in enzyme immunoassays" *Journal of Immunological Methods* 40: 219-230 (1981).
Piao, et al., "Quantifying Doppler angle and mapping flow velocity by a combination of Doppler-shift and Doppler-bandwidth measurements in optical doppler tomography" *Applied Optics* 42(25): 5158-5166 (2003).
Pitsillides, et al., "Selective cell targeting with light absorbing microparticles and nanoparticles" *Biophysical Journal* 84: 4023-4032 (2003).
Raghunand, et al., "Microenvironmental and cellular consequences of altered blood flow in tumours" *The British Journal of Radiology* 76: S11-S22 (2003).
Regar, et al., "Optical Coherence Tomography" *Cardiovascular Rad. Med.* 4: 198-204 (2003).
Reynolds, et al., "Method of determining nanoparticle core weight" *Analytical Chemistry* 77: 814-817 (2005).
Riechmann, et al., "Reshaping human antibodies for therapy" *Nature* 332: 323-327 (1988).
Robles, et al., "Short-duration high-frequency quasi-sinusoidal magnetic field generator" *IEEE Transactions on Instrumentation and Measurement* 54(6): 2481-2485 (2005).
Rylander, et al., "Quantitative phase-contrast imaging of cells with phase-sensitive optical coherence microscopy" *Optics Letters* 29(13): 1509-1511 (2004).

(56) References Cited

OTHER PUBLICATIONS

Schenck, "Physical interactions of static magnetic fields with living tissues" *Prowess in Biophysics and Molecular Biology* 87: 185-204 (2005).

Schroder, "Fast pulsed magnet systems" *Handbook of Accelerator Physics and Engineering* (1998).

Shen, et al., "Manocrystalline iron oxide nanocompounds (MION): Physicochemical properties" *Magnetic Resonance Medicine* 29: 599-604 (1993).

Siiman, et al., "Fluorescent neoglycoproteins: antibody-aminodextran-phycobiliprotein conjugates" *Bioconjugate Chemistry* 10: 1090-1106 (1999).

Siiman, et al., "Surface-enhanced raman scattering (SERS) of random silver or gold particle arrays on aminodextran-coated polystyrene beads" *Journal Raman Spectroscopy* 36: 1125-1133 (2005).

Silveira et al. "Correlation between near-infrared Raman spectroscopy and the histopathological analysis of atherosclerosis in human coronary arteries" *Lasers Surg Med* 30(4): 290-297 (2002).

Sirol, et al., "Molecular imaging for the diagnosis of high-risk plaque" *Cardiovascular Res.* 96(12): 1219-1224 (2003).

Sun, et al., "Development of nanoparticle libraries for biosensing" *Bioconjugate Chemistry* 17: 109-113 (2006)

Sun, et al., "Increased sensitivity of surface plasmon resonance of gold nanoshells compared to that of fold solid colloids in response to environmental changes" *Analytical Chemistry* 74: 5297-5305 (2002).

Suresh, et al., "Bispecific monoclonal antibodies from hybrid hybridomas" *Methods in Enzymology* 121: 210-228 (1986).

Taylor, et al., "The magnetic susceptibility of the iron in ferrohemoglobin" *Journal of the American Chemical Society* 60: 1177-1181 (1938).

Tearney, et al., "Quantification of macrophage content in atherosclerotic plaques by optical coherence tomography" *Circulation* 107: 113-119 (2003).

Traunecker, et al., "Bispecific single chain molecules (janusins) targets cytotoxic lymphocytes on HIV infected cells" *The EMBO Journal* 10(12): 3655-3659 (1991).

Vakoc, et al., "Phase-resolved optical frequency domain imaging" *Optics Express* 13: 5483-5493 (2005).

Verhoeyen, et al., "Reshaping human antibodies: Grafting an antilysozyme activity" *Science* 239(4847): 1534-1536 (1988).

Villard, et al., "Use of a blood substitute to determine instantaneous murine right ventricular thickening with optical coherence tomography" *Circulation: Journal of the American Heart Association* 105: 1843-1849 (2002).

Wang, et al., "Immobilization and characterization of Gamma Aminobutyric acid on gold surface" *Journal Biomedical Materials Research, Part A* 79(1): 201-209.

Wang, et al., "Monodispersed core-shell $Fe_3O_4$@Au nanoparticles" *J Phys Chem B* 109: 21593-21601 (2005).

Wang, et al., "Characterization of fluid flow velocity by optical Doppler tomography" *Optics Letters* 20(11): 1337-1339 (1995).

Waterhouse et al., "Combinatorial infection and in vivo recombination: A strategy for making large phage antibody repertoires" *Nucleic Acids Research* 21(19): 2265-2266 (1993).

Weissleder, "A clearer vision for in vivo imaging" *Nature Biotechnology* 19: 316-317 (2001).

Weissleder, et al., "Cell-specific targeting of nanoparticles by multivalent attachment of small molecules" *Nature Biotechnology* 23: 1418-1423 (2005).

Yamamoto, et al., "A Blood-oxygenation-dependent Increase in blood viscosity due to a static magnetic field" *Physics in Medicine and Biology* 49: 3267-3277 (2004).

\* cited by examiner

HEMOGLOBIN CONTRAST IN MAGNETO-MOTIVE OPTICAL DOPPLER TOMOGRAPHY, OPTICAL COHERENCE TOMOGRAPHY, AND ULTRASOUND IMAGING METHODS AND APPARATUS

CROSS-REFERENCE TO RELATED APPLICATIONS

The present application is a continuation of U.S. patent application Ser. No. 13/722,553, filed Dec. 20, 2012; which is a continuation of U.S. patent application Ser. No. 11/874,519, filed Oct. 18, 2007, now U.S. Pat. No. 8,355,776, issued Jan. 15, 2013; which is continuation-in-part of U.S. patent application Ser. No. 11/550,771, filed Oct. 18, 2006, now U.S. Pat. No. 8,036,732, issued Oct. 11, 2011; which is a continuation-in part of U.S. patent application Ser. No. 11/441,824, filed May 26, 2006, now U.S. Pat. No. 7,983,797, issued Jul. 19, 2011; which claims the benefit of U.S. Provisional Application No. 60/685,559, filed on May 27, 2005; and is a continuation-in-part of U.S. patent application Ser. No. 11/784,477, filed Apr. 6, 2007, now U.S. Pat. No. 7,801,590, issued Sep. 21, 2010; which claims the benefit of U.S. Provisional Application No. 60/790,248, filed Apr. 7, 2006. The aforementioned applications are herein incorporated by reference in their entireties.

FUNDING

This invention was supported by funds from the National Institutes of Health (AR47551, EB002495 and EB002021) and the Texas Advanced Technology Program. The U.S. Government may have certain rights in the invention.

BACKGROUND

The present invention relates in general to the art of medical diagnostic imaging and in particular to imaging blood flow using magneto-motive optical Doppler tomography (MM-ODT), Optical Coherence Tomography, or Ultrasound, which combines an externally applied temporally oscillating high-strength magnetic field with ODT, OCT, or Ultrasound to detect erythrocytes moving according to the field gradient.

The accurate determination of location and flow velocity of moving particles in highly scattering media, such as blood flow, is important for medical diagnostics. While the measurements of blood flow in the coronary arteries is an important aspect in diagnosing coronary artery diseases. Numerous non-invasive approaches have been developed using techniques such as Doppler ultrasound, conventional angiography, laser Doppler flowmetry and magnetic resonance angiography.

One common sensing technique involves the use of ultrasound. Using this technique, ultrasound is directed into the body of the patient and tiny particles such as red blood cells, which are suspended in the blood plasma, scatter the ultrasonic energy back towards the receiver or transducer. The transducer then converts the back-scattered ultrasonic energy into an electrical signal that is processed in some known manner to determine the presence of a flow and an estimate of the flow velocity.

Magnetic resonance imaging (MRI) is based on an imaging technique for magnetically exciting nuclear spins in a subject positioned in a static magnetic field by applying a radio-frequency (RF) signal of the Larmor frequency, and reconstructing an image using MR signals induced by the excitation. MRI is widely applied in clinical medicine because of its capability of clearly depicting the slightest tissue of human brain in vivo.

Magnetic resonance angiography (MRA) provides detailed angiographic images of the body in a non-invasive manner. In conventional MRA, which does not use contrast agents, magnetic resonance signal from flowing blood is optimized, while signal from stationary blood or tissue structures is suppressed. In contrast-enhanced MRA, a contrast agent is injected into the blood stream to achieve contrast between flowing blood and stationary tissue.

The commonly known echo planar imaging (EPI) is a rapid MRI technique, which is used to produce tomographic images at high acquisition rates, typically several images per second. Functional magnetic resonance imaging (fMRI) has been found useful in perfusion and/or diffusion studies and in dynamic-contrast studies, etc. However, images obtained in EPI experiments tend to be vulnerable to an artifact known as "ghosting" or "ghost images."

Optical coherence tomography (OCT) is a technology that allows for non-invasive, cross-sectional optical imaging of biological media with high spatial resolution and high sensitivity. OCT is an extension of low-coherence or white-light interferometry, in which a low temporal coherence light source is utilized to obtain precise localization of reflections internal to a probed structure along an optic axis. This technique is extended to enable scanning of the probe beam in the direction perpendicular to the optic axis, building up a two-dimensional reflectivity data set, used to create a cross-sectional gray-scale or false-color image of internal tissue backscatter.

OCT uses the short temporal coherence properties of broadband light to extract structural information from heterogeneous samples such as biologic tissue. OCT has been applied to imaging of biological tissue in vitro and in vivo. Systems and methods for substantially increasing the resolution of OCT and for increasing the information content of OCT images through coherent signal processing of the OCT interferogram data have been developed to provide cellular resolution (i.e., in the order of 5 micrometers). During the past decade, numerous advancements in OCT have been reported including real-time imaging speeds.

In diagnostic procedures utilizing OCT, it would also be desirable to monitor the flow of blood and/or other fluids, for example, to detect peripheral blood perfusion, to measure patency in small vessels, and to evaluate tissue necrosis. Another significant application would be in retinal perfusion analysis. Accordingly, it would be advantageous to combine Doppler flow monitoring with the above micron-scale resolution OCT imaging in tissue.

Conventional OCT imaging primarily utilizes a single backscattering feature to display intensity images. Functional OCT techniques process the backscattered light to provide additional information on birefringence, and flow properties. (See for example, Kemp N J, Park J, Zaatar H N, Rylander H G, Milner T E, High-sensitivity determination of birefringence in turbid media with enhanced polarization-sensitive optical coherence tomography, Journal of the Optical Society of America A: Optics Image Science and Vision 2005, 22(3):552-560; Dave D P, Akkin T, Milner T E, Polarization-maintaining fiber-based optical low-coherence reflectometer for characterization and ranging of birefringence, Optics Letters 2003, 28(19):1775-1777; Rylander C G, Dave D P, Akkin T, Milner T E, Diller K R, Welch M, Quantitative phase-contrast imaging of cells with phase-sensitive optical coherence microscopy, Optics Letters 2004, 29(13):1509-1511; de Boer J F, Milner T E, Ducros M G, Srinivas S M, Nelson J S, Polarization-sensitive optical coherence tomography, Handbook of Optical Coherence Tomography, New York: Marcel Dekker, Inc., 2002, pp 237-274.)

Since the ability to characterize fluid flow velocity using OCT was demonstrated by Wang et al., several phase resolved, real-time optical Doppler tomography (ODT) approaches have been reported. (See for example, Chen Z P, Milner T E, Dave D, Nelson J S, Optical Doppler tomographic imaging of fluid flow velocity in highly scattering media, Optics Letters 1997, 22(1):64-66; Wang X J, Milner T E, Nelson J S.

Optical Doppler tomography (ODT) combines Doppler velocimetry with optical coherence tomography (OCT) for noninvasive location and measurement of particle flow velocity in highly scattering media with micrometer-scale spatial resolution. The principle employed in ODT is very similar to that used in radar, sonar and medical ultrasound. ODT uses a low coherence or broadband light source and optical interferometer to obtain high spatial resolution gating with a high speed scanning device such as a conventional rapid scanning optical delay line (RSOD) to perform fast ranging of microstructure and particle motion detection in biological tissues or other turbid media.

To detect the Doppler frequency shift signal induced by the moving particles, several algorithms and hardware schemes have been developed for ODT. The most straightforward method to determine the frequency shift involves the use of a short time fast Fourier transform (STFFT). However, the sensitivity of this method is mainly dependent on the FFT time window, which limits axial scanning speed and spatial resolution when measuring slowly moving blood flow in small vessels that requires high velocity sensitivity. However, a phase-resolved technique can decouple the Doppler sensitivity and spatial resolution while maintaining high axial scanning speed.

In ODT, the Doppler frequency shift is proportional to the cosine of the angle between output and input scattering directions of the probe beam and the scatterer's flow direction. When the two directions are perpendicular, the Doppler shift is zero. Because a priori knowledge of the Doppler angle is not available, and conventional intensity OCT imaging provides a low contrast image of microvasculature structure, detecting small vessels with slow flow rates is difficult. However, the Doppler angle can be estimated by combining Doppler shift and Doppler bandwidth measurements. (See for example, Piao D Q, Zhu Q, Quantifying Doppler Angle and Mapping Flow Velocity by a Combination of Doppler-shift and Doppler-bandwidth Measurements in Optical Doppler Tomography, *Applied Optics*, 2003, 42(25): 5158-5166, and U.S. Pat. No. 5,991,697 describe a method and apparatus for Optical Doppler Tomographic imaging of a fluid flow in a highly scattering medium comprising the steps of scanning a fluid flow sample with an optical source of at least partially coherent radiation through an interferometer, which is incorporated herein by reference).

The ability to locate precisely the microvasculature is important for diagnostics and treatments requiring characterization of blood flow. Recently, several efforts to increase blood flow contrast mechanisms have been reported including protein microspheres incorporating nanoparticles into their shells, plasmon-resonant gold nanoshells, and use of magnetically susceptible micrometer sized particles with an externally applied magnetic field. (See for example, Lee T M, Oldenburg A L, Sitafalwalla S, Marks D L, Luo W, Toublan F J J, Suslick K S, Boppart S A, Engineered microsphere contrast agents for optical coherence tomography, *Optics Letters,* 2003, 28(17): 1546-1548; Loo C, Lin A, Hirsch L, Lee M H, Barton J, Halas N, West J, Drezek R. Nanoshell-enabled photonics-based imaging and therapy of cancer. *Technology in Cancer Research & Treatment,* 2004; 3(1): 33-40; and Oldenburg A L, Gunther J R, Boppart S A, Imaging magnetically labeled cells with magnetomotive optical coherence tomography, *Optics Letters,* 2005, 30(7): 747-749.)

Wang, et al., "Characterization of Fluid Flow Velocity by Optical Doppler Tomography," *Optics Letters*, Vol. 20, No. 11, Jun. 1, 1995, describes an Optical Doppler Tomography system and method which uses optical low coherence reflectrometry in combination with the Doppler effect to measure axial profiles of fluid flow velocity in a sample. A disadvantage of the Wang system is that it does not provide a method to determine direction of flow within the sample and also does not provide a method for generating a two-dimensional color image of the sample indicating the flow velocity and directions within the image.

The use of an externally applied field to move magnetically susceptible particles in tissue has been termed magneto-motive OCT (MM-OCT). Functional magnetic resonance imaging (fMRI) detects deoxyhemoglobin which is a paramagnetic molecule. However, the paramagnetic susceptibility of human tissue is very low compared to other biocompatible agents such as ferumoxides (nanometer sized iron oxide particles). Therefore, it was believed that, other than differentiating relaxation times (T2) between oxygenated and deoxygenated blood, the magnetic field strength required to produce a retarding force on blood flow was well above that of current imaging fields. (See also, for example, Schenck J F., Physical interactions of static magnetic fields with living tissues, Progress in Biophysics and Molecular Biology 2005, 87(2-3):185-204; and Taylor D S, Coryell, C. D., Magnetic susceptibility of iron in hemoglobin. J. Am. Chem. Soc. 1938, 60:1177-1181.)

SUMMARY OF THE INVENTION

The invention is a method and apparatus of imaging a blood flow, hemoglobin, and/or nanoparticles using optical coherence tomography, which comprises an externally applied temporally oscillating high-strength magnetic field with an optical tomography system to detect hemoglobin and/or nanoparticles.

Another embodiment is an apparatus for imaging blood flow and/or nanoparticles, comprising a magnetomotive optical Doppler tomography (MM-ODT) imaging system Another aspect of the invention is a method for imaging a blood flow, comprising applying a magnetic field to the blood flow, wherein the blood flow comprising a plurality of hemoglobin molecules and/or nanoparticles and wherein the magnetic field interacts with the hemoglobin molecules to cause a change in the blood flow; and detecting the blood flow by detecting the change in the blood flow caused by the interaction with the hemoglobin molecules, wherein the change is detected using a magnetomotive optical Doppler tomography imaging system.

In another embodiment, the invention comprises a solenoid cone-shaped ferrite core with an extensively increased magnetic field strength at the tip of the core. In a further embodiment, the invention comprises focusing the magnetic force on targeted samples.

Another embodiment of the method for imaging a blood flow comprises temporally oscillating the magnetic field.

Another embodiment of the invention is an apparatus for imaging a blood flow comprising a magnetic field generator for applying a magnetic field to the blood flow, wherein the blood flow comprises hemoglobin molecules and/or nanoparticles; and an ultrasound detection system for detecting the blood flow while it is in the presence of the magnetic field.

BRIEF DESCRIPTION OF THE DRAWINGS

The accompanying drawings, which are incorporated in and constitute a part of this specification, illustrate aspects of the methods, apparatuses, and systems and together with the description, serve to explain the principles of the methods, apparatuses, and systems.

FIG. 4A and FIG. 4B are ODT images of 5 mm/s blood flow without and with a 5 Hz magnetic field, respectively. FIG. 4C and FIG. 4D are ODT images of 30 mm/s blood flow without and with a 50 Hz magnetic field, respectively. The Black bar indicates 200 μm, accordingly.

DETAILED DESCRIPTION OF THE INVENTION

Figure 1:
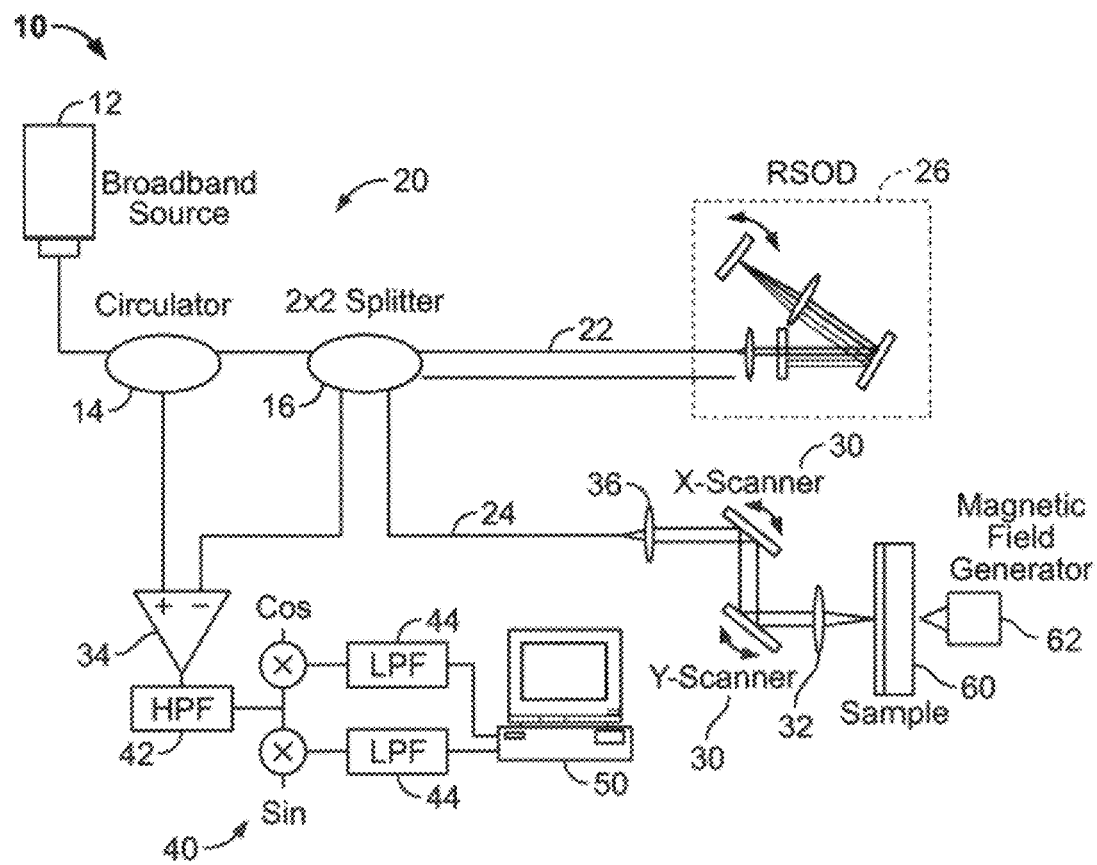
FIG. 1 is a schematic diagram of the MM-ODT system.

The methods, apparatuses, and systems can be understood more readily by reference to the following detailed description of the methods, apparatuses, and systems and the Examples included therein and to the Figures and their previous and following description.

Before the present compounds, compositions, articles, devices, and/or methods are disclosed and described, it is to be understood that these are not limited to specific synthetic methods, specific components, or to particular compositions, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a nanoparticle" includes mixtures of nanoparticles, reference to "a nanoparticle" includes mixtures of two or more such nanoparticles, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally substituted shelled metals" means that shelled metals may or may not be substituted and that the description includes both unsubstituted shelled metals and shelled metals where there is substitution.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human, alternatively, cats, dogs, and other livestock may be used for testing purposes. The term does not denote a particular age or sex. Thus, adult and newborn subjects, as well as fetuses, whether male or female, are intended to be covered.

It is to be understood that nanoparticle and/or hemoglobin may be affected by an external oscillating magnetic field for magneto-motive Optical Coherence Tomographic imaging.

Reference will now be made in detail to exemplary aspects of the systems, methods, apparatuses, and/or compositions, examples of which are illustrated in the accompanying drawings.

Provided herein are methods, compositions and apparatuses for Magneto-Motive Optical Doppler Tomography ("MM-ODT") for improved Doppler imaging of blood flow and/or nanoparticles using an external oscillating magnetic field is described below. By introducing mechanical movement of red blood cells (RBC's) or nanoparticles by a temporally oscillating high-strength magnetic field, MM-ODT allows imaging of blood flow and velocity. The controlled and increased Doppler frequency in MM-ODT provides an investigational tool to study in vivo blood transport, as shown in the article Hemoglobin Contrast in Magneto-motive Optical Doppler Tomography, Opt. Lett. 31, 778-780 (2006), herein incorporated by reference.

The microstructure of the blood flow and flow velocity information are all encoded in the interferogram of a Doppler OCT system. It should be readily apparent to those skilled in the optical arts, that different OCT systems and different OCT information can be used to determine the Doppler frequency shift. It is not intended to suggest any limitation as to the scope or functionality with different OCT architectures or optical information used with an oscillating magnetic field, such as time domain Doppler OCT and spectral domain Doppler OCT. Time domain OCT requires a mechanism that varies the pathlength of light propagating in the reference path of the interferometer, while spectral domain OCT includes swept source OCT and Fourier domain OCT. An example of time-domain Doppler OCT is provided below.

A schematic of the MM-ODT apparatus 10 is shown in FIG. 1. The OCT light source 12 comprises a super luminescent diode, which is used as the low coherence light source, in one embodiment of the invention, where the light source 12 is centered at 1.3 μm with a bandwidth of 90 nm. Alternatively, a tunable laser source in the spectral domain may be used as the light source 12. Light from source 12 is coupled into a single-mode optical fiber based interferometer 20 by circulator 14, where the interferometer 20 can provide 1 mW of optical power at the sample 60. Light is split into a reference arm 22 and sample arm 24 by a 2×2 splitter 16. A rapid-scanning optical delay (RSOD) line 26 is coupled to the reference arm 22. In one embodiment, the rapid-scanning optical delay line 26 is aligned such that no phase modulation is generated when the group phase delay is scanned at ~4 kHz. In the sample arm 24, a collimated beam 36 is redirected to sample 60 by two galvanometers 30 that permit three-dimensional scanning. In one embodiment, the galvanometers can be an X-scanner and a Y-scanner. The sample 60 can be internal or external to the body, where the probe beam is focused by an objective lens 32. In one embodiment, the objective lens 32 yields a 10-μm spot at the focal point. Phase modulation can be generated using an electro-optical waveguide phase modulator, which can produce a carrier frequency (~1 MHz). And the magnetic field generator 62 is in proximity to the sample 60.

A dual-balanced photodetector 34 is coupled to the 2×2 splitter 16 and the circulator 14. The photodetector 34 of an 80 MHz bandwidth reduces the light source noise from the OCT interference signal. A hardware in-phase and quadrature demodulator 40 with high/bandpass filters 42 and low/bandpass filters 44 improves imaging speed. Doppler information was calculated with the Kasai autocorrelation velocity estimator. Labview software 50 (National Instruments, Austin, Tex.) is coupled to the MM-ODT system with a dual processor based multitasking scheme. The maximum frame rate of the MM-ODT system 10 was 16 frames per second for a 400×512 pixel sized image. The Doppler frequency shift can be determined with the use of a short time fast Fourier transform (STFFT). Alternatively, a phase-resolved technique can determine the Doppler frequency shift to decouple the Doppler sensitivity and spatial resolution while maintaining high axial scanning speed. Alternatively, differential phase optical coherence tomography (OCT) or spectral domain phase-sensitive OCT can be used to determine the Doppler frequency shift, as readily determined by one skilled in the optical arts.

Figure 2:
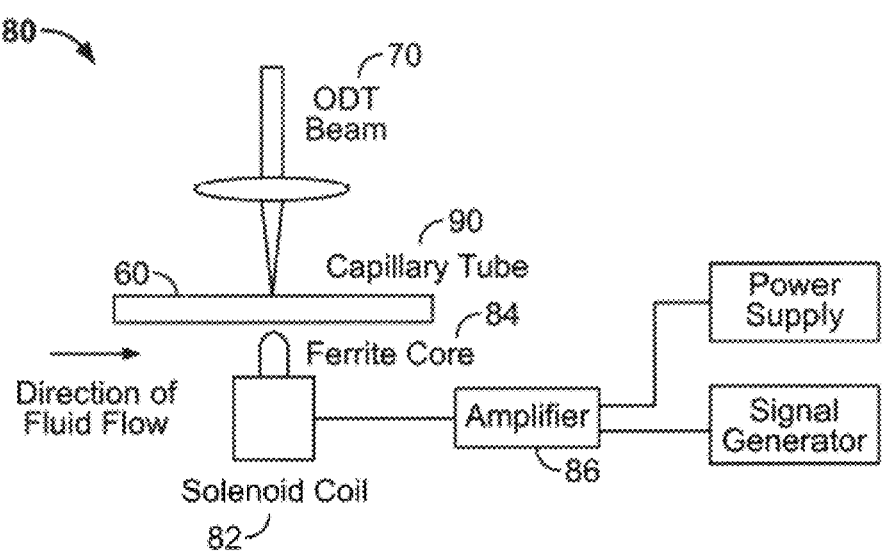
FIG. 2 is a schematic diagram of the probe beam, flow sample and solenoid coil.
Figure 3A:
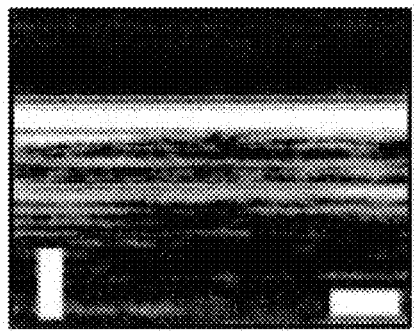
FIGS. 3A and 3B are OCT and ODT images of a stationary turbid solution without an external magnetic field, respectively.
Figure 3B:
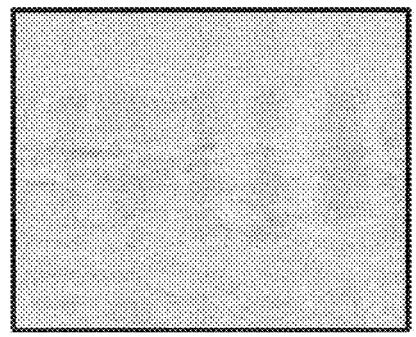
Figure 3C:
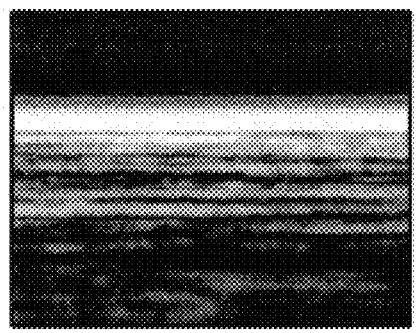
FIG. 3C and FIG. 3D are OCT and ODT images with a 50 Hz magnetic field, respectively. The white bar represents 200 μm, accordingly.
Figure 3D:
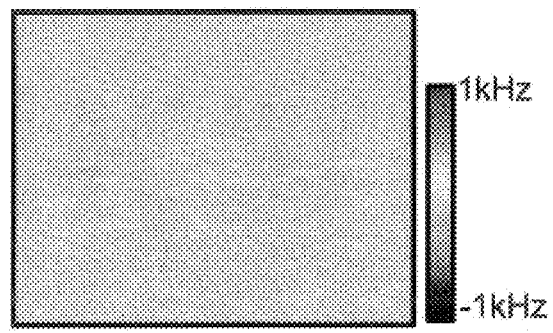

FIG. 2 shows an example of the magnetic field generator 80 with a capillary tube 90. The magnetic field generator 80 includes a solenoid coil 82 (Ledex 4EF) with a cone-shaped ferrite core 84 at the center and driven by a current amplifier 86 supplying up to 960 W of power. The magnetic field generator 80 can be placed underneath the sample 60 during MM-ODT imaging. The combination of the ferrite core 84 and solenoid coil 82 using a high power operation dramatically increases the magnetic field strength ($B_{max}$ 0.14 Tesla) at the tip of the core 82 and also focuses the magnetic force on the targeted samples 60. The sinusoidal current can vary the magnetic force applied to the capillary tube 90 in order to introduce movement of magnetic fluids, which include red blood cells that contain hemoglobin. In one embodiment, the probe beam is oriented parallel to the gradient of the magnetic field's strength.

The material parameter characterizing magnetic materials, including biological tissue, is the magnetic volume susceptibility, $\chi$. Magnetic volume susceptibility is dimensionless in SI units and is defined by the equation M=$\chi$H, where M is the magnetization at the point in question and H is the local density of the magnetic field strength. Hemoglobin's high iron content, due to four Fe atoms in each hemoglobin molecule, and the large concentration of hemoglobin in human red blood cells allow Hemoglobin magneto-motive effects in biological tissue. The magnetic volume susceptibility of the hemoglobin molecule consists of a paramagnetic component due to the electron spins of the four iron atoms. The paramagnetic susceptibility is given by the Curie Law, $$\chi = \frac{\mu_o N_p (\mu_{eff}^2 \mu_B^2)}{3kT} \tag{1}$$

where $\mu_o$ is permeability of free space and has the value $4\pi \times 10^7$ H/m, $N_p$ is the volume density of paramagnetic iron atoms in hemoglobin, $N_p$=4.97×10$^{25}$ iron atoms/m$^3$, $\mu_{eff}$ is the effective number of Bohr magnetons per atom reported as 5.35, and the Bohr magneton, $\mu_B$=9.274×10$^{-24}$ J/T, and Boltzmann's constant, k=1.38×10$^{-23}$ J/K, and T is the absolute temperature (K). The calculated susceptibility of a RBC is about $11 \times 10^{-6}$ assuming a 90% concentration of hemoglobin per RBC. The calculated susceptibility of a RBC is dependent on the oxygenation of the hemoglobin. The calculations can be adjusted accordingly, depending on the oxygenation of the RBC, which can be measured by known techniques.

A RBC placed in a magnetic field gradient experiences forces and torques that tend to position and align it with respect to the field's direction. The magnetic force, in the direction of the probing light z, is given by $$F_i = m_{RBC} \frac{\delta^2 z(t)}{dt^2} = \frac{\delta U}{\delta z} = \frac{\Delta \chi V}{\mu_o} B \frac{\delta B}{\delta z}, \quad (2)$$

where V is the particle volume, B is the magnitude of the magnetic flux density, and $\Delta \chi$ is the difference between the susceptibility of the particle and the surrounding medium. The displacement [z(t)] of an RBC driven by a time varying magnetic flux density can be included in the analytic OCT fringe expression, $I_f$, $$I_f = 2\sqrt{I_R I_S} \exp\left[i\left(2\pi f_o t + \frac{4\pi z(t)}{\lambda_o} z(t)\right)\right], \quad (3)$$

where $I_R$ and $I_S$ are the back scattered intensities from the reference and sample arms, respectively, $f_o$ is the fringe carrier frequency, $\lambda_o$ is the center wavelength of the light source, and z(t) is the RBC displacement. Integration of all forces (magnetic, elastic, and viscous) on the RBC gives a steady state displacement, $z(t) = A \cos(4\pi f_m t)$ where A is a constant in units of length and $f_m$ is the modulation frequency of the magnetic flux density. In free space, the displacement, z(t), is dominated a constant acceleration which can be, however, ignored in confined models (i.e. blood vessel or capillary tube) with assumptions that, first, the probing area is much smaller than magnetic field area, and that secondly probing time starts after steady states of inner pressures. Expansion of the right-hand side of Eq. (3) using Bessel functions gives $$I_f \alpha 2\sqrt{I_R I_S} \quad (4)$$
$$\left(\sum_{k=0}^{\infty} (J_k(m) \exp(ik4\pi f_m t)) + \sum_{k=0}^{\infty} ((-1)^k J_k(m) \exp(-ik4p f_m t))\right)$$
$$\exp(i2\pi f_o t)$$

where $J_k(m)$ is the Bessel function of the first kind of order k for argument m which is $4\pi A/\lambda_o$. The amplitude of the $k^{th}$ sideband is proportional to $J_k(m)$. In coherent detection, the fraction of optical power transferred into each of the first order sidebands is $(J_1(m))^2$, and the fraction of optical power that remains in the carrier is $(J_o(m))^2$.

EXAMPLES

The following examples are put forth so as to provide those of ordinary skill in the art with a complete disclosure and description of how the compositions, compositions, articles, devices, systems, and/or methods claimed herein are made and evaluated, and are intended to be purely exemplary and are not intended to limit the scope of compositions, compositions, articles, devices, systems, and/or methods. Efforts have been made to ensure accuracy with respect to numbers (e.g., amounts, temperature, etc.), but some errors and deviations should be accounted for. Unless indicated otherwise, parts are parts by weight, temperature is in degrees Celsius or is at ambient temperature, and pressure is at or near atmospheric.

Example 1

MM-ODT Imaging of the Doppler Shift of Hemoglobin by Applying an Oscillating Magnetic Field to a Moving Blood Sample M-mode OCT/ODT images of a capillary glass tube filled with a stationary turbid solution with and without an external magnetic field as a control sample were recorded, as shown in FIGS. 3-4. A 750 µm-inner diameter glass capillary tube 200 was placed perpendicularly to the probing beam 70, as shown in FIG. 2. Fluids used for flow studies were injected through the tube at a constant flow rate controlled by a dual-syringe pump (Harvard Apparatus 11 Plus, Holliston, Mass.) with ±0.5% flow rate accuracy. The turbid solution was a mixture of deionized water and 0.5-gm latex microspheres ($\mu_s$=5 mm$^{-1}$). The magnetic flux density and its frequency were approximately 0.14 T and 50 Hz, respectively. M-mode OCT/ODT images were acquired for 100 ms per frame. FIGS. 3a and 3b show M-mode OCT and ODT images without any external magnetic field, respectively. The ODT image in FIG. 3b contains small random phase fluctuations due to ambient vibration through the optical path. FIGS. 3c and 3d show M-mode OCT and ODT images with a 50 Hz external magnetic field, respectively. No distinguishable Doppler shift could be observed in the ODT image FIG. 3d indicating no interaction between the external magnetic field and the moving microspheres.

Deoxygenated blood was extracted from the vein of a human male's left arm, and diluted with saline. During preparation, blood was not exposed directly to air so as to remain deoxygenated. To simulate flow, blood was injected through the capillary tube 200 by a syringe pump at a relatively constant flow rate. As FIG. 4 shows, the oscillating Doppler frequency shift, resulting from RBC movement, could be observed at two different flow rates (5 and 30 mm/s). Because the flow direction was nearly perpendicular to the probing beam no significant Doppler frequency shift was distinguishable at the 5 mm/s flow rate FIG. 4a without any external magnetic field. In the case of the high blood flow rate of 30 mm/s, as shown at FIG. 4c, the Doppler frequency shift caused by the blood flow could be observed. And for maximum contrast enhancement, the probe beam can be directed parallel to the gradient of the magnetic field's strength. However, application of a 50 Hz magnetic field increased the Doppler contrast of blood at both the slow and fast flow rates as shown at FIGS. 4b and 4d. The high flow rate of 30 mm/s gives a higher contrast image than the low flow rate image, but the Doppler frequency shift of the former as a function of depth is less homogeneous than the latter, which is indicative of perturbation by blood flow. The same blood was diluted to 5% hematocrit (HCT), but no RBC movement could be observed below 8% HCT.

Figure 4A:
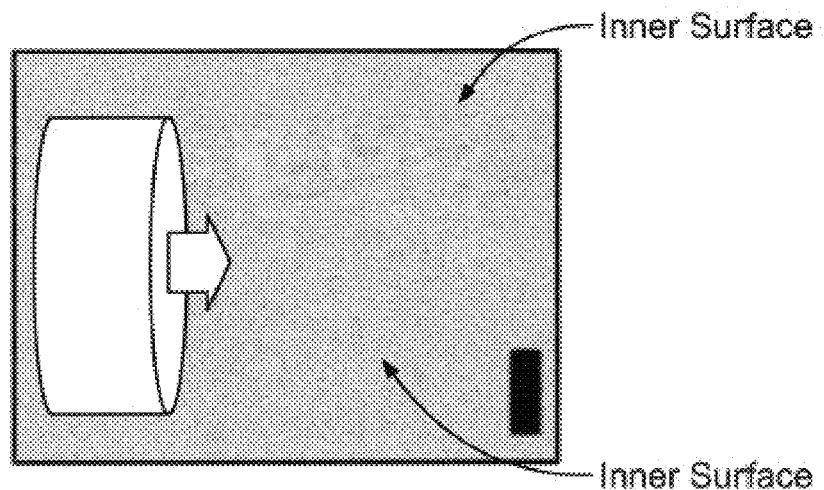
FIGS. 4A-4D are M-mode ODT images of the diluted deoxygenated blood flow (18% hematocrit) without and with an external magnetic field.
Figure 4B:
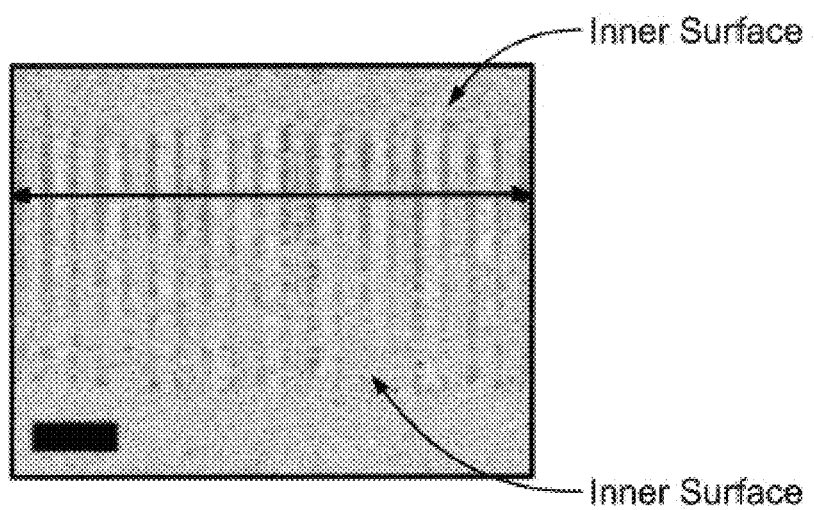
Figure 4C:
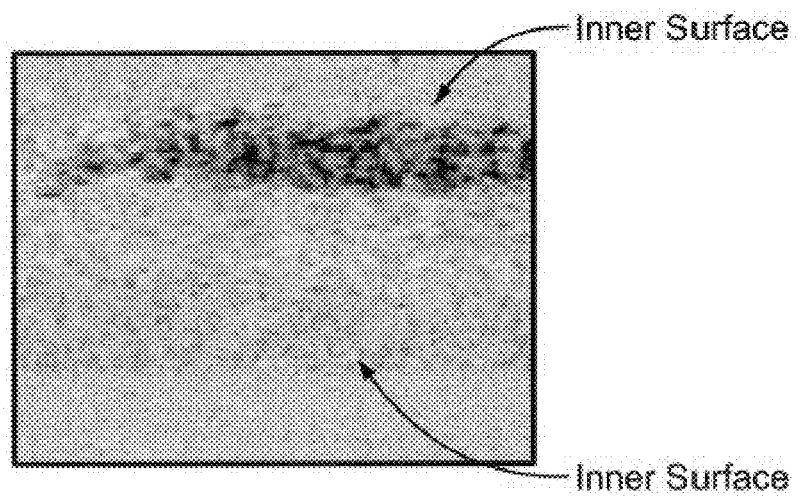
Figure 4D:
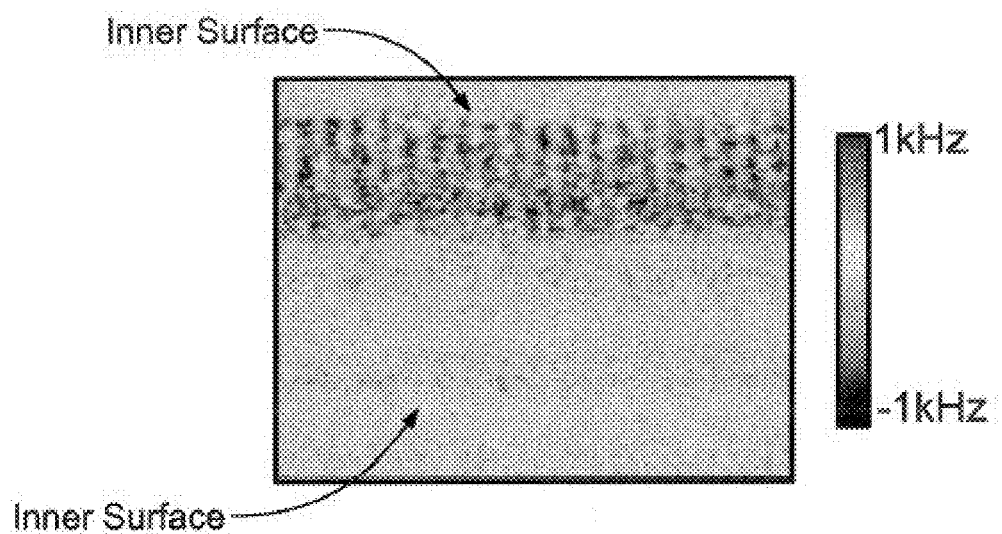
Figure 5A:
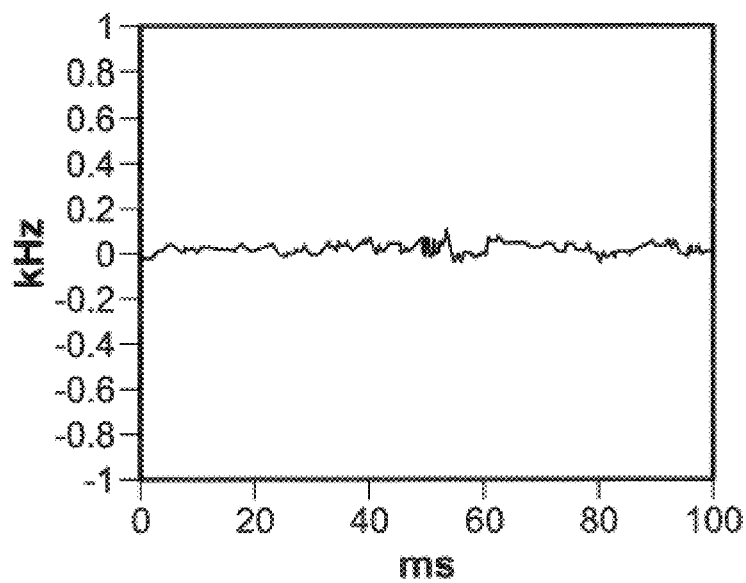
FIG. 5A and FIG. 5B are the Doppler frequency shift profiles without an external magnetic field, and with a 50 Hz magnetic field, respectively.

Doppler frequency shift profiles were calculated from the ODT images by averaging 20 lines at a selected depth indicated by horizontal arrows, as shown in FIGS. 4a and 4b. FIG. 5a indicates no significant Doppler frequency shift over a 100 ms time period, whereas FIG. 5b displays ±200 to 300 Hz Doppler frequency shifts oscillating 20 times over 100 ms (200 Hz).

Figure 5B:
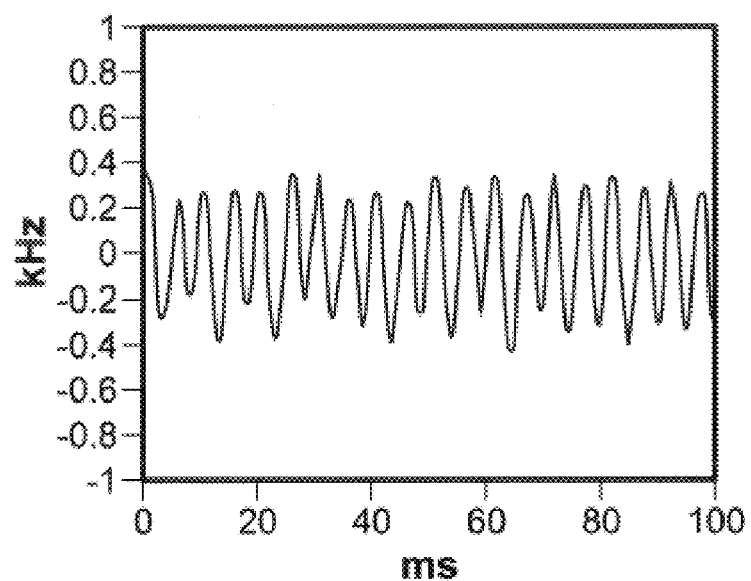

The Doppler frequency shift indicates that RBC's physically move into and away from the incident light while passing through the external magnetic field depending on whether their magnetic properties are paramagnetic or diamagnetic, as shown in FIG. 4, and that the 200 Hz oscillation of the Doppler frequency shift correlates with the 50 Hz magnetic field, as shown in FIG. 5. Frequencies 4 times higher than that of the external magnetic field ($f_m$) can be observed. According to Eq. 2, the frequency of the force on paramagnetic targets was twice that of the magnetic flux density; therefore, a 50 Hz B field displaces the targets at 100 Hz. Although the fringe signal (Eq. 4) contains harmonics at frequency ($2f_m$), the modulation frequency, $f_m$, was set so that the second-order sideband ($4f_m$) was dominant as shown in FIG. 5b. The particle motion cannot be described as a pure sinusoidal function even if the modulated magnetic field is sinusoidal, due to the numerous forces that contribute to the motion within the field such as gravity, concentration gradient, and colloidal dispersion.

The invention is a new investigational tool to study in vivo blood transport and the first implementation of MM-ODT for improved Doppler imaging of blood flow using an external oscillating magnetic field introducing a mechanical movement of RBC's during blood flow by a temporally oscillating high-strength magnetic field. MM-ODT to allow imaging of tissue function in a manner similar to functional magnetic resonance images (f-MRI) of deoxygenated blood in organs, when the sample arm of the MM-ODT system is coupled to a probe (not shown). Such probes are generally known in the arts, such as endoscopic probes, catheter probes, and the like.

Alternatively, the MM-ODT can be used for Port-Wine vessel mapping and Skin Cancer vessel mapping. The MM-ODT can be used to detect blood vessel location and size for cancer and port-wine stains, since these conditions are characterized by blood vessel growth and increases in hemoglobin content. Accordingly, other blood vessel detection for tissue abnormality identification can be envisioned with this invention. Generally, the MM-ODT can be used wherever blood flow detection is necessary in operations, chemotherapy, hemodialysis, and the like.

Figure 6:
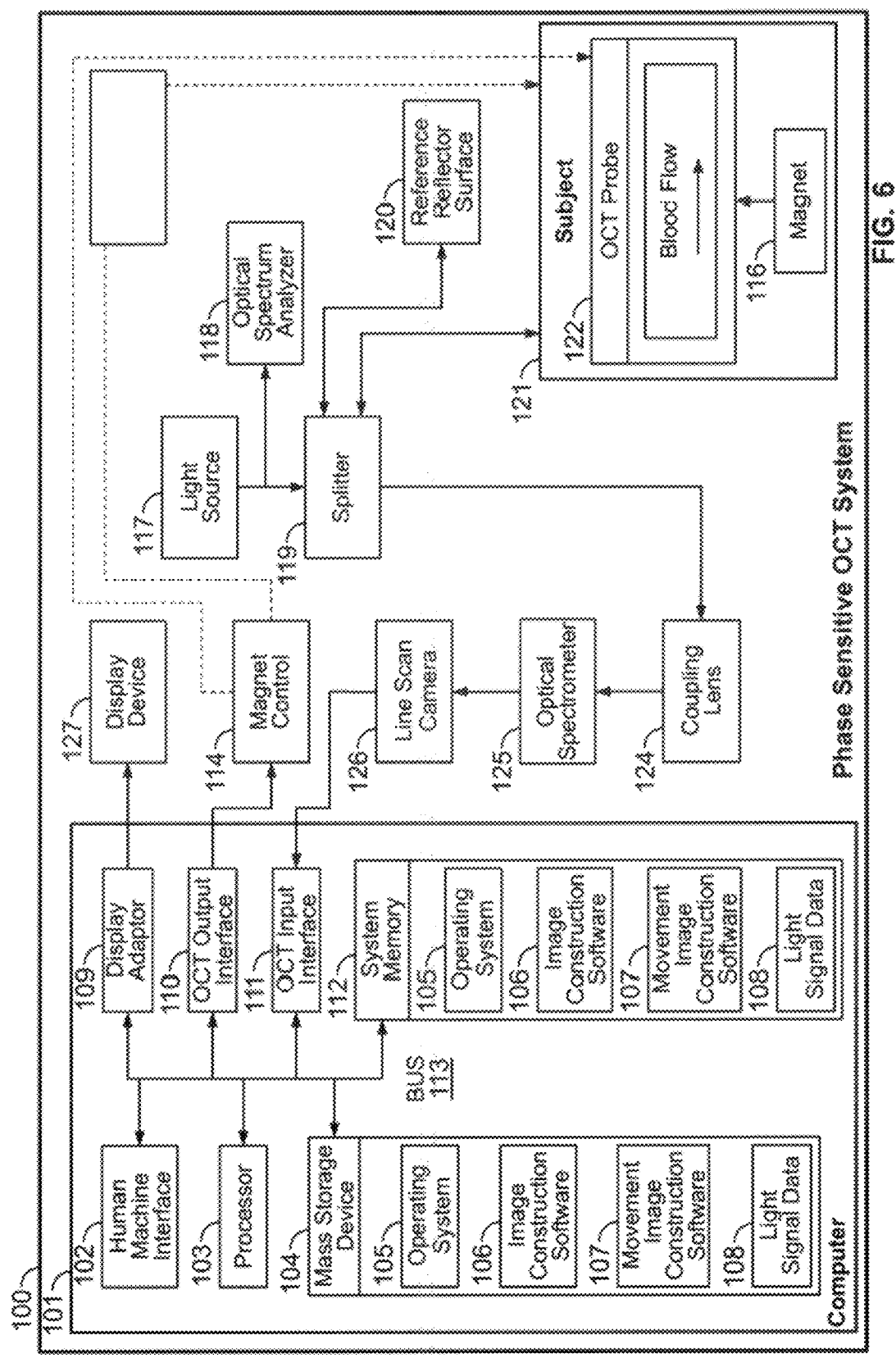
FIG. 6 is a block diagram illustrating an exemplary phase sensitive OCT system.

A spectral domain phase sensitive OCT system 100 can be used to image the blood flow and determine velocity information, when an oscillating magnetic field is applied to the blood flow, as shown in FIG. 6. Spectral domain phase sensitive OCT generally uses a broadband light source (in a general interferometric setup, where the mirror in the reference typically does not move or does not require a rapid scanning delay line. A spectral interferogram is detected, in which each A-scan is entirely encoded. A Fourier transformation of the A-scan and velocity distribution of the blood flow can be extracted by known methods. Spectral domain OCT can be generally understood under U.S. Pat. No. 5,991,697, which describes how to measure the Doppler shift. In spectral domain Doppler OCT, the blood flow profile is the envelope of a calculated A-scan through Fourier transformation on the spectral interferogram. Velocity information is encoded in the rate of phase change of the interferogram. The Doppler velocity can be extracted by measuring the phase shift between two successive calculated A-scans in spectral domain Doppler OCT and the time between recording successive A-scans This OCT system 100 is only an example of one OCT imaging modality which can be used to image blood flow with a temporally oscillating magnetic field, and is not intended to suggest any limitation on the scope of OCT architectures applicable to the invention. Generally, the OCT system 100 includes a general-purpose computing device in the form of a computer 101 and includes a magnet control 114 and a magnet 116.

Light energy is generated by a light source 117. The light source 117 can be a broadband laser light source coupled into optical fiber emitting light energy over a broad range of optical frequencies. The wavelength range can be from about 400 nanometers to about 1600 nanometers. Longer wavelengths (>800 nm) can be used for deeper scanning Preferably, the light source emits light having a wavelength near the infrared spectrum to identify hemoglobin for OCT imaging, and the magnet 116 places hemoglobin in motion and increases optical scattering of the hemoglobin. The light energy can be emitted over a multiplicity of optical wavelengths, frequencies, and pulse durations to achieve OCT imaging. As used herein, optical fiber can refer to glass or plastic wire or fiber. Optical fiber is indicated on FIG. 6 as lines connecting the various blocks of the figures. Where light energy is described as "passing," "traveling," "returning," "directed," or similar movement, such movement can be via optical fiber.

A fraction of the generated light energy passes from the light source 117 into an optical spectrum analyzer 118. The optical spectrum analyzer 118 measures optical frequency as the light energy is emitted from the light source 117 as a function of time. The optical spectrum analyzer 118 samples a portion of the light emitted by the light source 117. The optical spectrum analyzer 118 monitors the power spectral density of light entering the splitter 119. The remaining fraction of light energy from the light source 117 passes into a splitter 119. The splitter 119 can be a device with four ports, with Port 1 allowing light energy to enter the splitter 119. Ports 2 and 3 allow light energy to leave and re-enter the splitter 119 to the reference reflector 120 and OCT probe 122, respectively. Port 4 allows light energy to leave the splitter 119 to coupling lens 124. The splitter 119 couples the light into Port 1. The splitter 119 divides the light according to a pre-determined split ratio selected by a user. For example, the split ratio can be 50/50 wherein half of the light energy entering the splitter 119 at Port 1 exits the splitter 119 through Port 2 and half exits the splitter 119 through Port 3. In another example, the split ratio can be 60/40 wherein 60% of the light energy passes through Port 2 and 40% of the light energy passes through Port 3.

A fraction of the light energy (determined by the split ratio) that exits the splitter 119 through Port 2 travels to a reference reflector surface 120. The light energy is reflected from the reference reflector surface 120 back to the splitter 119 into Port 2. The reference reflector 120 can be a planar metallic mirror or a multilayer dielectric reflector with a specified spectral amplitude/phase reflectivity. The remaining fraction of light that entered splitter 119 through Port 1 exits splitter 119 through Port 3 and enters an OCT probe 122. The OCT probe 122 can be a turbine-type catheter as described in Patent Cooperation Treaty application PCT/US04/12773 filed Apr. 23, 2004 which claims priority to U.S. provisional application 60/466,215 filed Apr. 28, 2003, each herein incorporated by reference for the methods, apparatuses and systems taught therein. The OCT probe 122 can be located within a subject 121 to allow light reflection off of subject's 121 blood flow.

The light energy that entered OCT probe 122 is reflected off of the blood flow of subject 121 once an oscillating magnetic field has been temporally applied by magnet 116.

The reflected light energy passes back through the OCT probe 122 into the splitter 119 via Port 3. The reflected light energy that is returned into Port 2 and Port 3 of the splitter 119 recombines and interferes according to the split ratio. The light recombines either constructively or destructively, depending on the difference of pathlengths. A series of constructive and destructive combinations of reflected light create an interferogram (a plot of detector response as a function of optical path length difference). Each reflecting layer from the subject 121 and the blood flow will generate an interferogram. The splitter 119 can recombine light energy that is returned through Port 2 and Port 3 so that the light energies interfere. The light energy is recombined in the reverse of the split ratio. For example, if a 60/40 split ratio, only 40% of the light energy returned through Port 2 and 60% of the light energy returned through Port 3 would be recombined. The recombined reflected light energy is directed out Port 4 of the splitter 119 into a coupling lens 124. The coupling lens 124 receives light from the output of the splitter 119 and sets the beam etendue (beam diameter and divergence) to match that of the optical spectrometer 125. The coupling lens 124 couples the light into an optical spectrometer 125. The optical spectrometer 125 can divide the recombined reflected light energy light into different optical frequencies and direct them to different points in space which are detected by a line scan camera 126. The line scan camera 126 performs light to electrical transduction resulting in digital light signal data 108. The digital light signal data 108 is transferred into the computer 101 via the OCT input interface 111. Interface between the line scan camera 126 and computer 101 can be a Universal Serial Bus (USB), or the like. The digital light signal data 108 can be stored in the mass storage device 104 or system memory 112 and utilized by the image construction software 106 and the Labview image construction software 107.

The image construction software 106 can generate an image of the blood flow of subject 121 from the light signal data 108, by receiving light signal data 108 generating amplitude and phase data. The amplitude and phase data (optical path length difference ($c\tau$) or optical time-delay ($\tau$)) can be separated into discrete channels and a plot of intensity vs. depth (or amplitude vs. depth) can be generated for each channel. Such plot is known as an A-scan, where the composition of all the A-scans can comprise one image. And movement image construction software 107 generates an image of the movement of the hemoglobin from the light signal data 108. The movement image construction software 107 receives light signal data 108 for at least two successive sweeps of the light source 117 and the light source performs a Fourier transform on the light signal data 108 generating amplitude and phase data.

Figure 7:
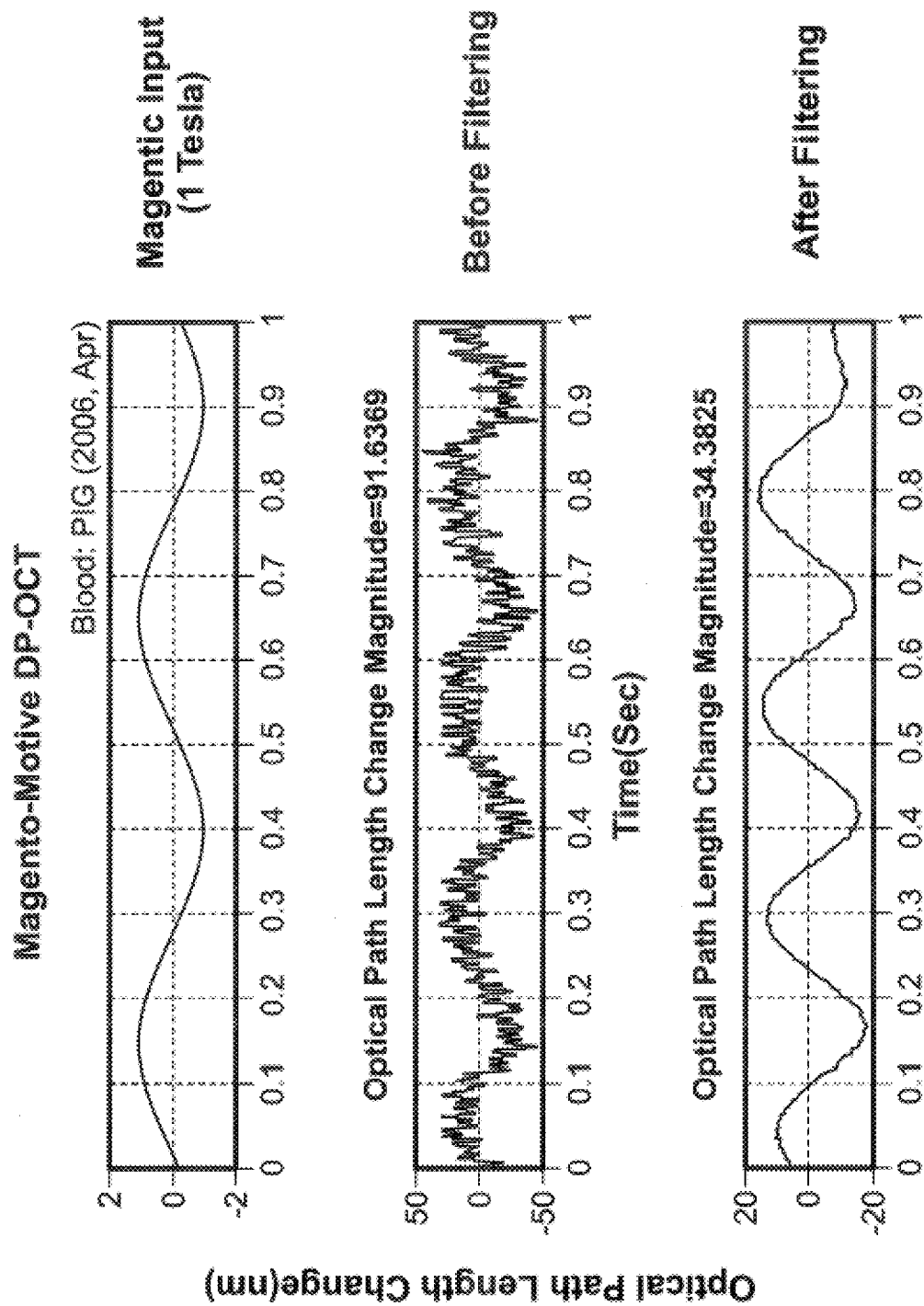
FIG. 7 is a graph of the optical path length change in the DP-OCT system.

Optionally, additional information can be extracted from the light signal data to generate additional images. The light signal data can be further processed to generate a Stokes parameter polarimetric image when used in conjunction with polarization detectors and polarizing splitters to extract polarization data from the light signal 108, as readily known to one skilled in the art of optical coherence tomography. The differential phase OCT image data is shown in FIG. 7, indicating the optical path difference with time variation of the magnetic field magnitude. Signal processing filters can be utilized to reduce the noise of the optical pathlength signal.

Alternatively, the phase sensitive OCT system 100 can be configured for swept source OCT, which is a different type of spectral domain OCT. In swept source OCT, a tunable laser source replaces the broadband laser light source 117. The scanning rate can be at wavelengths of 800 nm-1500 nm. Also, the reference reflector surface 120 is in-line with sample path 120. The optical spectrometer 125 and line scan camera 126 are replaced with a general photodetector. In this configuration, an optical clock is used to trigger acquisition of the signal produced by the photodetector. The optical clock provides a set of uniformly spaced clock pulses with fixed intervals of optical frequency and at least one reference pulse. The fixed intervals of optical frequency are configured and specified in the optical clock to give a uniform train of pulses. The at least one reference pulse generated by the optical clock is utilized to provide a reference optical frequency or a trigger pulse. For example, the first reference pulse generated by the optical clock can correspond to an absorption line in a gas cell (e.g., Hydrogen Fluoride or Hydrogen Bromide). In this case the gas absorption line has a known optical frequency. The well-known absorption fingerprint bands in the HF gas cell result in a reduced detected intensity in the light transmitted through the gas cell, and as such provide a metric on the absolute lasing wavelength at the digitized samples of the photodetector signal. The digitized sample number or sampling time scale can thus be converted to absolute wavelength at one or more samples, depending on the number of absorption lines. The detected wavemeter photocurrent signal and the detected gas cell photocurrent signal are combined in the digitizer to provide the relationship between the sample number or sampling time and lasing wavelength throughout the entire sweep. The detected photocurrent signal from the gas cell is digitized concurrently with the OCT interferogram and correlated with the known HF fingerprint to determine the wavenumber bias ($k_o$) of the swept source laser. Knowledge of wavenumber bias ($k_o$) allows accurate determination of the absolute wavenumber of each digitized sample throughout the spectral sweep, effectively removing any wavenumber offsets and/or phase instabilities in the laser source, wavemeter and sampling electronics. Knowledge of the magnitude of the fixed intervals and the optical frequency of at least one clock pulse provides knowledge of the optical frequency of every clock pulse provided by the optical clock.

In one configuration of an optical clock, an optical comb source may be used. An optical comb source provides light with a power spectral density that is uniformly spaced in the optical frequency domain at a fixed, known, and stable optical frequency interval. By mixing or interfering light emitted by the tunable laser source with light emitted by the optical clock, the interference signal provides an optical clock pulse. In this configuration, the instantaneous spectral linewidth of the tunable laser source is less than the optical frequency interval of the optical comb source. In addition, at least one of the clock pulses generated by the optical clock is utilized to provide a reference optical frequency. For example, the first clock pulse generated by the optical clock can correspond to an absorption line in a gas cell (e.g., Hydrogen Fluoride). In this case the gas absorption line has a known optical frequency. Knowledge of the magnitude of the fixed intervals and the optical frequency of at least one clock pulse provides knowledge of the optical frequency of every clock pulse provided by the optical clock.

In another configuration of an optical clock, a Fabry-Perot interferometer is used. In this configuration, light emitted by the tunable laser source is input into the Fabry-Perot interferometer. The light transmitted through the Fabry-Perot interferometer provides light with a power spectral density that is uniformly spaced in the optical frequency domain at a fixed optical frequency interval. In this configuration, the instantaneous spectral linewidth of the tunable laser source is less than the optical frequency interval of Fabry-Perot interferometer. In addition, at least one of the clock pulses generated by the optical clock is utilized to provide a reference optical frequency. For example, the first clock pulse generated by the optical clock can correspond to an absorption line in a gas cell (e.g., Hydrogen Fluoride). In this case the gas absorption line has a known optical frequency. Knowledge of the magnitude of the fixed intervals and the optical frequency of at least one clock pulse provides knowledge of the optical frequency of every clock pulse provided by the optical clock.

In another embodiment, an enhanced detection of cancer with ultrasound imaging 200 is provided. Ultrasonography is the ultrasound-based diagnostic imaging technique used to visualize muscles and internal organs, their size, structures and any pathological lesions. "Ultrasound" applies to all acoustic energy with a frequency above human hearing (20,000 Hertz or 20 kilohertz). Typical diagnostic sonography scanners operate in the frequency range of 2 to 40 megahertz, hundreds of times greater than this limit. The choice of frequency is a trade-off between the image spatial resolution and penetration depth into the patient, with lower frequencies giving less resolution and greater imaging depth. Doppler ultrasonography uses the Doppler Effect to assess whether blood is moving towards or away from a probe, and its relative velocity. By calculating the frequency shift ($v_D$) of a particular sample volume, for example a jet of blood flow over a heart valve, its speed and direction can be determined and visualized. Ultrasonagraphy and Doppler Ultrasonagraphy can best be understood by S. A. Kana *Introduction to physics in modern medicine*, Taylor & Francis, (2003). The basic physics of the Doppler effect involving acoustic and electromagnetic waves of OCT is similar and many of the signal processing techniques (hardware and software) used to estimate the Doppler shift of ultrasonic and optical coherence tomography signals is analogous.

Figure 8:
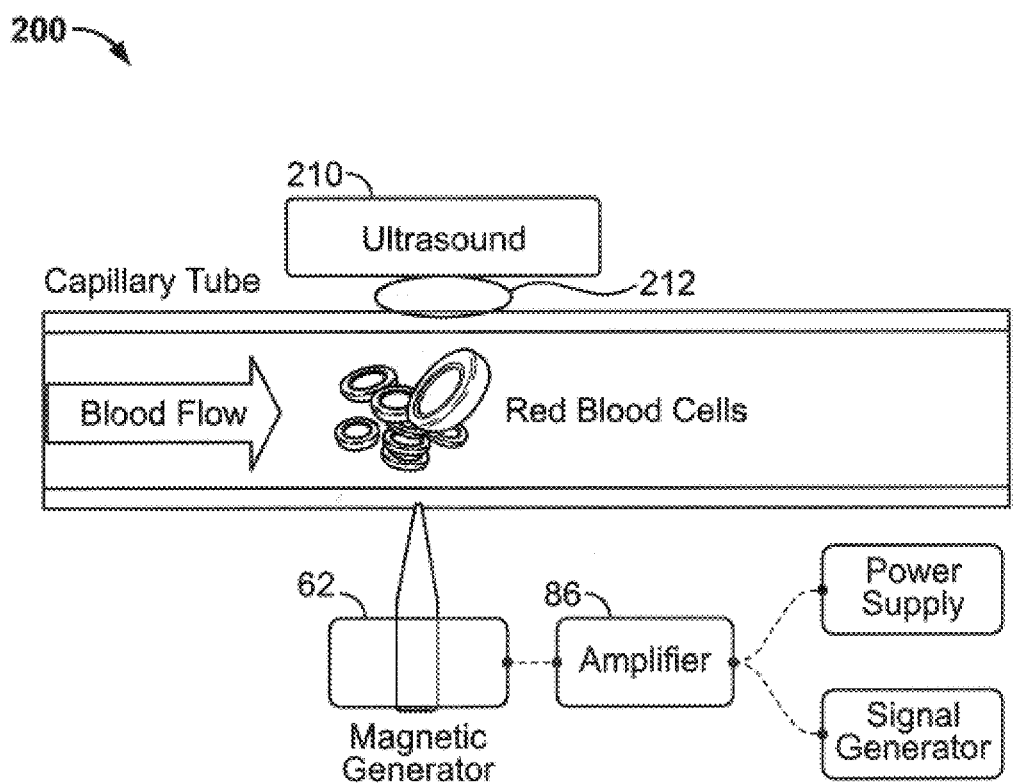
FIG. 8 is a schematic diagram of Magneto Motive Ultrasound for Blood.

In one embodiment of the invention, an ultrasound probe 212 is coupled with the magnetic field generator 100, as shown in FIG. 8. Ultrasound 210 is directed into the body of the patient by known techniques and the moving red blood cells backscatter the ultrasonic energy back towards the transducer of the ultrasound. The oscillating magnetic field generated by the magnetic field generator 62 increases the contrast of the ultrasonic energy 210 received from the red blood cells. The transducer then converts the back-scattered ultrasonic energy 210 into an electrical signal that is processed in some known manner to determine an estimate of the flow. An enhanced ultrasound image is produced, as displayed in FIG. 9.

Figure 9:
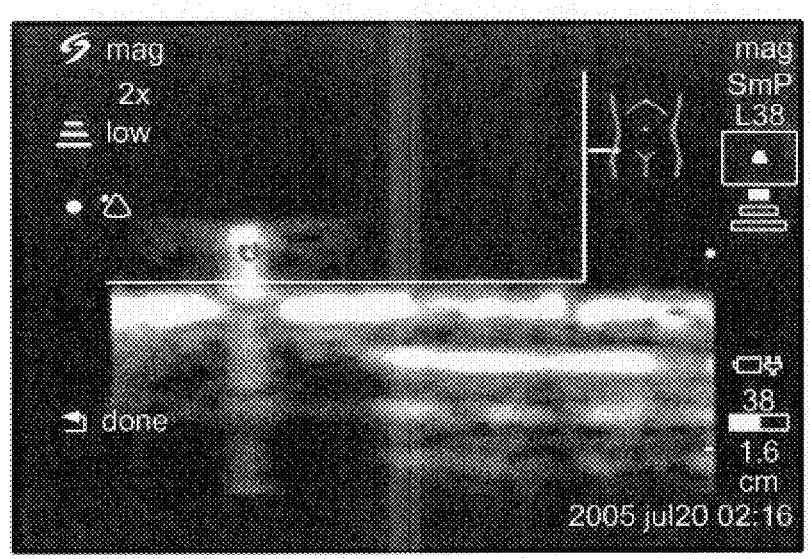
FIG. 9 is an ultrasound image of blood exposed to an oscillating magnetic field.

In one example, a rectal ultrasound probe is coupled with a magnet to evaluate the prostate gland for cancer. Currently, ultrasound is used for prostate cancer screening; however, the approach provides poor sensitivity and specificity. Yet, all cancers are known in the art to be highly vascular, so then the application of the magnetic field by generator 62 coupled with ultrasound enhances the contrast available from the endogenous RBC's in the prostate for cancer detection at an earlier stage. It is generally known in the art that tissues with cancerous cells have enhanced metabolic demand compared to normal tissues, so then cancerous cells have higher oxygen content from hemoglobin and a greater concentration of deoxygenated hemoglobin compared to normal tissues. An exemplary ultrasound image for prostate cancer screening is shown in FIG. 9.

Figure 10:
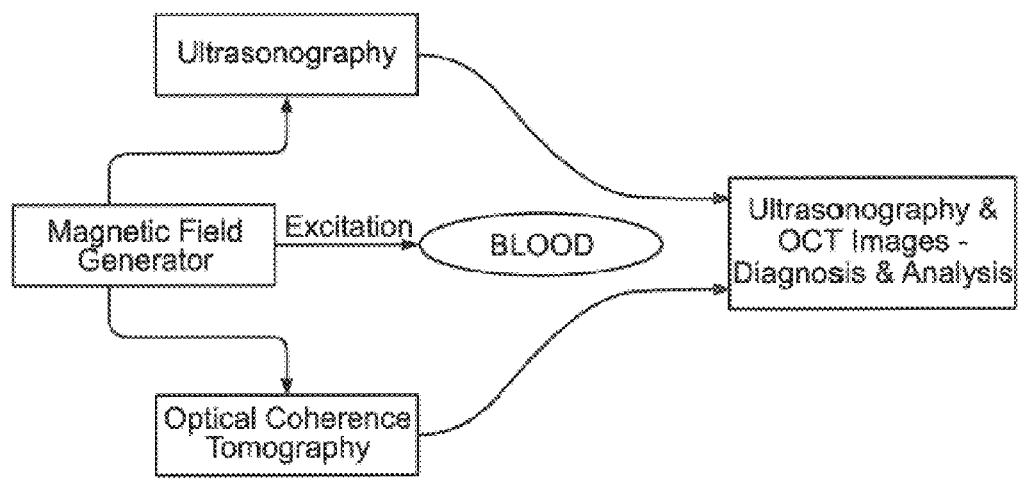
FIG. 10 is a schematic diagram of Ultrasonography and OCT coupled with magnetic field generator.

MM-ODT, OCT, and ultrasound coupled with an oscillating magnetic field all can be used in clinical management of patients who need microvasculature or vasculature monitoring, as shown in FIG. 10. The images could monitor and determine tissue perfusion and viability before, during and after therapeutic procedures. For example, the images could be used to detect oxygenated and deoxygenated blood supply, detect blood vessel location, spatial extent of cancer, vascular tissue abnormality identification, and imaging of port-wine stain. Alternatively, the images could monitor photodynamic therapy or evaluate cranial injuries. While medical applications of the invention have been described, the embodiments of the invention are applicable to any circumstance where image contrast is needed for fluids comprising endogenous metallic compositions. MM-ODT, OCT, and ultrasound can be used in various combinations to detect vascular occurrences.

OCT Imaging Using Nanoparticles

Provided herein are methods, compositions and apparatuses for detecting a cell and/or a metallic composition using optical coherence tomography ("OCT"). By a "cell" is meant one or more cell of, or derived from, a living organism or subject. The cell or cells can be located within a subject or can be located ex vivo. The disclosed methods, compositions and apparatuses for detecting a cell and/or a metallic composition are described herein variously by reference to cell(s), composition(s) and/or metallic composition(s). It will be understood that description of various aspects of the disclosed methods, compositions and apparatuses by reference to one or a subset of cell(s), composition(s) or metallic composition(s) constitutes description of that aspect of the disclosed methods, compositions and apparatuses to the non-referenced cell(s), composition(s) and metallic composition(s), unless the context clearly indicates otherwise.

An exemplary method for detecting a cell comprises applying a magnetic field to the cell. A cell can comprise a cellular membrane and a metallic composition. Optionally, the metallic composition is a metallic nanoparticle that was administered to the subject or otherwise brought into contact with the cell. Optionally, the metallic composition is hemoglobin, as discussed previously.

The metallic composition can be located within the cell, including in the cell's cellular membrane, or on the outside of the cell. If the metallic particle is located on the outside of the cell, it can be connected or targeted to the exterior surface of the cell's cellular membrane. If the metallic composition is located within the cell, it may include inherent metallic compositions such as hemoglobin. Exemplary methods of targeting or connecting a metallic composition to a cell are described herein.

The applied magnetic field can interact with a metallic composition located within the cell or located external and connected to the cell. The interaction of the magnetic field with the composition can cause a change in the cell. A change "in" the cell is not limited to changes internal to the cell's cellular membrane. A change "in" the cell is inclusive of changes within the cell, and also includes any change to, of, or in the cell caused by the interaction of the magnetic field with the composition. For example, changes that can occur "in" the cell include movement of the cell, movement of one or more cell components, movement of the metallic composition, a change in the cellular membrane tension level of the cell, and a change in the internal strain field of the cell. Changes in the cell that cause changes, including those listed above, of neighboring or surrounding cells or tissues can also be detected. Thus, changes in a cell can cause changes in surrounding cells or tissues. The changes in the surrounding cells or tissues can be detected using the methods and systems described herein. Compositions located within or external to the cell can cause one or more detectable changes in the cell when contacted by an applied magnetic field.

A detectable internal strain field can be generated in a cell when a metallic composition, including a metallic nanoparticle, is under the action of an external force. The internal strain field can be detected using phase sensitive OCT using block correlation signal processing techniques that have been applied in elasticity imaging in ultrasound imaging. The external force may be provided by the application of an external magnetic flux density (B). Action of the external force on each metallic composition can produce movement of the metallic composition ($z_{np}(t)$) that produces a change in the cellular membrane tension level or an internal strain field within a cell. Action of a force on each metallic composition in a cell or tissues produces a movement of the metallic composition ($z_{np}(t)$). Movement of the metallic composition can be along the z-direction. The metallic composition can also have movement in any direction which may be written as vector displacement, $u_{np}(r_o)$ for a metallic composition positioned at $r_o$. Metallic composition displacement $u_{np}(r_o)$ can produce a displacement field ($u(r,r_o)$) in the proteins in the cell containing the metallic composition and surrounding cells. In the case of a homogeneous elastic media, the displacement field ($u(r,r_o)$) can be computed for a semi-infinite half-space following, for example, the method of Mindlin (R. D. Mindlin, A force at a point of a semi-infinite solid, Physics 1936, 7:195-202, which is incorporated by reference for the methods taught therein). In the case of an inhomogenous viscoelastic media, a finite element method numerical approach can be applied to compute the displacement field in the cell. The displacement field ($u(r,r_o)$) produced by a metallic composition positioned at $r_o$ can induce an internal stain field that is determined by change in the displacement field along a particular direction. The strain field ($\in_{ij}(r,r_o)$) is a tensor quantity and is given by, $$\varepsilon_{ij}(r, r_o) = \frac{\partial u_i(r, r_o)}{\partial x_j}$$

where $u_i(r,r_o)$ is the i'th component of the displacement field and $x_j$ is the $j^{th}$ coordinate direction. For example, when j=3, $x_3$ is the z-direction. The internal strain field in a cell due to all metallic compositions in the cell and surrounding cells is a superposition of the strain fields due to each metallic composition. A detectable change in a cell can also be caused with light energy. For example, pulsed laser light can be applied to contact a metallic particle comprised by the cell, where the metallic particle is included in a cell either naturally occurring or administered exogenously and the metallic particle is affected by the pulsed laser light. The application of light energy can cause a detectable change in optical path due to a change in optical refractive and thermal elastic expansion. The light energy can also cause motion of the cell, particle, or tissues proximate to the cell for detection by optical coherence tomography or phase sensitive optical coherence tomography. Such movement can be caused by thermal elastic expansion. Alternatively, sound energy can cause motion of the cell, particle, or tissues proximate to the cell for detection by optical coherence tomography or phase sensitive optical coherence tomography.

The change in the cell can be detected using optical coherence tomographic imaging modalities. Thus, the cell can be detected by detecting the change in the cell caused by the interaction of the magnetic field with the metallic composition using such a modality. The change can be detected using a phase sensitive optical coherence tomographic imaging modality. Non-limiting examples of phase sensitive optical coherence tomographic (OCT) imaging modalities are described herein. Phase sensitive OCT imaging modalities can comprise a probe for transmitting and receiving light energy to and from the cell. The probe can be sized, shaped and otherwise configured for intravascular operation. The probe can further comprise a magnetic source for applying the magnetic field to the cell. The magnetic field can be applied to the cell from a magnetic source located external to the subject or internal to the subject. The external source can be located in a probe or can be distinct from a probe.

Metallic Nanoparticles

The metallic composition can comprise a plurality of metallic nanoparticles and/or a plurality of hemoglobin molecules. The nanoparticles can be substantially spherical in shape and can have a diameter from about 0.1 nanometers (nm) to about 1000.0 nm. The size of the tetrametric hemoglobin protein is approximately 6 nm in diameter. The nanoparticles are not, however, limited to being spherical in shape. Thus, the nanoparticles are asymmetrical in shape. If the nanoparticles are asymmetrical in shape, the largest cross sectional dimension of the nanoparticles can be from about 0.1 nanometers (nm) to about 1000.0 nm in length. The nanoparticles can be hemoglobin.

The metallic composition can comprise metal having non-zero magnetic susceptibility or zero magnetic susceptibility or combinations of non-zero and zero magnetic susceptibility metals. Thus, if the composition comprises nanoparticles, the nanoparticles can all have a non-zero magnetic susceptibility or a zero magnetic susceptibility or a combination of particles having a non-zero magnetic susceptibility and a zero magnetic susceptibility. Metallic compositions having a non-zero magnetic susceptibility can comprise a material selected from the group consisting of iron oxide, iron, cobalt, nickel, chromium and combinations thereof. The metallic compositions can comprise metal having non-zero electrical conductivity or zero electrical conductivity or combinations of non-zero and zero electrical conductivity metals. Also provided is a method for detecting a composition, the method wherein the composition comprises a magnetic or paramagnetic material. Any magnetic or paramagnetic material, whether metallic or non-metallic, can be used in the described methods or with the described systems. In this regard, any material can be used that can cause a change in a cell or can be detected using phase sensitive optical coherence tomography when contacted with an applied magnetic field. Similarly, non-metallic, not magnetic particles can be used to cause a change in a cell or can be detected using phase sensitive optical coherence tomography when contacted with an applied magnetic field using the methods and systems described herein.

The systems, apparatuses and methods can be practiced using metallic compositions without magnetic susceptibility. When using metallic compositions without magnetic susceptibility, or when using compounds having a non-zero magnetic susceptibility, an electrical eddy current can be induced in the composition.

To induce an eddy current in a metallic composition a first time-varying magnetic field can be applied to a cell. The first magnetic field can interact with a metallic composition within or external to the cell to induce an electrical eddy current within the metallic composition. A second magnetic field can be applied to the cell that interacts with the induced eddy current to cause a change in the cell. The cell can be detected by detecting the change in the cell caused by the interaction of the second magnetic field with eddy current using a phase sensitive optical coherence tomographic imaging modality. Exemplary changes in the cell caused by the interaction of the second magnetic field with the eddy current include movement of the cell, movement of the metallic composition, a change in the cellular membrane tension level, and a change in the internal strain field of the cell.

Thus, a metallic composition or a nanoparticle that does not have a significant magnetic permeability can be used. For example, although gold nanoparticles do not have significant magnetic permeability many target-specific molecular agents (e.g., antibodies) can be conjugated to the nanoparticle surface. When using a high-conductivity particle for detection, a magnetic dipole can be induced in the particle by exposing to a time-varying magnetic field (B(t)).

The time-varying magnetic field (B(t)) can cause an electromotive force or potential in the particle that can induce a volumetric and surface electric eddy-current in the high-conductivity nanoparticle. Exemplary circuitry for a magnetic pulser that can be used to produce an eddy current is described in G H Schroder, Fast pulsed magnet systems, Handbook of Accelerator Physics and Engineering, A. Chao and M. Tinger, Eds. 1998 or in IEEE transactions on instrumentation and measurement, VOL. 54, NO. 6, December 2005, pp 2481-2485, which are incorporated herein by reference for the circuitry and methods described therein.

The eddy-current can produce time-varying magnetic moment that can interact with a second applied magnetic field ($B_2$). The induced eddy-current in the high-conductivity nanoparticle or metallic composition and the second applied magnetic field can interact to produce a torque or twist on the nanoparticle or metallic composition. The induced torque can twist the nanoparticle that is mechanically linked to a target in the cell (e.g., the membrane) or located inside the cell. The twisting motion of the nanoparticle can modify the internal strain field of the cell (surrounding cells and tissue) which can be detected using phase sensitive optical coherence tomography. In this approach, phase-sensitive data can be recorded before and after application of a first field to induce an eddy current and block correlation algorithms can be used to compute the depth resolved strain field in the tissue resulting from the motion of the nanoparticle or metallic composition.

In exemplary embodiments, large magnetic fields can be generated by low temperature superconducting magnets. These magnets need only be "charged" once, maintained at a low temperature and do not require an external current to maintain the magnetic field.

A metallic composition can be administered to the subject. Administration of exogenous metallic compositions, for example, metallic nanoparticles is described in greater detail below. Optionally, the cell can be located within a subject and the metallic composition can be administered to the subject. Optionally, the cell can be a macrophage and at least one metallic nanoparticle can be located within the macrophage or can be connected to the macrophage. The macrophage can be located in an atherosclerotic plaque within the subject. The macrophage can also be located within the eye of the subject.

The change in the cell caused by the interaction of the magnetic field with the metallic composition can be detected by generating a phase sensitive optical coherence tomographic image. A phase sensitive optical coherence tomographic image can comprise one or more lines of phase sensitive light energy data captured using a phase sensitive optical coherence tomography modality, wherein at least one line is captured during the application of the magnetic field.

One or more data line can be produced by generating light energy and transmitting at least a first portion of the generated light energy onto a reference reflector wherein at least a portion of the transmitted first portion of light energy is reflected by the reference reflector. At least a second portion of the generated light energy can be transmitted to contact the cell wherein at least a portion of the light energy that contacts the cell is reflected by the cell. The light energy reflected by the reference reflector and by the cell can be received, and the received light energy can be combined, and the received light energy can interfere. The combined light energy is processed to produce a phase sensitive optical coherence data line.

One or more data lines can also be produced by generating light energy and transmitting at least a first portion of the generated light energy onto a reference reflector wherein at least a portion of the transmitted first portion of light energy is reflected by the reference reflector. At least a second portion of the generated light energy can be transmitted to contact the metallic composition wherein at least a portion of the light energy that contacts the metallic composition is reflected by the composition. The light energy reflected by the reference reflector and by the composition can be received. The received light energy can be combined, wherein the received light energy interferes. The combined light energy can be processed to produce the phase sensitive optical coherence data line. One or more data lines can also be produced by generating light energy and transmitting at least a first portion of the generated light energy onto a reference reflector wherein at least a portion of the transmitted first portion of light energy is reflected by the reference reflector. At least a second portion of the generated light energy can be transmitted to contact the metallic composition wherein at least a portion of the light energy that contacts the metallic composition is reflected by the composition. The light energy reflected by the reference reflector and by the composition can be received. The received light energy can be combined, wherein the received light energy interferes. The combined light energy can be processed to produce the phase sensitive optical coherence data line. The phase sensitive optical coherence A-lines can be recorded before or after application of the stimulating field (magnetic, eddy-current, generation of pulsed light energy). Thus, the methods can further comprise recording reference phase sensitive optical coherence A-line prior to the non-lethal change and second phase sensitive optical coherence A-line during or after non-lethal change. The reference and second optical coherence A-line data can be correlated to quantify the non-lethal change.

Phase sensitive light energy data lines can include the spectral dependent complex amplitude of light reflected from the cell, $A_c(v)$, where v is the optical frequency of light. More precisely, what can be measured is product of the amplitudes of light reflected from the cell and reference: $A_c(v) \cdot A_r(v)^*$ where $A_r(v)^*$ is the conjugate of the spectrally-dependent complex amplitude of light reflected from the reference. The quantity $A_c(v) \cdot A_r(v)^*$ can be used to determine $A_c(v)$ the phase sensitive amplitude of light backreflected from the cell/tissue at different time-delays τ by using a time-frequency transformation (e.g., Fourier).

A plurality of phase sensitive optical coherence A-lines can be captured and used to construct an image. A phase sensitive image produced using the described systems and methods can have a phase sensitive resolution of at least about 30.0 nanometers (nm), 25.0 nm, 15.0 nm, 10.0 nm, 5.0 nm, 4.0 nm, 3.0 nm, or 2.0 nm. A plurality of phase sensitive optical coherence A-lines can be spatially and temporally distinct and the image can comprise a B-mode image frame of at least two of the data lines. The plurality of phase sensitive light energy data lines can also be temporally distinct and the image can comprise an M-mode image comprising at least two of the lines.

When a plurality of lines are used to create an image, at least a first phase sensitive light energy data line can be captured prior to the application of the magnetic field and at least a second phase sensitive light energy data line can be captured during application of the magnetic field, or generally the external stimulus. The magnetic field strength can be altered between the capture of data lines or between the capture of images. For example, at least a first phase sensitive light energy data line can be captured during the application of the magnetic field, wherein the magnetic field has a first predetermined strength and at least a second phase sensitive light energy data line during application of a second magnetic field having a second predetermined strength. The captured lines can be processed to create an image. Optionally, the first predetermined strength can be less than the second predetermined strength.

The described methods allows for the construction of both conventional intensity based OCT B-scan images and phase sensitive B-scan images. The phase sensitive B-scan images for viewing can correspond to changes in phase formed by at least two phase sensitive B-scan images corresponding to different magnetic field strengths (one of which can be zero magnetic field strength). At least two types of images can be viewed—one, a conventional intensity based OCT B-scan image and second a phase sensitive B-scan image formed by the difference of two phase sensitive images recorded at different magnetic field strengths.

Also provided are methods for detecting a composition comprising metal by applying a magnetic field to the composition, wherein the magnetic field interacts with the composition. The metallic composition can be detected using a phase sensitive optical coherence tomographic imaging modality. As described throughout, the composition can be located in a cell or can be connected to a cell. The composition can also be located in connection with non-cellular biological matter. For example, non-cellular biological matter can include a protein, a lipid, a peptide, and a nucleic acid.

The methods of detecting cells and compositions using optical coherence tomography can comprise administering a plurality of metallic nanoparticles to a subject or imaging nanoparticles present within a cell.

Optionally, at least one administered nanoparticle localizes within a macrophage located in the subject. At least one administered nanoparticle can also be optionally configured to localize to a target site in the subject. Optionally, at least one nanoparticle is present within a cell. Optionally, the nanoparticle may be a hemoglobin molecule.

In the methods described herein, a nanoparticle comprising a material with non-zero magnetic susceptibility can be positionally moved in vivo or in vitro by an applied magnetic field. A material of non-zero magnetic susceptibility can include a variety of materials. For example, the nanoparticle can comprise any physiologically tolerable magnetic material or combinations thereof. The term magnetic material can optionally include any material displaying ferromagnetic, paramagnetic or superparamagnetic properties. For example, the nanoparticles can comprise a material selected from the group consisting of iron oxide, iron, cobalt, nickel, and chromium. Metallic compositions as described throughout, including administered nanoparticles, can be magnetic. Optionally, a nanoparticle comprises iron oxide. When a nanoparticle comprises metal or magnetic materials, it can be moved while in the subject using an internally or externally applied magnetic field, as described below. Any relevant metal with non-zero magnetic susceptibility or combinations thereof can be used. Many useable metals are known in the art; however, any metal displaying the desired characteristics can be used. Nanoparticles can also comprise a combination of a material with a non-zero magnetic susceptibility and a material with a lower or zero magnetic susceptibility. For example, gold can be combined with higher magnetic susceptibility materials (e.g., iron). For example, gold coated iron can be used. Nanoparticles can also comprise polymers or other coating materials alone or in combination. Such polymers or coating materials can be used to attach targeting ligands, including but not limited to antibodies, as described below. When used in vivo, an administered nanoparticle can be physiologically tolerated by the subject, which can be readily determined by one skilled in the art.

Nanoparticles can be solid, hollow or partially hollow and can be spherical or asymmetrical in shape. Optionally, the cross section of an asymmetric nanoparticle is oval or elliptical. As one of skill in the art will appreciate, however, other asymmetric shapes can be used. The nanoparticles can comprise shelled or multi-shelled nanoparticles. Shelled or multi-shelled nanoparticles can have targeting ligands conjugated to the shell material wherein the targeting ligand has an affinity for or binds to a target site in a subject or ex vevo. Such shelled or multi-shelled nanoparticles can be made, for example, using techniques known in the art, for example, as described in Loo et al., "Nanoshell-Enabled Photonics-Based Imaging and Therapy of Cancer," Tech. Cancer Res. and Treatment, (2004) 3(1) 33-40, which is incorporated herein by reference for the methods taught herein. Further, Oldenburg et al., "Nanoengineering of Optical Resonances," Chemical Physics Letters (1998) 288, 243-247, is incorporated herein for methods of nanoshell synthesis.

Localizing Nanoparticles

A metallic composition, including a nanoparticle, can be configured to localize to a target site within the subject. For example, the metallic composition can be configured to localize to a neoplastic cell, to a peptide, to a protein, or to a nucleic acid. Optionally, the target site is an extracellular domain of a protein. A variety of cell types can also be targets of the metallic compositions. For example, target cells can be selected from one or more of a neoplastic cell, a squameous cell, a transitional cell, a basal cell, a muscle cell, an epithelial cell, and a mucosal cell. The target cells can also be located at different anatomical locations within a subject. For example, the cell can be located in the subject at an anatomical location selected from the group consisting of a lung, bronchus, intestine, stomach, colon, eye, heart, blood vessel, cervix, bladder, urethra, skin, muscle, liver, kidney, and blood.

One or more administered nanoparticle can localize to a desired target within the subject using passive or active targeting mechanisms. Passive targeting mechanisms take advantage of the subject's inherent defense mechanisms to highlight phagocytic cells naturally responsible for particle clearance. For example, macrophage rich areas are a pathological correlate to an unstable atherosclerotic plaque in a subject. Moreover, administered nanoparticles, for example, small superparamagneitc and ultrasmall superparamagnetic particles of iron oxide, are avidly taken up, or engulfed by, macrophages located in unstable plaques. Thus, through the subject's natural defense mechanism, wherein macrophages accumulate in an unstable atherosclerotic plaque and engulf administered nanoparticles, administered nanoparticles can passively target the unstable plaque. Similarly, macrophages located in the eye of a subject can engulf nanoparticles. Such passive targeting of nanoparticles can be used with the methods and apparatuses described herein to highlight a plaque's instability or to highlight other accumulation of phagocytic cells.

Active targeting mechanisms can refer to the use of ligand-directed, site-specific targeting of nanoparticles. A nanoparticle can be configured to localize to a desired target site in a subject using a wide variety of targeting ligands including, but not limited to, antibodies, polypeptides, peptides, nucleic acids, and polysaccharides. Such nanoparticles are referred to herein as "targeted nanoparticles." Targeting ligands or fragments thereof can be used to target a nanoparticle to cellular, or other endogenous or exogenous biomarkers in the subject. Such a biomarkers or "target sites" can include, but are not limited to, proteins, polypeptides, peptides, polysaccharides, lipids, or antigenic portions thereof, which are expressed within the subject. When active targeting mechanisms are used to target a cell, the targeted nanoparticle can be optionally internalized by the targeted cell.

Thus, using the disclosed methods, at least one administered nanoparticle can optionally localize within a macrophage located in the subject and/or at least one administered targeted nanoparticle can localize to a desired target site in the subject.

The methods and apparatuses are not, however, limited to in vivo administration to a subject. As would be clear to one skilled in the art, nanoparticles, including targeted nanoparticles, can be administered in vitro to an ex vivo sample with localization of the nanoparticle to a desired target site and subsequent imaging occurring in vitro. Moreover, a composition, including at least one nanoparticle can be administered to a subject in vivo, and a sample can be subsequently taken from the subject and imaged ex vivo using the methods, systems, and apparatuses described herein.

When using a targeted nanoparticle the target site in vivo or in vitro can be endogenous or exogenous. The target site can be selected from the group consisting of an organ, cell, cell type, blood vessel, thrombus, fibrin and infective agent antigens or portions thereof. Optionally, the target site can be a neoplastic cell. The target site can also be an extracellular domain of a protein. Furthermore, the target site can be selected from the group consisting of a lung, bronchus, intestine, stomach, colon, heart, brain, blood vessel, cervix, bladder, urethra, skin, muscle, liver, kidney and blood. The target site can also be a cell. For example, a cell can be selected from the group consisting of, but not limited to, a neoplastic cell, a squameous cell, a transitional cell, a basal cell, a muscle cell, an epithelial cell, a lymphocyte, a leukocyte, a monocyte, a red blood cell, and a mucosal cell.

Thus, targeted nanoparticles can be targeted to a variety of cells, cell types, antigens (endogenous and exogenous), epitopes, cellular membrane proteins, organs, markers, tumor markers, angiogenesis markers, blood vessels, thrombus, fibrin, and infective agents. For example, targeted nanoparticles can be produced that localize to targets expressed in a subject. Optionally, the target can be a protein, and can be a protein with an extracellular or transmembrane domain. Optionally, the target can be the extracellular domain of a protein.

Desired targets can be based on, but not limited to, the molecular signature of various pathologies, organs and/or cells. For example, adhesion molecules such as integrin $\alpha v \beta 3$, intercellular adhesion molecule-1 (I-CAM-1), fibrinogen receptor GPIIb/IIIa and VEGF receptors are expressed in regions of angiogenesis, inflammation or thrombus. These molecular signatures can be used to localize nanoparticles through the use of a targeting ligand. The methods described herein optionally use nanoparticles targeted to one or more of VEGFR2, I-CAM-1, $\alpha v \beta 3$ integrin, $\alpha v$ integrin, fibrinogen receptor GPIIb/IIIa, P-selectin, and/or mucosal vascular adressin cell adhesion molecule-1.

As used in this invention, the term "epitope" is meant to include any determinant capable of specific interaction with a targeting ligand as described below. Epitopic determinants can consist of chemically active surface groupings of molecules such as amino acids or sugar side chains and can have specific three dimensional structural characteristics, as well as specific charge characteristics.

Targeting ligands specific for a molecule that is expressed or over-expressed in a cell, tissue, or organ targeted for imaging, such as pre-cancerous, cancerous, neoplastic, or hyperproliferative cells, tissues, or organs, can be used with the nanoparticles described herein. This use can include the in vivo or in vitro imaging, detection, or diagnosis of pre-cancerous, cancerous, neoplastic or hyperproliferative cells in a tissue or organ. The compositions and methods of the invention can be used or provided in diagnostic kits for use in detecting and diagnosing cancer.

As used herein, a targeted cancer to be imaged, detected or diagnosed can be selected from, but are not limited to, the group comprising lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

Pre-cancerous conditions to be imaged, detected or diagnosed include, but are not limited to, cervical and anal dysplasias, other dysplasias, severe dysplasias, hyperplasias, atypical hyperplasias, and neoplasias. As would be clear to one skilled in the art, however, additional cancers and pre-cancerous conditions can be imaged, detected or diagnosed using the methods and apparatuses described herein.

Using methods known in the art, and as described herein, targeting ligands, such as polyclonal or monoclonal antibodies, can be produced to desired target sites in a subject. Thus, a targeted nanoparticle can further comprise an antibody or a fragment thereof. Methods for preparing and characterizing antibodies are well known in the art (See, e.g., Antibodies: A Laboratory Manual, Cold Spring Harbor Laboratory, 1988; incorporated herein by reference for the methods taught therein).

Monoclonal antibodies can be obtained from a population of substantially homogeneous antibodies, i.e., the individual antibodies comprising the population are identical except for possible naturally-occurring mutations that can be present in minor amounts. Thus, the modifier "monoclonal" indicates the character of the antibody as not being a mixture of discrete antibodies.

For example, the monoclonal antibodies of the invention can be made using the hybridoma method first described by Kohler & Milstein, Nature 256:495 (1975), or can be made by recombinant DNA methods (Cabilly, et al., U.S. Pat. No. 4,816,567).

In the hybridoma method, a mouse or other appropriate host animal, such as hamster can be immunized to elicit lymphocytes that produce or are capable of producing antibodies that will specifically bind to the antigen used for immunization. Alternatively, lymphocytes can be immunized in vitro. Lymphocytes can be then fused with myeloma cells using a suitable fusing agent, such as polyethylene glycol, to form a hybridoma cell (Goding, Monoclonal Antibodies: Principles and Practice, pp. 59-103 (Academic Press, 1986)).

DNA encoding a monoclonal antibody can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA can be placed into expression vectors, which can then be transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences, Morrison, et al., Proc. Nat. Acad. Sci. 81, 6851 (1984), or by covalently joining to the immunoglobulin coding sequence all or part of the coding sequence for a non-immunoglobulin polypeptide. In that manner, "chimeric" or "hybrid" antibodies can be prepared that have the binding specificity of an anti-cancer, pre-cancer, or hyperproliferative cell or other target molecule. Optionally, the antibody used herein is "humanized" or fully human.

Non-immunoglobulin polypeptides can be substituted for the constant domains of an antibody of the invention, or they can be substituted for the variable domains of one antigen-combining site of an antibody of the invention to create a chimeric bivalent antibody comprising one antigen-combining site having specificity for a first antigen and another antigen-combining site having specificity for a different antigen.

Chimeric or hybrid antibodies also can be prepared in vitro using known methods in synthetic protein chemistry, including those involving crosslinking agents.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321, 522-525 (1986); Riechmann et al., Nature 332, 323-327 (1988); Verhoeyen et al., Science 239, 1534-1536 (1988)), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Antibodies can be humanized with retention of high affinity for the target site antigen and other favorable biological properties. Humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target site antigen(s), can be achieved. In general, the CDR residues are directly and most substantially involved in influencing antigen binding.

Human monoclonal antibodies can be made by a hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Dekker, Inc., New York, 1987).

Transgenic animals (e.g., mice) can be used that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Alternatively, phage display technology (McCafferty et al., Nature 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S. and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced can confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., Nucl. Acids Res. 21, 2265-2266 (1993), and the isolation of a high affinity human antibody directly from such large phage library is reported by Griffith et al., EMBO J. (1994). Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

Bispecific antibodies are monoclonal, preferably human or humanized, antibodies that have binding specificities for at least two different antigens. One of the binding specificities is for a first antigen and the other one is for a second antigen.

Traditionally, the recombinant production of bispecific antibodies is based on the coexpression of two immunoglobulin heavy chain-light chain pairs, where the two heavy chains have different specificities (Millstein and Cuello, Nature 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., EMBO 10, 3655-3659 (1991). For further details of generating bispecific antibodies see, for example, Suresh et al., Methods in Enzymology 121, 210 (1986).

Heteroconjugate antibodies are also within the scope of the described compositions and methods. Heteroconjugate antibodies are composed of two covalently joined antibodies. Heteroconjugate antibodies can be made using any convenient cross-linking methods. Suitable cross-linking agents are well known in the art, and are disclosed in U.S. Pat. No. 4,676,980, along with a number of cross-linking techniques.

A variety of immunoassay formats can be used to select antibodies that selectively bind with a desired target site or target site antigen. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Not only can a targeted nanoparticle comprise an antibody or fragment thereof, but a targeted nanoparticle can also comprise targeting ligand that is a polypeptide or a fragment thereof. Optionally, polypeptides that are internalized by target cells can be attached to the surface of a nanoparticle. Ligands that are internalized can optionally be used for internalization of a nanoparticle into a target cell. A modified phage library can be use to screen for specific polypeptide sequences that are internalized by desired target cells. For example, using the methods described in Kelly et al., "Detection of Vascular Adhesion Molecule-1 Expression Using a Novel Multimodal Nanoparticle," Circulation Res., (2005) 96:327-336, which is incorporated herein for the methods taught therein, polypeptides can be selected that are internalized by VCAM-1 expressing cells or other cells expressing a ligand of interest.

There are a number of methods for isolating proteins which can bind a desired target. For example, phage display libraries have been used to isolate numerous polypeptides that interact with a specific target. (See for example, U.S. Pat. Nos. 6,031,071; 5,824,520; 5,596,079; and 5,565,332 which are herein incorporated by reference at least for their material related to phage display and methods related to combinatorial chemistry). Thus targeted nanoparticles can comprise a polypeptide or fragments thereof that interact with a desired target. A targeted nanoparticle can also comprise a binding domain of an antibody or phage.

The term "polypeptide" or "peptide" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. A fragment can be produced by a proteolytic reaction, but it should be recognized that a fragment need not necessarily be produced by a proteolytic reaction but can be produced using methods of chemical synthesis or methods of recombinant DNA technology, to produce a synthetic peptide that is equivalent to a proteolytic fragment. It should be recognized that the term "polypeptide" is not used herein to suggest a particular size or number of amino acids comprising the molecule, and that a polypeptide of the invention can contain up to several amino acid residues or more.

A nanoparticle can bind selectively or specifically to a desired target site, and/or can be internalized by a target cell. Such selective or specific binding and/or internalization can be readily determined using the methods, systems and apparatuses described herein. For example, selective or specific binding can be determined in vivo or in vitro by administering a targeted nanoparticle and detecting an increase in light scattering from the nanoparticle bound to a desired target site or internalized into the desired target cell.

Detection of light scattering can be measured using the systems and apparatuses described below.

Thus, a targeted nanoparticle can be compared to a control nanoparticle having all the components of the targeted nanoparticle except the targeting characteristics, such as, for example, targeting ligand. By detecting phase sensitive image data from the targeted nanoparticle bound to a desired target site versus a control nanoparticle, the specificity or selectivity of binding or internalization can be determined. If an antibody, polypeptide, or fragment thereof, or other targeting ligand is used, selective or specific binding to a target can be determined based on standard antigen/polypeptide/epitope/antibody complementary binding relationships. Further, other controls can be used. For example, the specific or selective targeting of the nanoparticles can be determined by exposing targeted nanoparticles to a control tissue, which includes all the components of the test or subject tissue except for the desired target ligand or epitope. To compare a control sample to a test sample, levels of light scattering can be detected by, for example, the systems described below and the difference in levels or location can be compared.

A targeting ligand can be coupled to the surface or shell of at least one of the nanoparticle. Targeted nanoparticles comprising targeting ligands can be produced by methods known in the art. For example ligands, including but not limited to, antibodies, peptides, polypeptides, or fragments thereof can be conjugated to the nanoparticle surface.

Any method known in the art for conjugating a targeting ligand to a nanoparticle can be employed, including, for example, those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). Established protocols have been developed for the labeling metallic nanoparticles with a broad range of biomolecules, including protein A, avidin, streptavidin, glucose oxidase, horseradish peroxidase, and IgG (antibodies). Nanoparticles can be prepared with bioorganic molecules on their surface (DNA, antibodies, avidin, phospholipids, etc). The nanoparticles can be characterized, modified, and conjugated with organic and biomolecules. Polymers or other intermediate molecules can be used to tether antibodies or other targeting ligands to the surface of nanoparticles. Methods of tethering ligands to nanoparticles are know in the art as described in, for example, Loo et al., "Nanoshell-Enabled Photonics-Based Imaging and Therapy of Cancer," Tech. Cancer Res. and Treatment, (2004) 3(1) 33-40, which is incorporated herein by reference for the methods taught herein.

Covalent binding of a targeting ligand to a nanoparticle can be achieved, for example, by direct condensation of existing side chains or by the incorporation of external bridging molecules. Many bivalent or polyvalent agents can be useful in coupling polypeptide molecules to other particles, nanoparticles, proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that can be used.

Optionally, one can first derivatize an antibody if used, and then attach the nanoparticle to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α(2-pyridyldithio)toluene).

Targeting ligands can also be conjugated to nanoparticles using methods including the preparation of biotinylated antibody molecules and their consequent interaction with streptavidin/nanoparticle conjugates. This approach takes advantage of strong biospecific interaction between biotin and streptavidin and known protocols for immobilization of streptavidin on nanoparticles. Polypeptides with thiol terminated alkyl chains can be directly attached to the surface of nanoparticles using the procedures described in Elghanian, R., et al., Selective colorimetric detection of polynucleotides based on the distance-dependent optical properties of gold nanoparticles. Science, 1997. 277(5329): p. 1078-1080 (incorporated by reference for the methods taught therein). For conjugation procedure one can use a mixture of thiol terminated polypeptides and relatively small mercaptoacetic molecules to avoid high density immobilization of the polypeptides.

Targeted nanoparticles can be prepared with a biotinylated surface and an avidinated antibody, peptide, polypeptide or fragment thereof can be attached to the nanoparticle surface using avidin-biotin bridging chemistry. Avidinated nanoparticles can be used and a biotinylated antibody or fragment thereof or another biotinylated targeting ligand or fragments thereof can be administered to a subject. For example, a biotinylated targeting ligand such as an antibody, protein or other bioconjugate can be used. Thus, a biotinylated antibody, targeting ligand or molecule, or fragment thereof can bind to a desired target within a subject. Once bound to the desired target, the nanoparticle with an avidinated surface can bind to the biotinylated antibody, targeting molecule, or fragment thereof. When bound in this way, light energy can be transmitted to the bound nanoparticle, which can produce light scattering of the transmitted light. An avidinated nanoparticle can also be bound to a biotinylated antibody, targeting ligand or molecule, or fragment thereof prior to administration to the subject.

When using a targeted nanoparticle with a biotinylated surface or an avidinated surface a targeting ligand can be administered to the subject. For example, a biotinylated targeting ligand such as an antibody, polypeptide or other bioconjugate, or fragment thereof, can be administered to a subject and allowed to accumulate at a target site When a targeted nanoparticle with a biotinylated surface is used, an avidin linker molecule, which attaches to the biotinylated targeting ligand can be administered to the subject. Then, a targeted nanoparticle with a biotinylated shell can be administered to the subject. The targeted nanoparticle binds to the avidin linker molecule, which is bound to the biotinylated targeting ligand, which is itself bound to the desired target. In this way, a three step method can be used to target nanoparticles to a desired target. The targeting ligand can bind to all of the desired targets detailed above as would be clear to one skilled in the art.

Nanoparticles, including targeted nanoparticles, can also comprise a variety of markers, detectable moieties, or labels. Thus, for example, a nanoparticle equipped with a targeting ligand attached to its surface can also include another detectable moiety or label. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes. Of course, the derivatives of these compounds are included as common fluorescent moieties.

The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable can be employed.

A composition, including at least one nanoparticle, can be administered to a subject orally, parenterally (e.g., intravenously), by intramuscular injection, by intraperitoneal injection, transdermally, extracorporeally, topically or the like. Parenteral administration of a composition, if used, is generally characterized by injection. Injectables can be prepared in conventional forms, either as liquid solutions or suspensions, solid forms suitable for solution of suspension in liquid prior to injection, or as emulsions.

The compositions, including nanoparticles, can be used in combination with a pharmaceutically acceptable carrier. By "pharmaceutically acceptable" is meant a material that is not biologically or otherwise undesirable, i.e., the material can be administered to a subject, along with the nanoparticle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5.0 to about 8.0, and more preferably from about 7.0 to about 7.5. As described above, compositions can be administered intravascularly. Administered compositions can include carriers, thickeners, diluents, buffers, preservatives, surface active agents and the like in addition to the composition of choice. Administered compositions can also include one or more active ingredients such as antimicrobial agents, anti-inflammatory agents, anesthetics, and the like.

When used in the described methods, an effective amount of one of the compositions, including the nanoparticles, of the present invention can be determined by one skilled in the art. The specific effective dose level for any particular subject can depend upon a variety of factors including the type and location of the target site, activity of the specific composition employed, the specific composition employed, the age, body weight, general health, sex and diet of the subject, the time of administration, the route of administration, the rate of excretion of the specific composition employed, the duration of the treatment, drugs used in combination or coincidental with the specific composition employed, and like factors well known in the medical arts. For example, it is well within the skill of the art to start doses of the composition at levels lower than those required to achieve the desired diagnostic or imaging effect and to gradually increase the dosage until the desired effect is achieved. If desired, an effective dose can be divided into multiple doses for purposes of administration.

Depending on the exemplary factors above, on the composition used, on the intended target site for the composition, and whether active or passive targeting of the described compositions is used, the time between administration of the described compositions and the detection of the described nanoparticles within the subject can vary. For example, detection of the described nanoparticles can be performed at one or more time seconds, minutes, hours, days, and/or weeks after administration of the compositions to the subject. When and how frequently methods of detection of an administered composition are performed can be determined by one skilled in the art through routine administration and detection.

OCT System

Also provided herein are systems for detecting a cell or metallic composition. An exemplary system comprises a magnet for applying a magnetic field to a cell and a phase sensitive optical coherence tomographic imaging modality for detecting the cell and/or metallic composition. The phase sensitive optical coherence tomographic imaging modality can comprise a probe for transmitting and receiving light energy to and from the cell. The probe can be an intravascular probe.

The phase sensitive optical coherence tomographic imaging modality included in the system can comprise a light source, a light splitter, a probe and a reference reflector. The phase sensitive optical coherence tomographic imaging modality may include the light splitter, but does not need to include a light splitter, i.e. a light coupler and the like may be used. Light energy generated by the light source can be transmitted to and split by the splitter for transmission to the reference reflector and to the probe. The probe can be configured to transmit at least a portion of the light energy transmitted thereto into a target cell and to receive reflected light energy from the target cell and the reference reflector can be configured to reflect at least a portion of the light energy transmitted thereto. The system can further include a processor for processing reflected light energy from the reference reflector and light energy received by the probe to produce a phase sensitive optical coherence A-line. The reference reflector can be located in the probe.

Although the exemplary systems described also include a multitude of fibers in the sample path, the described systems and methods are not intended to be limited to embodiments having a multitude of fibers. Thus, systems comprising one fiber and methods of using such exemplary systems are covered. Optionally, an exemplary system comprises a probe having a single optical fiber and a rotary reflector in optical communication with the single optical fiber.

FIG. 6 is a block diagram illustrating an exemplary system 100 that can be used for performing the imaging methods with nanoparticles. The nanoparticles are imaged in the blood flow or in the surrounding blood vessels of the blood flow. These exemplary OCT systems are only examples of phase sensitive spectral domain OCT systems and are not intended to suggest any limitation as to the scope of use or functionality of OCT architectures. Neither should the OCT systems be interpreted as having any dependency nor a requirement relating to any one or combination of components illustrated in the exemplary OCT systems.

The OCT system 100 of FIG. 6 includes a general-purpose computing device in the form of a computer 101. The components of the computer 101 can include, but are not limited to, one or more processors or processing units 103, a system memory 112, and a system bus 113 that couples various system components including the processor 103 to the system memory 112.

The system bus 113 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus 113, and all buses specified in this description can also be implemented over a wired or wireless network connection and each of the subsystems, including the processor 103, a mass storage device 104, an operating system 105, an image construction software 106, a nanoparticle movement image construction software 107, light signal data 108, the system memory 112, an OCT input interface 111, an OCT output interface 110, a display adapter 109, a display device 127, a human interface device 102, and a digital image capture device 117, can be contained within one or more remote computers (not shown) at physically separate locations, connected through buses of this form, in effect implementing a fully distributed system.

The computer 101 can include a variety of computer readable media. Such media can be any available media that is accessible by the computer 101 and includes both volatile and non-volatile media, removable and non-removable media.

The system memory 112 includes computer readable media in the form of volatile memory, such as random access memory (RAM), and/or non-volatile memory, such as read only memory (ROM). The system memory 112 typically contains data such as light signal data 108 and/or program modules such as operating system 105, image construction software 106 and nanoparticle movement (or cellular membrane tension level or intenial strain field change) image construction software 107 that are immediately accessible to and/or are presently operated on by the processing unit 103. Throughout this application the disclosed methods, compositions and apparatuses for detecting a cell and/or a metallic composition are described herein variously by reference to metallic particle movement, cellular movement, changes in cellular tension level, changes in internal strain field of a cell, and change in neighboring or surrounding cells and/or tissues(s). It will be understood that description of various aspects of the disclosed methods, compositions and apparatuses by reference to detecting one or more of metallic particle movement, cellular movement, changes in cellular tension level, changes in internal strain field of a cell, and change in neighboring or surrounding cells and/or tissues(s) constitutes description of that aspect of the disclosed methods, compositions and apparatuses to the non-referenced detection of metallic particle movement, cellular movement, changes in cellular tension level, changes in internal strain field of a cell, and change in neighboring or surrounding cells and/or tissues(s), unless the context clearly indicates otherwise. Thus, nanoparticle movement image construction software can also include or alternatively include cellular movement, changes in cellular tension level, changes in internal strain field of a cell, and change in neighboring or surrounding cells and/or tissues(s) image construction software.

The computer 101 can also include other removable/non-removable, volatile/non-volatile computer storage media. By way of example, FIG. 6 illustrates a mass storage device 104 which can provide non-volatile storage of computer code, computer readable instructions, data structures, program modules, and other data for the computer 101. For example, a mass storage device 104 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device 104, including by way of example, an operating system 105, image construction software 106, nanoparticle movement (or cellular membrane tension level or internal strain field change) image construction software 107, and light signal data 108. Each of the operating system 105, image construction software 106, nanoparticle movement (or cellular membrane tension level or internal strain field change) image construction software 107, light signal data 108 (or some combination thereof) can include elements of the programming image construction software 106 and the nanoparticle movement (or cellular membrane tension level or internal strain field change) image construction software 107.

A user can enter commands and information into the computer 101 via an input device (not shown). Examples of such input devices include, but are not limited to, a keyboard, pointing device (e.g., a "mouse"), a microphone, a joystick, a serial port, a scanner, and the like. These and other input devices can be connected to the processing unit 103 via a human machine interface 102 that is coupled to the system bus 113, but can be connected by other interface and bus structures, such as a parallel port, game port, or a universal serial bus (USB).

A display device 127 can also be connected to the system bus 113 via an interface, such as a display adapter 109. For example, a display device can be a monitor. In addition to the display device 127, other output peripheral devices can include components such as speakers (not shown) and a printer (not shown) which can be connected to the computer 101 via an input/output interface (not shown).

The computer 101 can operate in a networked environment using logical connections to one or more remote computing devices (not shown). By way of example, a remote computing device can be a personal computer, portable computer, a server, a router, a network computer, a peer device or other common network node, and so on. Logical connections between the computer 101 and a remote computing device (not shown) can be made via a local area network (LAN) and a general wide area network (WAN). Such networking environments are commonplace in offices, enterprise-wide computer networks, intranets, and the Internet. In a networked environment, image construction software 106, nanoparticle movement (or cellular membrane tension level or internal strain field change) image construction software 107 and light signal data 108 depicted relative to the computer 101, or portions thereof, can be stored in a remote memory storage device (not shown). For purposes of illustration, application programs and other executable program components such as the operating system are illustrated herein as discrete blocks, although it is recognized that such programs and components reside at various times in different storage components of the computing device 101, and are executed by the data processor(s) of the computer.

An implementation of the image construction software 106 and the nanoparticle movement (or cellular membrane tension level or internal strain field change) image construction software 107 can be stored on or transmitted across some form of computer readable media. Computer readable media can be any available media that can be accessed by a computer. By way of example, and not limitation, computer readable media can comprise "computer storage media" and "communications media." "Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The light signal data 108 can enter the computer 101 via the OCT input interface 111. The OCT output interface can be IEEE-488, IEEE-1 394, Universal Serial Bus (USB), or the like. The light. signal data 108 can be stored in mass storage device 104 and transferred to system memory 112 as light signal data 108 to be used by image construction software 106 and nanoparticle movement (or cellular membrane tension level or internal strain field change) image construction software 107.

The OCT output interface 110 connects the computer 101 to a magnet control 114. This connection can allow a user to regulate the current sent to a magnet 115 and a magnet 116 by the magnet control 114. The magnet control 114 directs current flow into the magnets 115 or 116. The magnet control 114 can work in conjunction with a line scan camera 139 so that a user-specified field pulse sequence is present at the scanning site.

FIG. 6 illustrates an example of a Phase Sensitive OCT system 100. The Phase Sensitive OCT system 100 can be utilized in conjunction with the computer and network architectures described above.

The Phase Sensitive OCT system 100 can include a general-purpose computing device in the form of a computer 101 and all subsystems of the computer 101, as previously described. The Phase Sensitive OCT system 100 can also include, as previously described, a display device 127, a magnet control 114, and a magnet 116.

Light energy can be generated by a light source 117. The light source 117 can be a broadband laser light source coupled into optical fiber emitting light energy over a broad range of optical frequencies. For example, the range can be from about 400 nanometers to about 1600 nanometers. The light energy can be emitted over a multiplicity of optical wavelengths or frequencies. Alternatively, the light source can be a narrowband tunable laser light source wherein the optical wavelengths generated range from about 400 nanometers to about 1600 nanometers. The light spectrum is continually varied in time, over a specified spectral region. As used herein, optical fiber can refer to glass or plastic wire or fiber. Optical fiber is indicated on FIG. 6 as lines connecting the various blocks of the figures. Where light energy is described as "passing," "traveling," "returning," "directed," or similar movement, such movement can be via optical fiber.

A fraction of the generated light energy passes from the light source 117 into an optical spectrum analyzer 118. The optical spectrum analyzer 118 measures optical frequency as the light energy is emitted from the light source 117 as a function of time. The optical spectrum analyzer 118 samples a portion of the light emitted by the light source 117. The optical spectrum analyzer 118 monitors the power spectral density of light entering the splitter 119. The remaining fraction of light energy from the light source 117 passes into a splitter 119. The splitter 119 can be a device with four ports. Port 1 allows light energy to enter the splitter 119. Ports 2 and 3 allow light energy to leave and re-enter the splitter 119. Port 4 allows light energy to leave the splitter 119. The splitter 119 couples the light into Port 1. The splitter 119 divides the light according to a pre-determined split ratio selected by a user. For example, the split ratio can be 50/50 wherein half of the light energy entering the splitter 119 at Port 1 exits the splitter 119 through Port 2 and half exits the splitter 119 through Port 3. In another non limiting example, the split ratio can be 60/40 wherein 60% of the light energy passes through Port 2 and 40% of the light energy passes through Port 3.

A fraction of the light energy (determined by the split ratio) that exits the splitter 119 through Port 2 travels to a reference reflector surface 120. The light energy is reflected from the reference reflector surface 120 back to the splitter 119 into Port 2. The reference reflector can be, by way of example, but not limitation, a planar metallic mirror or a multilayer dielectric reflector with a specified spectral amplitude/phase reflectivity. The remaining fraction of light that entered splitter 119 through Port 1 exits splitter 119 through Port 3 and enters an OCT probe 122. The OCT probe 122 can be a turbine-type catheter as described in Patent Cooperation Treaty application PCT/US04/12773 filed Apr. 23, 2004 which claims priority to U.S. provisional application 60/466,215 filed Apr. 28, 2003, each herein incorporated by reference for the methods, apparatuses and systems taught therein. The OCT probe 122 can be located within a subject 121 to allow light reflection off of subject 121 tissues and nanoparticles 123.

The light energy that entered OCT probe 122 is reflected off of the tissue of subject 121 and nanoparticles 123. The reflected light energy passes back through the OCT probe 122 into the splitter 119 via Port 3. The reflected light energy that is returned into Port 2 and Port 3 of the splitter 119 recombines and interferes according to a split ratio. The light recombines either constructively or destructively, depending on the difference of pathlengths. A series of constructive and destructive combinations of reflected light can be used to create an interferogram (a plot of detector response as a function of optical path length difference ($c\tau$) or optical time-delay ($\tau$)). Each reflecting interface from the subject 121 and the nanoparticles can generate an interferogram. The splitter 119 can recombine light energy that is returned through Port 2 and Port 3 so that the light energies interfere. The light energy is recombined in the reverse of the split ratio. For example, if a 60/40 split ratio, only 40% of the light energy returned through Port 2 and 60% of the light energy returned through Port 3 would be recombined. The recombined reflected light energy is directed out Port 4 of the splitter 119 into a coupling lens 137. The coupling lens 124 receives light from the output of the splitter 119 and sets the beam etendue (beam diameter and divergence) to match that of the optical spectrometer 125. The coupling lens 124 couples the light into an optical spectrometer 125. The optical spectrometer 125 can divide the recombined reflected light energy light into different optical frequencies and direct them to different points in space which are detected by a line scan camera 126. The line scan camera 126 performs light to electrical transduction resulting in digital light signal data 108. The digital light signal data 108 is transferred into the computer 101 via the OCT Input interface 111. Interface between the line scan camera 126 and computer 101 can be, for example, IEEE-488, IEEE-1394, Universal Serial Bus (USB), or the like. The digital light signal data 108 can be stored in the mass storage device 104 or system memory 112 and utilized by the image construction software 106 and the nanoparticle movement (or cellular membrane tension level or internal strain field change) image construction software 107.

The preceding exemplary phase sensitive OCT system is only one example of the contemplated systems for imaging tissues and nanoparticles. Variations in layout and equipment known to one skilled in the art are also contemplated.

Figure 18:
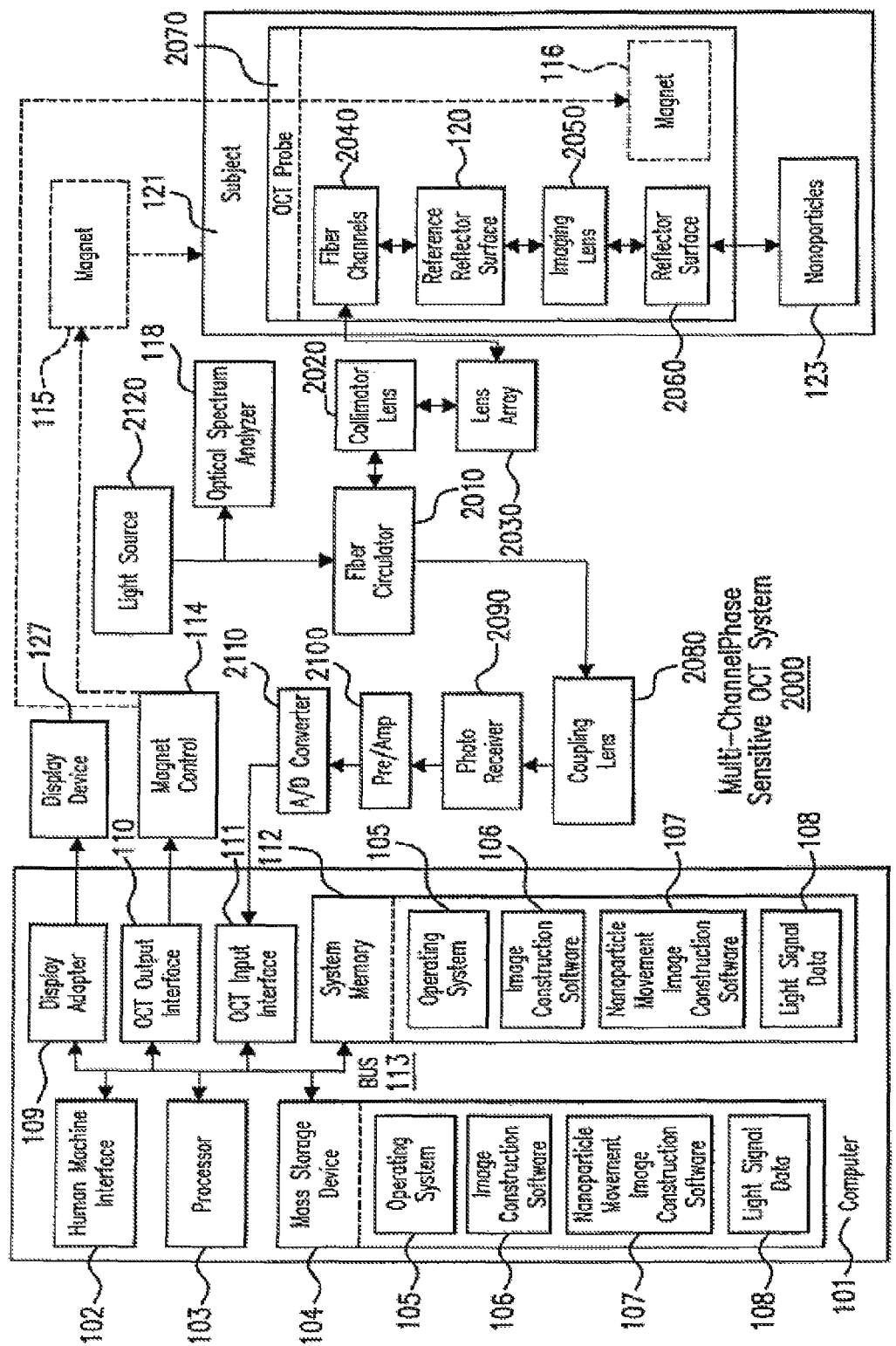
FIG. 18 is a block diagram illustrating a multi-channel phase sensitive OCT system.

FIG. 18 is an exemplary block diagram of a Multi-Channel Phase Sensitive OCT system 2000. The exemplary Multi-Channel Phase Sensitive OCT system 2000 can include a general-purpose computing device in the form of the computer 101, and all subsystems of the computer 101, as described herein. The exemplary multi-channel Phase Sensitive OCT system 2000 can also include, as previously described, a display device 127, a magnet control 114, and a magnet 114 or a magnet 115.

Light energy is generated by a light source 2120. The light source 212 can be a narrow band tunable laser light source wherein the optical wavelengths generated range from about 400 nanometers to about 1600 nanometers. Appropriate selection of a range of optical wavelengths can be readily determined by one skilled in the art. For example, if light energy is to go through substantial water path, i.e., deep tissue, then an operator can select longer optical wavelengths. For example, 1300-1600 nanometers. The light spectrum is continuously varied in time, over a specified spectral region. A fraction of the light energy passes from the light source 2120 into an optical spectrum analyzer 118. The optical spectrum analyzer 118 samples a portion of the light emitted by the light source 212. The optical spectrum analyzer 111 monitors the power spectral density of light entering the circulator 2010. The optical spectrum analyzer 118 can measure optical frequency as it is emitted from the light source 2120 as a function of time. The remaining fraction of light energy generated by the light source 2120 passes into a fiber circulator 2010. The fiber circulator 201 can comprise three ports, designated Port 1, Port 2, and Port 3. Light energy can enter Port 1. Light energy can exit and re-enter Port 2. Light energy can exit Port 3. The fiber circulator 2010 can recombine light energy that re-enters via Port 2. Light energy from the light source 2120 passes into the fiber circulator 2010 through Port 1. The light energy exits the fiber circulator 2010 through Port 2 and enters an OCT probe 2070. The light energy is coupled to a collimator lens 2020. The collimator lens 2020 focuses the light emitted from the fiber at a point infinitely far from the fiber tip.

The light energy is collimated into a lens array 2030. The lens array 2030 can comprise a lattice of microlenses or lenslets. The number of microlenses in the lens array 2030 can be readily determined by one skilled in the art. For each microlens, there is a fiber channel 204 that is coupled to the microlens. Fiber channels 2040 are optical waveguides that confine and guide light along a path. The fiber channels 2040 can be varied in length. Choosing an appropriate length for the fiber channels 2040 is known to one skilled in the art. The difference in the length between fiber channels 2040 can be from about one and a half to about ten times the scan depth in the tissue of a subject 121. This variable length can allow demultiplexing light signal detected from the channels. A fraction of the light energy transmitted into the fiber channels 2040 is reflected from a reference reflector surface 120 back into the fiber channels 2040, through the lens array 2030, into the collimator lens 2020 and into the fiber circulator 2010. This reflected light energy can serve as a reference reflection. The light energy that is not reflected back from the reference reflector surface 120 passes through the reference reflector surface 120 and onto an imaging lens 2050. The imaging lens 2050 images the light energy from the tips of the fiber channels 2040 onto the tissue of the subject 121. The light energy passes through the imaging lens 2050 onto a reflector surface 2060, which turns the light energy 90 degrees. This allows the light energy to be reflected out radially inside a tissue. There is one reflector surface 2060 for each fiber channel 2040. The light energy that is turned 90 degrees by the reflector surface 2060 is back reflected off of the tissue of subject 121, and nanoparticles 123.

The light is reflected from the tissue of subject 121 and the nanoparticles 123. The light energy strikes the reflector surface 2060 and is turned back 90 degrees. The light energy is then coupled by the imaging lens 2050 through the reference reflector surface 120 and back into each fiber channel 2040. The light energy reflected from the nanoparticles 123 and the tissue of subject 121 recombines and interferes with the light reflected from the reference reflector surface 120 in the fiber channels 2040. The recombined light energy can be coupled back into the lens array 2030 through the collimator lens 2020 and back into Port 2 of the fiber circulator 2010. The recombined light energy exits the fiber circulator 2010 through Port 3. A coupling lens 2080 couples the recombined light energy from the fiber circulator 2010 into a photo receiver 2090. The photo receiver 2090 converts the light energy signal into a voltage signal that is proportional to the number of photons contained in the recombined light energy. The voltage signal passes from the photo receiver 2090 into a pre/amp 2100. The pre/amp 2100 takes the voltage signal and amplifies it. The amplified voltage signal enters an A/D converter 2110. The A/D converter 2110 digitizes the voltage signal. This digital light signal data then enters the computer 101 through the OCT input interface 111. The digital light signal data 108 can be stored in the mass storage device 104 or system memory 112 and utilized by the image construction software 106 and the nanoparticle movement (or cellular membrane tension level or internal strain field) image construction software 107.

The method can further comprise generating light energy for at least two successive sweeps of light energy. A sweep is an emission of light from a light source across a range of optical frequencies. Multiple sweeps can be combined with application of a magnetic field to generate images with and without a magnetic field applied.

The method can further comprise applying a magnetic field to the subject for each of the successive sweeps of the light energy wherein the strength of the magnetic field applied in a sweep is greater than the strength of the magnetic field from the preceding sweep and wherein the magnetic field causes movement of at least one of the metallic nanoparticles. The method can further comprise applying the magnetic field from a source external to the subject or from a source internal to the subject. A coil generating the magnetic field can be integrated into a catheter or can be external to the subject of the scan.

As shown in FIG. 18, a non-uniform magnetic field can be applied to the tissue of subject 121 and the nanoparticles 123. The non-uniform magnetic field can be applied by the magnet 116, which can be a magnet internal to the OCT probe 122 or the non-uniform magnetic field can be applied externally to the subject 121 by a magnet. Magnets 116 and external magnet are both controlled by magnet control 114.

The magnet control can provide the current source to power external magnet and magnet 116 and is under the control of the computer 101. The magnet control 114 interfaces with the computer 101 through the OCT output interface 110. The magnet control 114 can interface with the computer 101 via IEEE-488, IEEE-1394, Universal Serial Bus (USB), or the like.

The method can further comprise processing the received light energy to produce a phase sensitive OCT image. The image produced can have a phase resolution of at least 30 nanometers (nm). Phase resolution is defined as the phase delay of the light signal returning from the tissue scanned. For example, the image can have a phase resolution of about at least 30 nm, 25 nm, 20 nm, 15 nm, 10 nm, 5 nm, 4 nm, 3 nm, or 2 nm.

The processing of the received light energy can be performed by software components. The image construction software 106 and the nanoparticle movement (or cellular membrane tension level or internal strain field) image construction software 107 can be described in the general context of computer-executable instructions, such as program modules, being executed by one or more computers or other devices. Generally, program modules include computer code, routines, programs, objects, components, data structures, etc. that perform particular tasks or implement particular abstract data types. The image construction software 106 and the nanoparticle movement (or cellular membrane tension level or internal strain field) image construction software 107 can also be practiced in distributed computing environments where tasks are performed by remote processing devices that are linked through a communications network. In a distributed computing environment, program modules can be located in both local and remote computer storage media including memory storage devices.

The image construction software 106 can generate an image of the tissue of subject 121 from the light signal data 108. The image construction software 106 can receive the light signal data 108 and can perform a time-frequency transform (e.g. Fourier transform) on the light signal data 108 generating amplitude and phase data. The amplitude and phase data (optical path length difference (cτ) or optical time-delay (τ)) can be separated into discrete channels and a plot of intensity vs. depth (or amplitude vs. depth) can be generated for each channel. Such a plot is known in the art as an "A" scan. The composition of all the "A" scans can comprise one image.

The nanoparticle movement (or cellular membrane tension level or internal strain field) image construction software 107 generates an image of the movement of the nanoparticles 123 from the light signal data 108. The nanoparticle movement (or cellular membrane tension level or internal strain field) image construction software 107 receives the light signal data 108 for at least two successive sweeps of the light source 117 or the light source 212 and performs a Fourier transform on the light signal data 108 generating amplitude and phase data. The amplitude and phase data can be separated into discrete channels, one channel for each fiber channel 204, and a plot of phase vs. depth (optical time-delay (τ)) can be generated for each channel. Points of nanoparticle 123 movements are identified by the phase changes between two successive sweeps of the light source 117 or the light source 212 corresponding to two applied magnetic field strengths.

Optionally, an optical clock is used to trigger acquisition of the signal produced by the photodetector. The optical clock provides a set of uniformly spaced clock pulses with fixed intervals of optical frequency and at least one reference pulse. The fixed intervals of optical frequency are configured and specified in the optical clock to give a uniform train of pulses. The at least one reference pulse generated by the optical clock is utilized to provide a reference optical frequency or a trigger pulse. For example, the first reference pulse generated by the optical clock can correspond to an absorption line in a gas cell (e.g., Hydrogen Fluoride or Hydrogen Bromide). In this case the gas absorption line has a known optical frequency. The well-known absorption fingerprint bands in the HF gas cell result in a reduced detected intensity in the light transmitted through the gas cell, and as such provide a metric on the absolute lasing wavelength at the digitized samples of the photodetector signal. The digitized sample number or sampling time scale can thus be converted to absolute wavelength at one or more samples, depending on the number of absorption lines. The detected wavemeter photocurrent signal and the detected gas cell photocurrent signal are combined in the digitizer to provide the relationship between the sample number or sampling time and lasing wavelength throughout the entire sweep. The detected photocurrent signal from the gas cell is digitized concurrently with the OCT interferogram and correlated with the known HF fingerprint to determine the wavenumber bias ($k_o$) of the swept source laser. Knowledge of wavenumber bias ($k_o$) allows accurate determination of the absolute wavenumber of each digitized sample throughout the spectral sweep, effectively removing any wavenumber offsets and/or phase instabilities in the laser source, wavemeter and sampling electronics. Knowledge of the magnitude of the fixed intervals and the optical frequency of at least one clock pulse provides knowledge of the optical frequency of every clock pulse provided by the optical clock.

Optionally, additional information can be extracted from the light signal data 108 to generate additional images. The light signal data 108 can be further processed to extract the Doppler frequency shift as is readily known to one skilled in the art. The light signal data 108 can also be further processed to generate a Stokes parameter polarimetric image when used in conjunction with polarization sensitive OCT to extract polarization data from the light signal 108 as is readily known to one skilled in the art.

The methods and systems can be used to perform molecular identification to stabilize vulnerable plaque that is anticipated to rupture and cause heart attacks, strokes, and progression of peripheral vascular disease. It can also be used to identify macrophages present in degenerative eye diseases which can lead to blindness and selectively kill these pathologic cells to stabilize the eye degeneration. Generally, many cancers are known to be associated with the presence of macrophages, and it may provide a method for early cancer detection and treatment.

Example 2

Figure 11A:
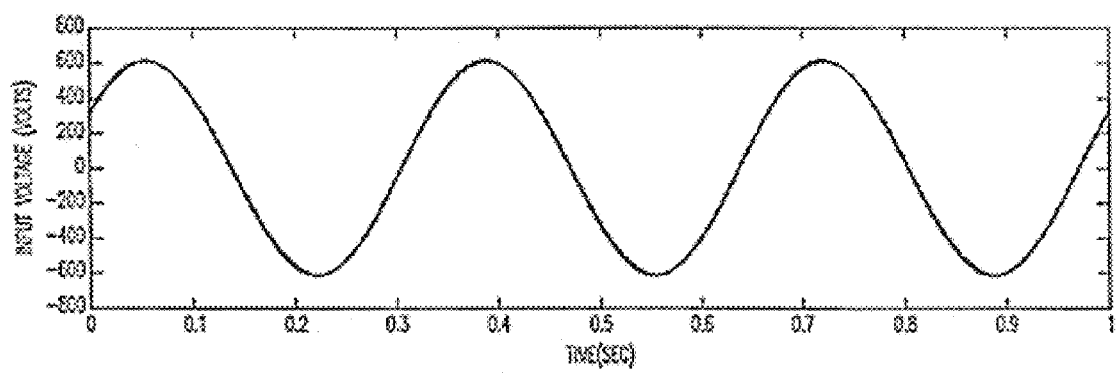
FIGS. 11A and 11B show solenoid drive signal and optical pathlength change observed in a mouse imaged with metallic nanoparticles (11A) and a mouse imaged without metallic nanoparticles (11B).
Figure 11A:
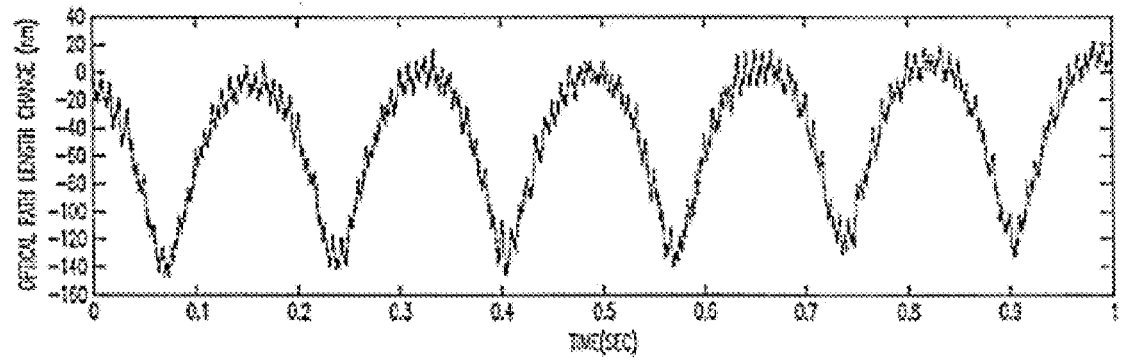
Figure 11B:
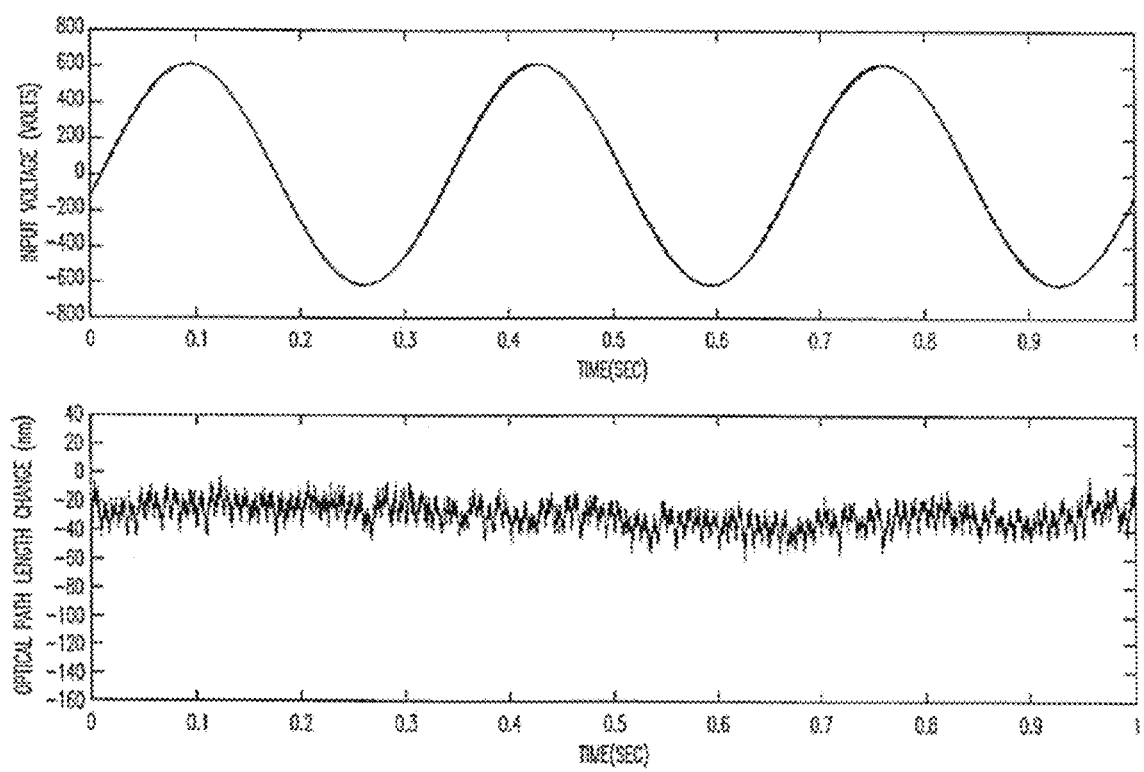

A solenoid coil with a ferrite core was used to apply a sinusoidal magnetic field to tissues taken from the liver of an ApoE −/− knockout mouse. One mouse was loaded with magnetic nanoparticles one week before imaging while an unloaded mouse served as a control. FIG. 11A shows a solenoid drive signal (top) and optical pathlength change (bottom) observed in mouse loaded with nanoparticles. FIG. 11B shows a solenoid drive signal (top) and optical pathlength change (bottom) observed in control mouse (no nanoparticles). These data demonstrate that iron oxide particles that have been ingested by macrophages in livers and spleens of the mice. Moreover, the particles have put in motion with a magnet and detected with differential phase OCT using the systems and methods described herein.

To calculate magnetic field strength a finite element method (FEM) can be used. Maxwell equations subjected to certain boundary conditions can be used to solve low-frequency magnetostatic problems. The use and solution of Maxwell equations are described in, for example, Monk P., Finite Element Methods for Maxwell's Equations, Oxford University Press, 2003, which is incorporated in its entirety by reference.

Maxwell equations can be written as:

$$\nabla \times H = J + \frac{\partial D}{\partial t} \quad (1.1)$$

$$\nabla \times E = -\frac{\partial B}{\partial t} \quad (1.2)$$

$$\nabla \cdot H = \rho \quad (1.3)$$

$$\nabla \cdot B = 0 \quad (1.4)$$

In case of magnetostatic problems $$\left(\frac{\partial D}{\partial t} = 0\right),$$

the magnetic field (H) and magnetic flux density (B) are satisfied with following equations:

$$\nabla \times H = J \quad (1.5)$$

$$\nabla \cdot B = 0 \quad (1.6)$$

B and H are subject to a generalized constitutive relation:

$$B = u_0(H+M) \quad (1.7)$$

Finite element methods (FEM) used magnetic vector potential (A) to find magnetic field strength.

$$B = \nabla \times A \quad (1.8)$$

Equation (1.5) can be rewritten as $$\nabla \times (u_0^{-1} \nabla \times A - M) = J \quad (1.9)$$

From equation (1.9), magnetic field strength and flux density can be solved. The symbols and unit for electromagnetic quantities for solving FEM problems include:
H: Magnetic field (Ampere/m)
E: Electric field (Volt/meter)
B: Magnetic flux density (Tesla)
D: Electric flux density (Coulomb/meter$^2$)
A: Magnetic potential (Weber/meter)
M: Magnetization (Ampere/meter)
$u_0$: Permeability of vacuum=$4\Pi \cdot 10^{-7}$ (H/m)

$$\nabla B = divB = \frac{\partial}{\partial x}B_x + \frac{\partial}{\partial y}B_y + \frac{\partial}{\partial z}B_z (\nabla \cdot B \text{ is divergence of } B)$$

Magnetic fields of between about 0.5, 1.5 and 2.0 Tesla were used to cause movement of the nanoparticles. Magnetic fields between about 1.0 and 9.0 Tesla can also be used. The magnetic field used is typically higher if the tissue of interest comprises a greater number of nanoparticles or iron, when compared to tissue with fewer nanoparticles or iron.

Example 3

Colloidal suspensions of SPIO nanoparticles are tissue-specific MRI contrast agents approved by the United States Food and Drug Administration (FDA) for human use in 1997. SPIO particles are also known as Ferumoxides or AMI-25 and their trade name is Feridex® I.V. (USA) and Endorem® (EU). Mean core diameter of these particles is 20 nm and total aggregation diameter is about 100 nm. SPIO nanoparticles comprise nonstoichiometric magnetite crystalline cores, iron, and dextran T-10 coating that is used to prevent aggregation and stabilization in the liver. 80% of injected dose of SPIO nanoparticles accumulate in tissue based macrophages (Kupffer cells) due to the relatively short blood half life compared to ultrasmall SPIO nanoparticles. Uptake of SPIO nanoparticles by macrophage cells is directly proportional to the intravenous injection (IV) concentration, blood half life, and core size.

To evaluate magnetic force on superparamagnetic (SPIO) nanoparticles, magnetic potential energy, U, can be used to calculate force due to application of an external magnetic flux density (B).

$$U = -\frac{1}{2}m \cdot B \quad (11)$$

If a magnetic material is exposed to an external magnetic flux density, B, the individual particles have overall response determined by the magnetic moment, m. The magnetic flux density on magnetic nanoparticles can be written:

$$B = u_0(H+M) \quad (12)$$

where $\mu_0$ ($4\pi \times 10^{-7}$ H/M) is the permeability of free space, and M is the magnetic moment per unit volume and H is magnetic field strength. The magnetic moment, m, acting on magnetic volume, V is given by, m=MV. Magnetization of magnetic particles can be classified in terms of the standard relation M=$\chi$H. Therefore, magnetic moment m becomes:

$$m = MV = \chi_s VH = \chi_s VB/u_0 \quad (13)$$

In Eq. (13), susceptibility of the SPIO particles $\chi_s$ is dimensionless in SI units and given by dipole density for each paramagnetic material and is an important parameter characterizing magnetic properties of SPIO nanoparticles. From Eq. (11), magnetic energy U, of a SPIO nanoparticles in external magnetic field is given by, $$U = -\frac{1}{2}m \cdot B = -\frac{\chi V}{2u_0}B^2 \quad (14)$$

Magnetic force acting on SPIO nanoparticles becomes:

$$F = -\nabla U = \nabla\left(\frac{\chi_s V}{2u_0}B^2\right) = \chi_s V \nabla\left(\frac{B^2}{2u_0}\right). \quad (15)$$

A sinusoidal magnetic flux density that is principally along the z-direction was assumed. Hence, $\vec{B}(x, y, z; t) = \sin(2\pi f_n t)B_z(z)\hat{k}$ and the magnetic force $F_z$ acting on nanoparticles in the z-direction is given by $$\sum F_z = m\frac{\partial^2 z(t)}{\partial t^2} = F_m - kz(t) - r\frac{\partial z}{\partial t} \quad (16)$$

$$\sum F_z = \frac{\chi_s V_s}{2\mu_0}[1-\cos(4\pi f_n t)]B_z(z)\frac{\partial B_z}{\partial z} - kz(t) - r\frac{\partial z}{\partial t}, \quad (17)$$

where $F_m$ is magnetic force, $f_n$ is the modulation frequency of the applied sinusoidal magnetic field, $kz(t)$ is an elastic restoring force, and $$r\frac{\partial z}{\partial t}$$

is a viscous drag force that account for the viscoelastic properties of the local tissue environment. The negative sign of the viscous drag and restoring force indicates that this force is in opposite direction to movement $z(t)$. Equation 17 can be written by dividing by the mass, m.

$$\frac{\partial^2 z(t)}{\partial t^2} + \frac{kz(t)}{m} + \frac{r}{m}\frac{\partial z}{\partial t} = \frac{\chi_s V_s}{2m\mu_0}[1-\cos(4\pi f_n t)]B_z(z)\frac{\partial B_z}{\partial z} \quad (18)$$

Equation 18 can be rewritten using the first terms in the Maclarin series for the magnetic field, $$\frac{\partial^2 z(t)}{\partial t^2} + \frac{r}{m}\frac{\partial z}{\partial t} + \frac{kz(t)}{m} \cong \frac{\chi_s V_s}{2m\mu_0}[1-\cos(4\pi f_n t)]B_z(0)\frac{\partial B_z(0)}{\partial z} \quad (19)$$

Letting $$a = \frac{\chi_s V_s}{2m\mu_0}B_z(0)\frac{\partial B_z(0)}{\partial z}, \quad c = 4\pi f_n,$$

the second order differential Eq. (19) can be written $$\frac{\partial^2 z(t)}{\partial t^2} + \frac{r}{m}\frac{\partial z}{\partial t} + \frac{kz(t)}{m} = a[1-\cos(ct)], \quad (20)$$

The Laplace transform can be used to solve the second order differential equation (20), assuming zero initial displacements and velocity to find;

$$s^2 Z(s) + \frac{r}{m}sZ(s) + \frac{k}{m}Z(s) = \frac{a}{s} - \frac{as}{(s^2+c^2)} \quad (21)$$

$$Z(s) = \frac{\frac{a}{s} - \frac{as}{(s^2+c^2)}}{\left(s^2 + \frac{r}{m}s + \frac{k}{m}\right)} = a\left(\frac{1}{\left(s^2 + \frac{r}{m}s + \frac{k}{m}\right)s} - \frac{s}{\left(s^2 + \frac{r}{m}s + \frac{k}{m}\right)}\right)$$

By computing the sum of the transforms, $Z(s)$ can be derived in Eq. (21)

$$z(t) = \frac{ma\left(\begin{array}{c}-2mkc^2 + c^2r^2 + k^2 + c^4m^2 - \cos(ct)k^2 + \\ \cos(ct)c^2mk - cr\sin(ct)k + \\ \exp\left(-\frac{1}{2}\frac{tr}{m}\right)\left(\begin{array}{c}c^2\left(km - r^2 - c^2m^2\right)\cosh\left(\frac{1}{2}\frac{t(r^2-4km)^{\frac{1}{2}}}{m}\right) + \\ \frac{c^2 r(3km - r^2 - c^2m^2)\sinh\left(\frac{1}{2}\frac{t(r^2-4km)^{\frac{1}{2}}}{m}\right)}{(r^2-4km)^{\frac{1}{2}}}\end{array}\right)\end{array}\right)}{(k(-2mkc^2 + c^2r^2 + k^2 + c^4m^2)} \quad (22)$$

The displacement $z(t)$ of nanoparticles can be found by using an inverse Laplace transform; the solution includes transient and steady state terms. The initial motion of magnetic nanoparticles is driven by a constant magnetic force and displays a damped transient motion before steady state motion dominates at twice the modulation frequency ($f_n$) of the applied sinusoidal magnetic field. Motion of the nanoparticles at double the modulation frequency originates from the magnetic force being proportional to the product of the field and field-gradient (Eq. 17).

Liver tissues from 12 week old ApoE$^{-/-}$ high fat fed mice were utilized because they contain tissue based macrophages cells. The mice were injected via the jugular vein with either Feridex I.V. (Ferumoxides injectable solutions; Berelex Laboratories, Montville, N.J.) for intravenous administration (1.0, 0.1, and 0.01 mmol Fe/kg body weight) or saline and sacrificed 2 days post intravenous injection. The mice were euthanized with a lethal dose of Ketamine and Xylazine. After euthanizing, abdominal incisions were made to remove the entire liver from the mouse. Portions were cut using a microtome. Physical thickness of the liver samples was 1 mm and 0.5 cm×0.5 cm in lateral dimensions. After completion of the DP-OCT measurements, the mouse livers were embedded in 10% formalin acid, and processed for histology. 5 μm thick sections were cut and stained with Prussian blue to identify iron deposition in liver Kupffer cells in mouse liver tissues. To verify SPIO uptake by macrophage cells from histology slides, Image Pro Plus® (Mediacynernetics Inc., Silver Spring, Md.) was used to measure the total area of liver and accumulated area of SPIO aggregation containing Prussian blue positive.

Figure 12A:
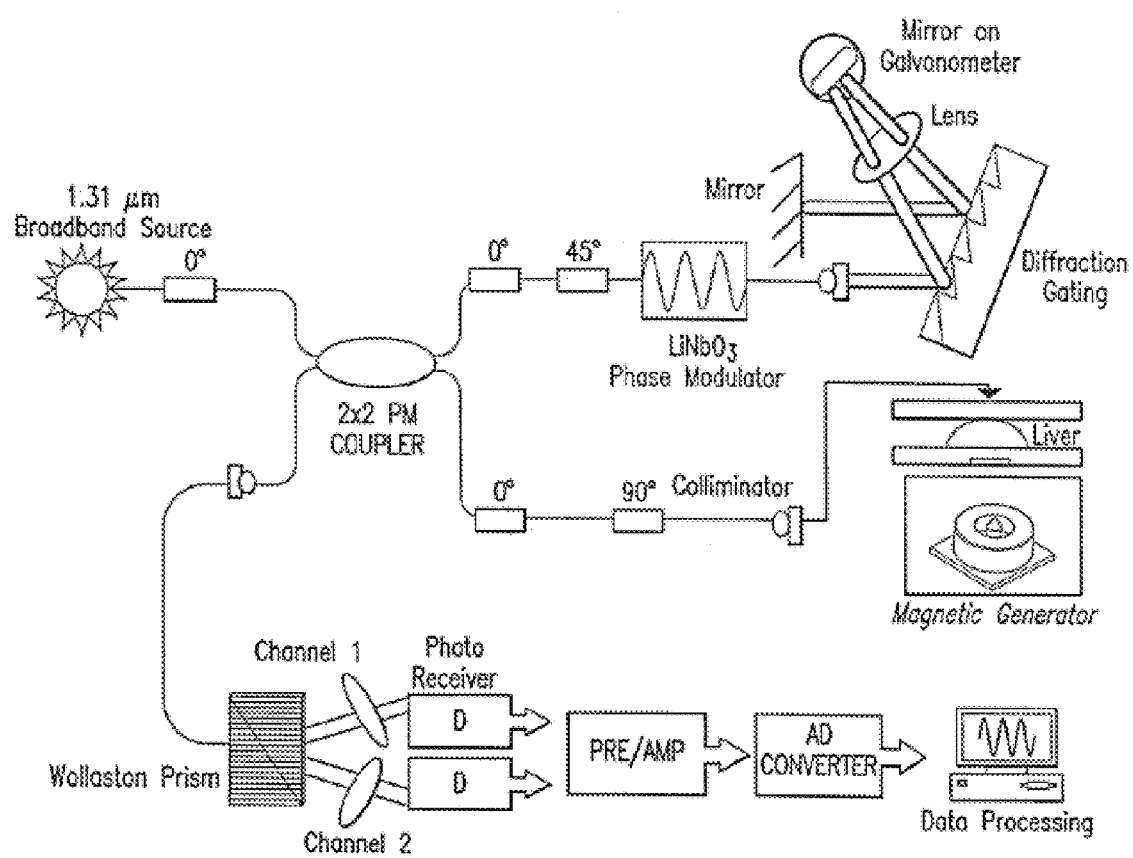
FIGS. 12A-B shows a schematic diagram of a differential phase optical coherence tomography (DP-OCT) system combined with a magnetic field generator: (12A) DP-OCT system, (12B) collinear configurations of the DP-OCT sample path and design of the magnetic field generator containing a conical iron core.
Figure 12B:
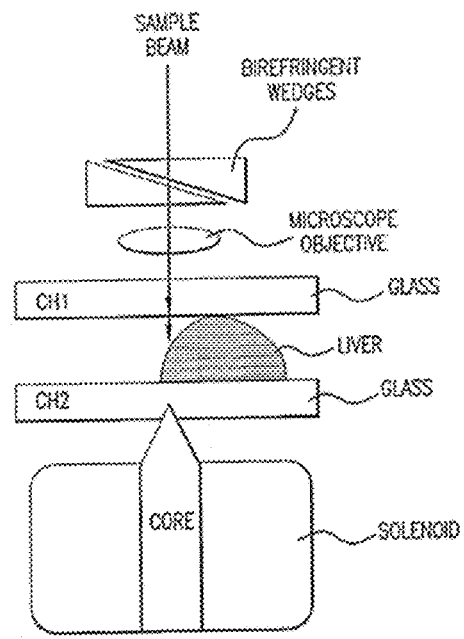

FIGS. 12A and 12B shows a schematic diagram of a fiber-based dual channel differential phase optical coherence tomography (DP-OCT) system (a), and sample path configuration with a magnetic field generator (b). The magnetic field generator comprises a solenoid, signal generator and current amplifier. A dual-channel Michelson interferometer was used to measure differential phase between light backscattered from a sample by applying a sinusoidal focused magnetic field excitation. Partially polarized light from an optical semiconductor amplifier (AFC Technologies, Rancho Cordova, Calif., central wavelength $\lambda_0$=1.31 μm, FWHM=60 nm, optical coherence length=22 μm) is polarized and coupled into fast and slow axes of a polarization-maintaining (PM) fiber in the input port.

Optical path length change (Δp) in tissue can be calculated from the differential phase (Δφ) and central wavelength of a broad-band light source ($\lambda_0$=1,310 nm) between the two channels.

$$\Delta p = \frac{\lambda_0}{4\pi} \Delta \varphi \qquad (23)$$

The displacement z(t) of tissue-laden nanoparticles driven by a time (t) varying magnetic flux density can be derived the analytic OCT fringe expression, $$I_f = 2\sqrt{I_R I_S} \cos\left[2\pi f_0 t + \frac{4\pi z(t)}{\lambda_0}\right] \qquad (24)$$

Where $I_R$ and $I_S$ are the back scattered signals from the reference and sample arms, respectively. $f_0$ is the fringe carrier frequency, and z(t) is the nanoparticles displacement. The OCT fringe signal can be expressed by the nanoparticles displacement equation (24). The two signals recorded from Channel 1 and 2 by the DP-OCT system can be used to measure nanoparticles displacement that represent relative surface tissue displacement between two scanning beams.

Finite element method (FEM) was used to design the magnetic field generator and evaluate space-time magnetic flux density. The magnetic field generator comprises a solenoid (Ledex 6EC, Saia-Burgess Inc., Vernon Hills, Ill.), a function generator (HP 33120A, Hewlett Packard Inc., Palo Alto, Calif.), a current amplifier, and a power supply. FEM calculations (Maxwell SV, Ansoft Inc., Pittsburgh, Pa.) and Teslameter® (Magnetometer®, AlphaLab Inc., Salt Lake City, Utah) measurement indicated that the maximum magnetic flux density at a distance of 1.5 mm from the tip of the iron core was approximately 2 Tesla. The FEM simulation demonstrated that an iron core positioned along the centerline of the solenoid dramatically increased magnetic flux density at the target specimen. Magnetic field distributions from the FEM simulation showed the maximal and principal direction of the magnetic field strength was in the z-direction. The conical iron core provided focusing and substantially increased the magnetic field strength.

Figure 13A:
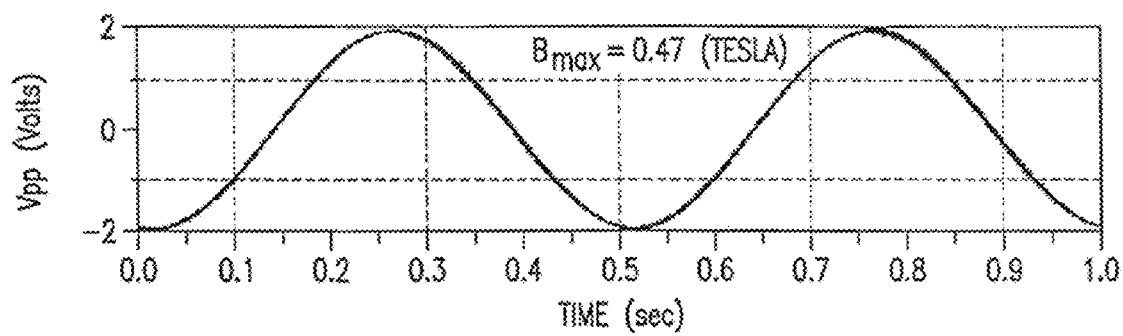
FIG. 13A-13D shows the optical path length change (Δp) in livers with different SPIO doses (1.0, 0.1 mmol Fe/kg and saline control) using focused magnetic field excitation (2 Hz, 4 $V_{pp}$) (13A). Optical path length change (Δp) in specimens with doses 1.0 mmol Fe/kg SPIO (13D), 0.1 mmol Fe/kg SPIO (13B), and a saline control liver (13C). The applied magnetic flux density strength is $B_z$=0.47 Tesla at the liver specimen.
Figure 13D:
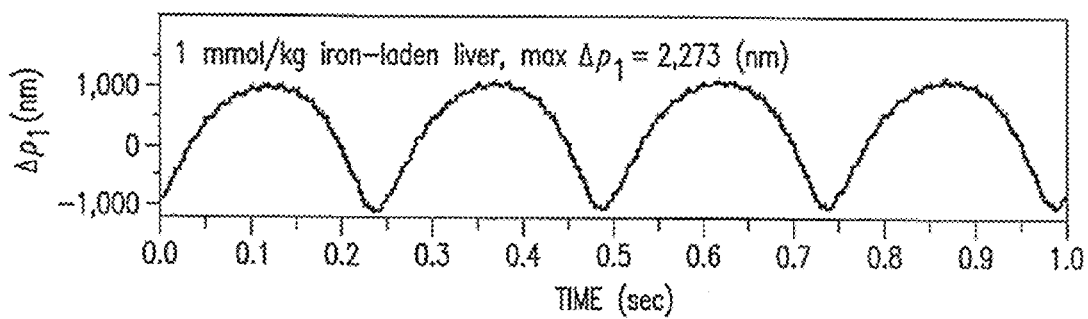
Figure 13B:
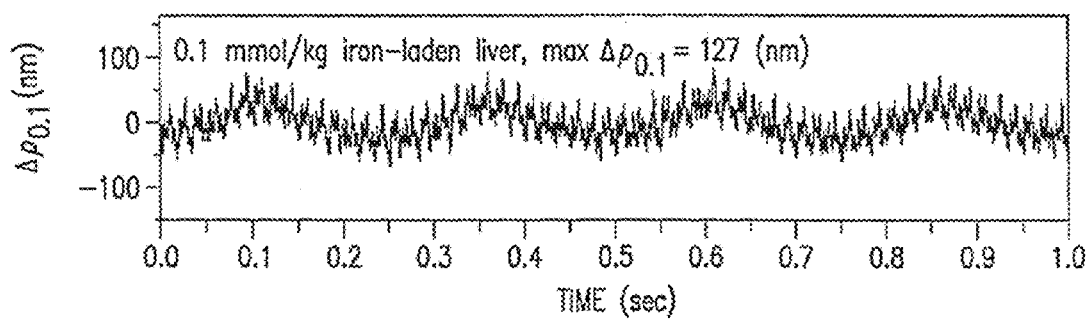
Figure 13C:
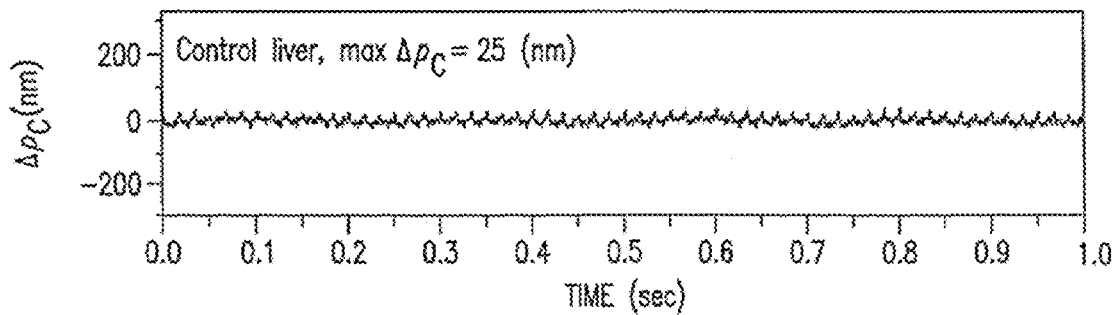

Differential phase OCT (DP-OCT) measurements were performed on isolated liver specimens taken from ApoE−/− mice administrated with different SPIO doses (1.0, 0.1 and 0.01 mmol Fe/kg body weight) and saline control samples. FIG. 7 demonstrates measurements of transient optical path length change (Δp) in specimens at different SPIO doses (1.0, 0.1 mmol Fe/kg body weight) and saline control samples, in response to application of a sinusoidal varying focused magnetic field. FIG. 13A shows a magnetic field input ($f_n$=2 Hz), peak-to-peak voltage ($V_{pp}$=4) over a 1 second time period. The maximum magnetic field strength was 0.47 Tesla and maximal tissue displacement by optical path length change (Δp) was 2,273 nm in the 1.0 mmol Fe/kg iron-laden liver. Compared to high dose specimens, 0.1 mmol Fe/kg iron-laden liver showed a maximum optical path length change (Δp) of 127 nm with additive noise visible in recorded signals. Frequency response (4 Hz) of iron-laden livers (FIG. 7 (b), (c)) was exactly twice the modulation frequency (2 Hz) as noted earlier. No significant displacement of SPIO nanoparticles was observed in either saline control liver specimens in the FIG. 13D or samples at the 0.01 mmol Fe/kg dose (not shown).

Figure 14A:
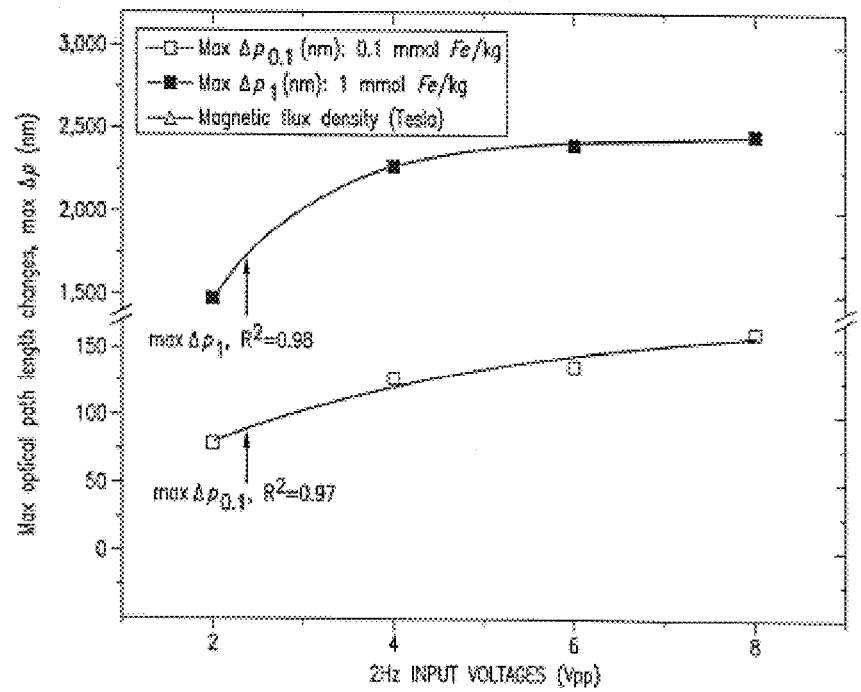
FIG. 14A-B shows the maximum optical path length change (Δp) in iron-laden liver specimens due to nanoparticle movement in response to a focused magnetic field for mice injected with various SPIO doses (1.0 and 0.1 mmol Fe/kg). The input frequency is 2 Hz with applied voltage ranging from 2 to 8 $V_{pp}$ (14A) and magnetic field strength at each input voltage (14B).
Figure 14B:
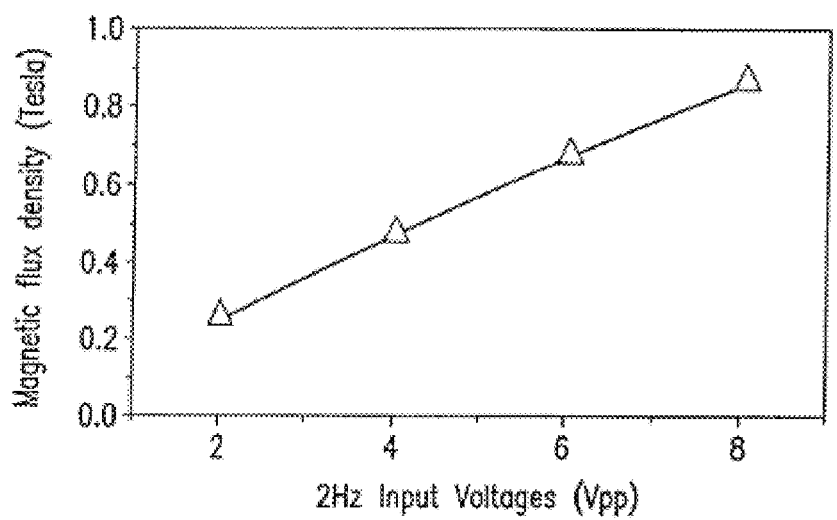

SPIO nanoparticle movement in the iron laden livers (0.1, and 1.0 mmol Fe/kg) was used to observe quantitatively the relationship between optical path length change (Δp) versus different applied magnetic field strengths, as shown in FIG. 14A. Input frequency used in this experiment was 2 Hz with amplitude from 2 to 8 $V_{pp}$. FIG. 8 (b) shows magnetic flux density at the same voltages as in FIG. 14A. Magnitude of optical path length change (Δp) indicating movement of iron-laden liver depended directly on the SPIO dose concentration, and strength of the external magnetic field.

Optical path length change (Δp) at high frequency modulation (over 100 Hz) was negligible due to limited frequency response of the structures surrounding SPIO nanoparticles. Generally, optical path length change (Δp) due to nanoparticles movement in tissue increased with higher magnetic field strength.

Figure 15A:
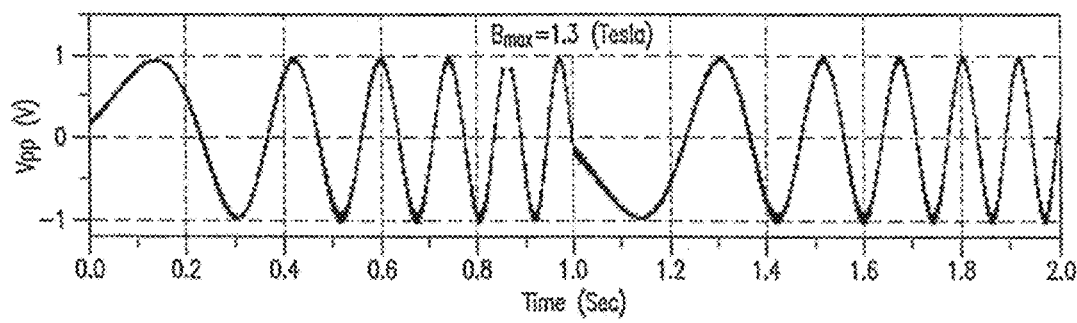
FIG. 15A-D shows the Optical path length change (Δp) in iron-laden liver specimens due to nanoparticle movement in response to a focused magnetic field with a swept frequency (1~10 Hz) input for mice injected with various SPIO doses (1.0 and 0.1 mmol Fe/kg). (15A). Optical path length change (Δp) at 1.0 mmol Fe/kg SPIO dose (15B), 0.1 mmol Fe/kg SPIO dose (15C), and a saline control liver (15D). The applied focused magnetic flux density is 1.3 Tesla at the specimen.
Figure 15B:
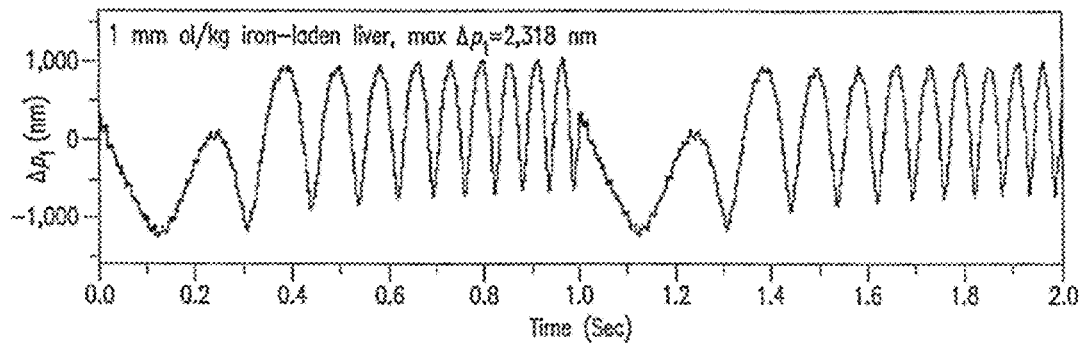
Figure 15C:
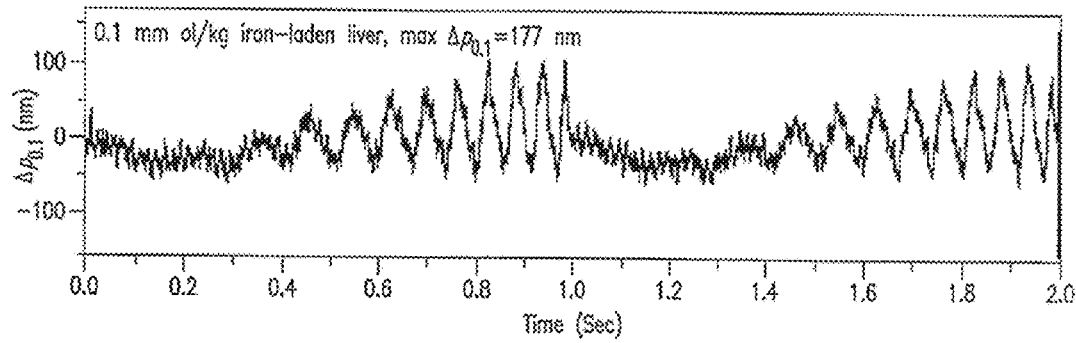
Figure 15D:
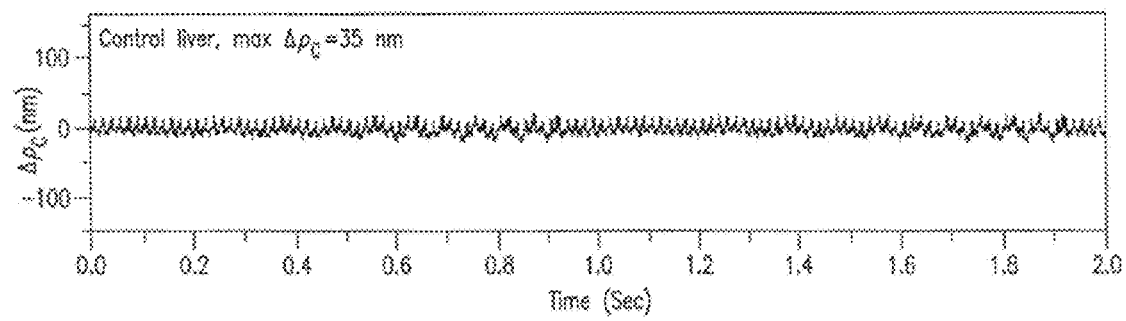

Optical path length change (Δp) in the iron-laden liver (0.1 and 1.0 mmol Fe/kg) can be measured using a swept input frequency as shown in FIG. 15A. FIG. 15A shows the magnetic field input with a swept frequency from 1 to 10 Hz over a 2 second time-period. Magnitude of the optical path length change (Δp) was 2,318 nm in a high dose liver (1.0 mmol Fe/kg) and 177 nm in a low dose concentration (0.1 mmol Fe/kg), and magnetic field strength was 1.3 Tesla. The frequency response of the force acting on the iron-laden liver is exactly twice the externally applied modulated frequency in FIG. 15B and FIG. 15C. No significant displacement was observed in the saline control liver shown in FIG. 9 (d) and 0.01 mmol Fe/kg liver specimens.

Figure 16A:
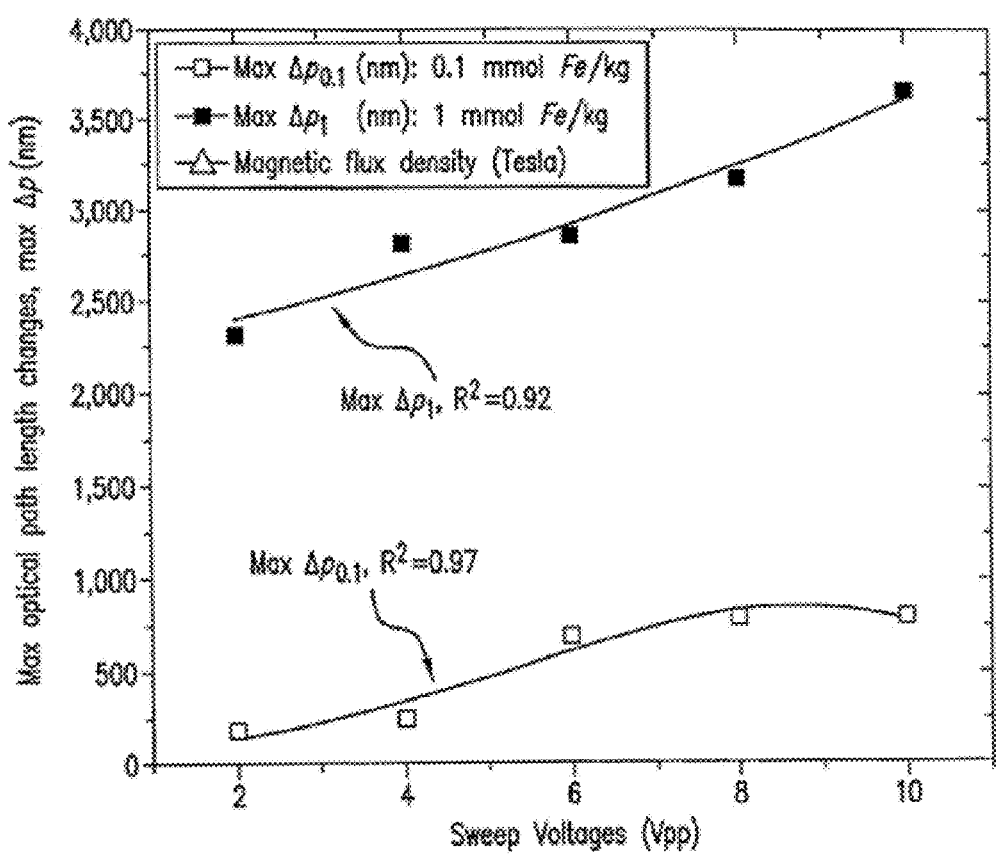
FIGS. 16A-B shows the maximum optical path length change (Δp) in iron-laden liver specimens due to nanoparticle movement in response to a focused magnetic field with a swept frequency (1~10 Hz) input for mice injected with various SPIO doses (1.0 and 0.1 mmol Fe/kg). Input swept frequency ranged from 1~10 Hz over 2 seconds with input voltages increasing from 2 to 10 $V_{pp}$ (16A) and magnetic field strength at each input voltage (16B).
Figure 16B:
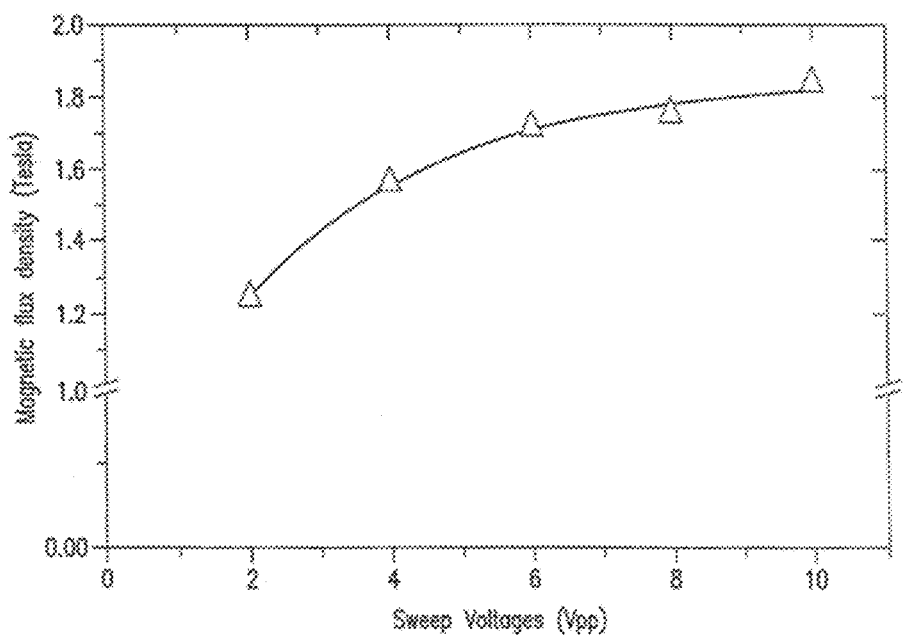
Figure 17A:
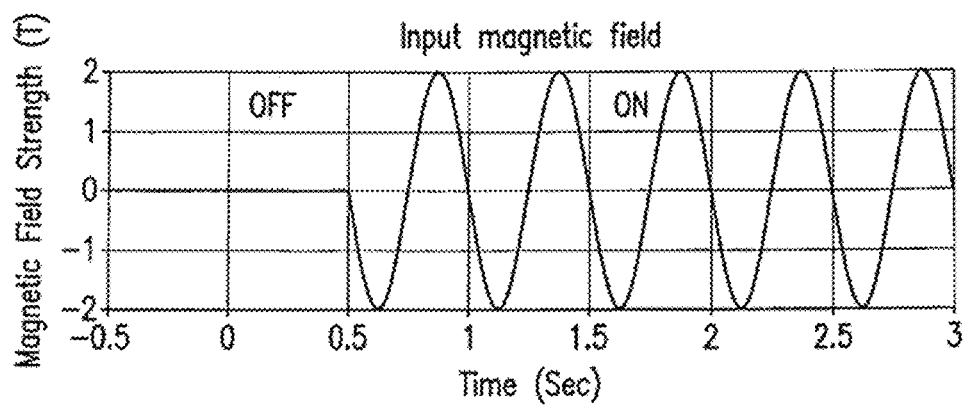
FIGS. 17A-17E shows optical path length change (Δp) in iron-laden rabbit arteries (0.1 Fe/kg) measured in response to 2 Hz frequency sinusoidal inputs.
Figure 17B:
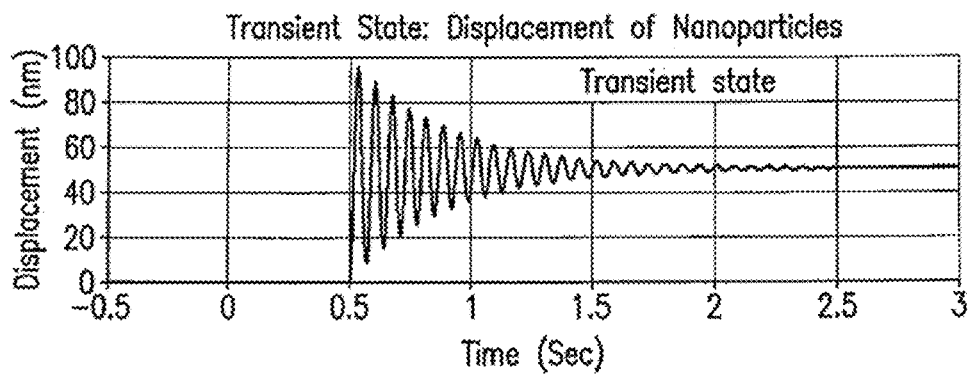
Figure 17C:
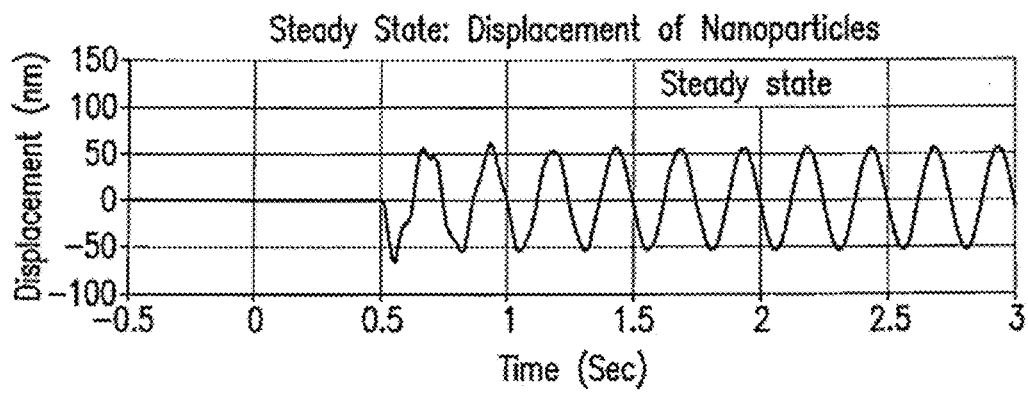
Figure 17D:
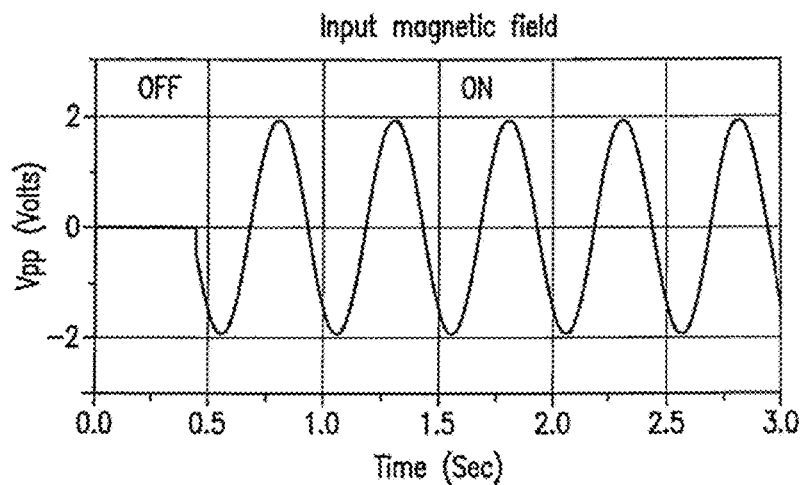
Figure 17E:
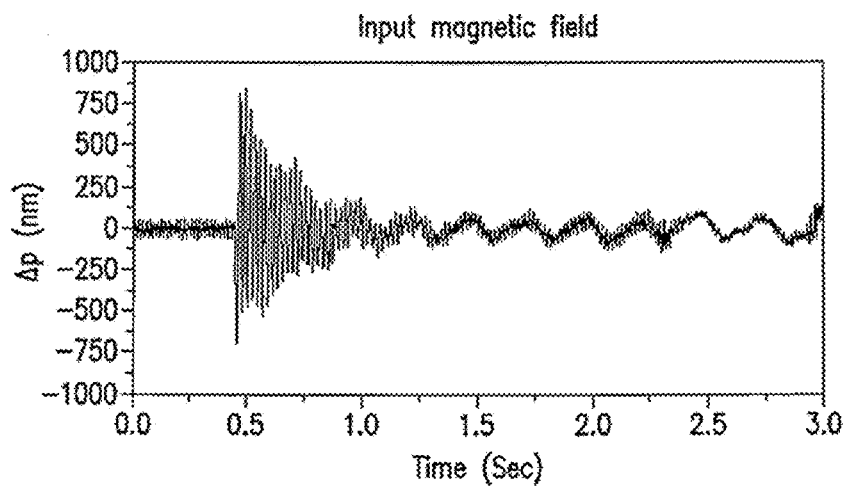

FIGS. 16A and 16B illustrates SPIO nanoparticle movement measured by optical path length change (Δp) in a iron-laden mouse liver to observe quantitatively the relationship between magnetic response in tissue versus different applied magnetic field strengths with swept frequency ranging from 1~10 Hz over a 2 second time-period. Magnitude of optical path length change (Δp) was larger when input voltage was gradually increased from 2 to 10 $V_{pp}$ during a frequency sweep. Corresponding magnetic field strength at these voltages was 1.24, 1.58, 1.71, 1.75 and 1.84 Tesla, respectively. For a given frequency sweep, maximum optical path length change (Δp) for 0.1 and 1.0 mmol Fe/kg iron-laden liver specimens was 3,700 nm and 750 nm, respectively, at 10 $V_{pp}$, and magnetic field of 1.84 Tesla.

SPIO nanoparticles were identified in histological specimens as blue granules from the Prussian blue stain of iron laden mouse livers. Compared to control liver specimens, iron laden specimens show significant iron accumulation evenly distributed in all observed areas. Although intracellular iron was also observed in control specimens, this natural iron was uniform and homogeneous rather than appearing in granular shapes as SPIO iron nanoparticles. Total SPIO iron area was 5.45% of the histology image as calculated by Image-Pro PLUS 5.1 software (Mediacynernetics Inc., Silver Spring, Md.).

Example 4

Optical path length change (Δp) in iron-laden rabbit arteries (0.1 Fe/kg) was measured in response to 2 Hz frequency sinusoidal input FIG. 17. FIG. 17A shows the magnetic field input with a constant frequency at 2 Hz over a 2.5 second time-period. Magnitude of the optical path length change (Δp) indicated a transient and steady state response. Transient response is evident in the exponentially decaying oscillation in the observed measured optical path length change at times between 0.5-1.0 seconds. Steady state response is evident in the uniform oscillation in the measured optical path length change at times between 1.25-3.0 seconds. Transient response indicates a high frequency (40 Hz-80 Hz) "ringing" oscillation and a damping relaxation time of approximately 0.3 seconds. The steady state frequency response of the force acting on the iron-laden rabbit artery was exactly twice the externally applied modulated frequency in FIG. 11 (b).

Throughout this application, various publications are referenced. The disclosures of these publications in their entireties are hereby incorporated by reference into this application in order to more fully describe the state of the art to which this invention pertains.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A system for imaging, comprising:
    a magnet for applying a magnetic field to the vessels to be imaged, wherein the applied magnetic field interacts with hemoglobin within the vasculature; and
    an optical coherence tomography apparatus for detecting magnetic movement of the hemoglobin within the vasculature, wherein optical coherence tomography apparatus includes a tunable laser source in the optical frequency domain and an optical clock to sample interference fringe data uniformly spaced in the optical frequency domain.

2. The system of claim 1, wherein the magnetic field is oscillating.

3. The system of claim 1, wherein the magnet comprises a solenoid coil with a ferrite core.

4. The system of claim 3, wherein the optical coherence tomography apparatus further comprises a sample arm, and wherein a probe is coupled to the sample arm of the optical coherence tomography apparatus and the magnet.

5. The system of claim 4, wherein the optical coherence tomography apparatus is a magneto-motive optical Doppler tomography imaging system for detecting the blood flow affected by the magnetic field.

6. The system of claim 5, wherein the magneto-motive optical Doppler tomography system comprises:
    a light source generating light energy;
    an interferometer coupled to the light energy, wherein the interferometer includes a reference and sample light paths coupled to a light splitter;
    a modulator coupled to the interferometer for modulating the optical path length difference in the reference arm and the sample arm;
    a scanner coupled to the sample arm for scanning a biological sample;
    a rapid scanning optical delay line coupled to the reference arm;
    a photodetector coupled to the interferometer for detecting backscattered radiation received by the interferometer from the scanner to detect interference fringes; and
    a processor for processing the reflected light energy from the reference arm and a signal reflected off of the moving blood flow to produce a tomographic image and a tomographic flow velocity image.

7. The system of claim 6, wherein the magneto-motive optical Doppler tomography system includes a scanning element to permit three dimensional scans.

8. The system of claim 7, wherein the magneto-motive optical Doppler tomography system includes a dual-balanced photodetector.

9. The system of claim 8, wherein the magneto-motive optical Doppler tomography system includes a circulator coupled to the interferometer and the photodetector.

10. The apparatus of claim 4, wherein the optical coherence tomography system for detecting blood flow is a spectral domain phase sensitive optical coherence tomography system.

11. The apparatus of claim 4, wherein the optical clock is selected from the group consisting of: absorption line in a gas cell including a known optical frequency, an optical comb source including a power spectral density uniformly spaced in the optical frequency domain at a fixed optical frequency interval, and a Fabry-Perot interferometer including a power spectral density uniformly spaced in the optical frequency domain at a fixed optical frequency interval.

12. A method for imaging a blood flow, comprising:
    applying a magnetic field to the blood flow with a magnet, wherein the blood flow comprises a plurality of hemoglobin molecules and wherein the magnetic field interacts with the hemoglobin to cause a change in the blood flow; and
    detecting the blood flow by detecting the change in the blood flow caused by the interaction with the hemoglobin molecules with the magnetic field, wherein the change is detected using an optical coherence tomography system, wherein optical coherence tomography apparatus includes a tunable laser source in the optical frequency domain and an optical clock to sample interference fringe data uniformly spaced in the optical frequency domain.

13. The method of claim 12, wherein the applying of the magnetic field comprises temporally oscillating the magnetic field.

14. The method of claim 13, further comprising coupling the optical coherence tomography system and the magnetic field to a probe.

15. The method of claim 14, wherein the detecting the blood flow by detecting the change in the blood flow caused by the interaction with the hemoglobin molecules, wherein the change is detected using a magnetomotive optical Doppler tomography imaging system.

16. The method of claim 15, wherein the magneto-motive optical Doppler tomography system comprises the method of
    providing light energy through an interferometer;
    phase modulating the light energy in the interferometer at a modulation frequency;
    continuously scanning a blood flow sample with the light energy through the interferometer, wherein the blood flow sample includes a blood flow therein and a structure in which the blood flow is defined;
    detecting the signal reflected off the moving blood sample and the interference fringes of the light energy backscattered from moving blood sample; and
    data processing Doppler frequency changes of the detected backscattered interference fringes with respect to said modulation frequency at each pixel of a scanned image to continuously measure the interference fringe intensities to obtain time dependent power spectra for each pixel location in a data window in a continuous scan from which a tomographic image of the blood flow in and the structure of said scanned blood flow sample is formed.

17. The method of claim 15, wherein the modulation frequency is zero.

18. The method of claim 16, where detecting the interference fringes of light energy backscattered from the moving blood sample includes reducing the light source noise from the interference signal with a dual balanced photodetector.

19. The method of claim 17, further including improving imaging speed with a hardware in-phase and a quadrature demodulator with at least one high-bandpass filter.

20. The method of claim 12, wherein the detecting of the change in the blood flow caused by the interaction with the hemoglobin molecules is detected using a spectral domain phase sensitive optical coherence tomography system.

* * * * *